United States Patent [19]

Sugimura et al.

[11] Patent Number: 5,650,430
[45] Date of Patent: Jul. 22, 1997

[54] RADICICOL DERIVATIVES, THEIR PREPARATION AND THEIR ANTI-TUMOR ACTIVITY

[75] Inventors: Yukio Sugimura; Kimio Iino; Yoshio Tsujita; Yoko Shimada; Tomowo Kobayashi, all of Hiromachi; Takeshi Kagasaki, Iwaki, all of Japan

[73] Assignee: Sankyo Company, Limited, Tokyo, Japan

[21] Appl. No.: 473,099

[22] Filed: Jun. 7, 1995

Related U.S. Application Data

[63] Continuation of Ser. No. 246,937, May 20, 1994, abandoned, which is a continuation of Ser. No. 988,167, Dec. 9, 1992, abandoned, which is a continuation-in-part of Ser. No. 711,217, Jun. 6, 1991, abandoned.

[30] Foreign Application Priority Data

Jun. 6, 1990 [JP] Japan ................. 2-146299

[51] Int. Cl.$^6$ ................................ A61K 31/335
[52] U.S. Cl. ................ 514/450; 514/444; 549/60; 549/214; 549/268
[58] Field of Search ................. 514/444, 450; 549/60, 214, 268

[56] References Cited

U.S. PATENT DOCUMENTS

| | | | |
|---|---|---|---|
| 3,428,526 | 2/1969 | Sigg et al. | 195/80 |
| 4,166,764 | 9/1979 | Calton et al. | 435/119 |
| 4,228,079 | 10/1980 | Calton et al. | 424/279 |

FOREIGN PATENT DOCUMENTS 2903997 9/1979 Germany.

OTHER PUBLICATIONS

Mirrington et al 'The Constitution of Radicicol' Tetrahedron Letters, No. 7, 1964, pp. 365–370.
Chem Abst., vol. 77, No. 25 (1972) No. 160508q.
Chem Abst., vol. 61 (1964) 14653 (McCapra et al).
Merck Index, Tenth Ed. 1983 pp. 894–895 Monograph No. 6107 "Monorden".
Chem Abst. vol. 60, (1964), 10623, (Mirrington).
Burger, A. *A Guide to the Chemical Basis & Drug Design* p. 15 1984.
Cutler et al, "Monorden from a Novel Source, *Neocosmospora tenuicristata*: Stereochemistry and Plant Growth Regulatory Properties", Agri. Biol. Chem. 51 (12) pp. 3331–3337, 1987.

*Primary Examiner*—Amelia Owens
*Attorney, Agent, or Firm*—Frishauf, Holtz, Goodman, Langer & Chick, P.C.

[57] ABSTRACT

Radicicol derivatives in which one or both hydroxy groups are acylated have valuable anti-tumor activity or may be used as chemical intermediates.

3 Claims, No Drawings

RADICICOL DERIVATIVES, THEIR PREPARATION AND THEIR ANTI-TUMOR ACTIVITY

This application is a continuation of application Ser. No. 08/246,937 filed May 20, 1994, now abandoned which is a continuation of application Ser. No. 07/988,167 filed Dec. 9, 1992 (abandoned), which is a continuation in part of application Ser. No. 07/711,217 filed Jun. 6, 1991 (abandoned).

BACKGROUND OF THE INVENTION

The present invention relates to a series of new derivatives of the compound "radicicol", which is also known by the name "monorden", and provides methods and compositions using them as well as processes for their preparation.

Radicicol (Merck Index, 11th Edition, monograph No 6163, "Monorden") was first isolated in 1953, and its structure was elucidated in 1964 by Mirrington et al. [Tetrahedron Letters, 7, 365 (1964)], who also disclosed the diacetyl derivative of radicicol. At that time, it was known to have an activity which can be broadly described as "antibiotic" (as it is described in the Merck Index), although, in fact, its activity is strictly anti-fungal. It is also known to have a relatively strong tranquilizing activity without having any effect on the central nervous system. Subsequently, it was disclosed in U.S. Pat. No. 3,428,526 that radicicol has a strong inhibitory effect in vitro on the growth of tumor cells of the mouse mastocytoma P-815. However, to date, no commercial use for the compound has been found.

We have found that radicicol itself can exert little anti-tumor activity against various types of tumor in vivo, and have also surprisingly found that certain acylated derivatives of radicicol demonstrate a superior anti-tumor activity. It is believed that the relative inactivity in vivo compared to the good activity in vitro may be a result of an instability of the compound to a component of the mammalian metabolism. We have, however, found that acylated derivatives of radicicol have greater stability in the mammalian body and can, therefore, be of practical use in the treatment of tumors.

BRIEF SUMMARY OF INVENTION

It is, therefore, an object of the present invention to provide as new compositions of matter a series of novel acylated radicicol derivatives.

It is a further object of the present invention to provide such compounds which may demonstrate anti-tumor activity.

Other objects and advantages of the present invention will become apparent as the description proceeds.

The compounds of the present invention are those compounds of formula (I):

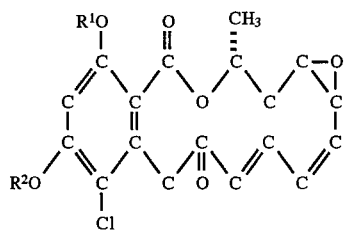

in which:

$R^1$ and $R^2$ are independently selected from the group consisting of hydrogen atoms and groups of formula $R^3$—CO—, where each of the symbols $R^3$ is independently selected from the groups consisting of:

hydrogen atoms;
alkyl groups having from 1 to 50 carbon atoms;
substituted alkyl groups which have from 1 to 50 carbon atoms and which are substituted by at least one substituent selected from the group consisting of substituents (a), defined below;
alkoxy groups which have from 1 to 20 carbon atoms and which are unsubstituted or are substituted by at least one substituent selected from the group consisting of substituents (a), defined below;
alkenyl groups having from 2 to 30 carbon atoms and having at least one carbon-carbon double bond;
substituted alkenyl groups which have from 2 to 30 carbon atoms, which have at least one carbon-carbon double bond and which are substituted by at least one substituent selected from the group consisting of substituents (a), defined below;
alkenyloxy groups which have from 2 to 30 carbon atoms and which are unsubstituted or are substituted by at least one substituent selected from the group consisting of substituents (a), defined below;
alkynyl groups having from 2 to 10 carbon atoms;
substituted alkynyl groups which have from 2 to 10 carbon atoms and which are substituted by at least one substituent selected from the group consisting of substituents (a), defined below;
aryl groups which have from 6 to 14 ring atoms and which are unsubstituted or which are substituted by at least one substituent selected from the group consisting of substituents (b), defined below;
aryloxy groups which have from 6 to 14 ring atoms and which are unsubstituted or which are substituted by at least one substituent selected from the group consisting of substituents (b), defined below;
heterocyclic groups which have 5 or 6 ring atoms, of which from 1 to 3 are selected from the group consisting of nitrogen, oxygen and sulfur heteroatoms, said heterocyclic group being unsubstituted or being substituted by at least one substituent selected from the group consisting of substituents (c), defined below;
heterocyclic groups which have 5 or 6 ring atoms, of which from 1 to 3 are selected from the group consisting of nitrogen, oxygen and sulfur heteroatoms, and which are fused to an aryl group, said heterocyclic group or aryl group being unsubstituted or being substituted by at least one substituent selected from the group consisting of substituents (c), defined below;
cycloalkyl groups which have from 3 to 8 carbon atoms and which are unsubstituted or which are substituted by at least one substituent selected from the group consisting of substituents (c), defined below;
cycloalkenyl groups which have from 5 to 8 carbon atoms and which are unsubstituted or which are substituted by at least one substituent selected from the group consisting of substituents (c), defined below;
cycloalkyl groups which have from 3 to 8 carbon atoms and are fused to an aryl group which has from 6 to 10 ring carbon atoms and which are unsubstituted or which are substituted by at least one substituent selected from the group consisting of substituents (c), defined below;

substituents (a)

hydroxy groups;
alkoxy groups which have from 1 to 20 carbon atoms and which are unsubstituted or are substituted by at least one substituent selected from the group consisting of alkoxy groups having from 1 to 4 carbon atoms and alkylthio groups having from 1 to 4 carbon atoms;

aryl groups which have from 6 to 14 ring atoms and which are unsubstituted or which are substituted by at least one substituent selected from the group consisting of substituents (b), defined below;

aryloxy groups which have from 6 to 10 ring atoms and which are unsubstituted or which are substituted by at least one substituent selected from the group consisting of substituents (b), defined below;

aliphatic carboxylic acyloxy groups having from 1 to 20 carbon atoms;

aliphatic carboxylic acylthio groups having from 1 to 20 carbon atoms;

aromatic carboxylic acyloxy groups in which the aryl part has from 6 to 10 ring carbon atoms and is unsubstituted or is substituted by at least one substituent selected from the group consisting of substituents (b), defined below;

groups of formula —NR$^4$R$^5$, —CONHR$^4$R$^5$ and —OCONHR$^4$R$^5$, where R$^4$ and R$^5$ are independently selected from the group consisting of:

hydrogen atoms; alkyl groups having from 1 to 4 carbon atoms; aliphatic carboxylic acyloxy groups having from 1 to 20 carbon atoms and which are unsubstituted or are substituted by at least one substituent selected from the group consisting of substituents (a) other than said groups of formula —NR$^4$R$^5$, —CONHR$^4$R$^5$ and —OCONHR$^4$R$^5$;

aromatic carboxylic acyloxy groups in which the aryl part has from 6 to 10 ring carbon atoms and is unsubstituted or is substituted by at least one substituent selected from the group consisting of substituents (b), defined below; alkoxycarbonyl groups in which the alkoxy part has from 1 to 20 carbon atoms and which are unsubstituted or are substituted by at least one substituent selected from the group consisting of substituents (a) other than said groups of formula —NR$^4$R$^5$, —CONHR$^4$R$^5$ and —OCONHR$^4$R$^5$; alkylthio groups which have from 1 to 4 carbon atoms and which unsubstituted or are substituted by at least one substituent selected from the group consisting of substituents (a) other than said alkylthio groups;

and aryloxycarbonyl groups in which the aryl part has from 6 to 10 ring carbon atoms and is unsubstituted or is substituted by at least one substituent selected from the group consisting of substituents (b), defined below;

carboxy groups;

alkoxycarbonyl groups in which the alkoxy part has from 1 to 20 carbon atoms;

aryloxycarbonyl groups in which the aryl part has from 6 to 10 ring carbon atoms and is unsubstituted or is substituted by at least one substituent selected from the group consisting of substituents (b), defined below;

mercapto groups;

alkylthio groups having from 1 to 20 carbon atoms;

arylthio groups in which the aryl part has from 6 to 10 ring carbon atoms and is unsubstituted or is substituted by at least one substituent selected from the group consisting of substituents (b), defined below;

aralkylthio groups in which the aryl part has from 6 to 10 ring carbon atoms and is unsubstituted or is substituted by at least one substituent selected from the group consisting of substituents (b), defined below, and the alkyl part has from 1 to 4 carbon atoms;

aralkyldithio groups in which the aryl part has from 6 to 10 ring carbon atoms and is unsubstituted or is substituted by at least one substituent selected from the group consisting of substituents (b), defined below, and the alkyl part has from 1 to 4 carbon atoms;

aryldithio groups in which the aryl part has from 6 to 10 ring carbon atoms and is unsubstituted or is substituted by at least one substituent selected from the group consisting of substituents (b), defined below;

alkyldithio groups which have from 1 to 20 carbon atoms;

alkylsulfinyl groups which have from 1 to 20 carbon atoms;

arylsulfinyl groups in which the aryl part has from 6 to 10 ring carbon atoms and is unsubstituted or is substituted by at least one substituent selected from the group consisting of substituents (b), defined below;

alkylsulfonyl groups which have from 1 to 20 carbon atoms;

arylsulfonyl groups in which the aryl part has from 6 to 10 ring carbon atoms and is unsubstituted or is substituted by at least one substituent selected from the group consisting of substituents (b), defined below;

cyano groups;

aliphatic carboxylic acyl groups having from 1 to 20 carbon atoms;

aromatic carboxylic acyl groups in which the aryl part has from 6 to 10 ring carbon atoms and is unsubstituted or is substituted by at least one substituent selected from the group consisting of substituents (b), defined below;

cycloalkyl groups having from 3 to 8 ring atoms, and which are unsubstituted or are substituted by at least one substituent selected from the group consisting of alkyl groups having from 1 to 4 carbon atoms;

cycloalkenyl groups having from 5 to 8 ring atoms, and which are unsubstituted or are substituted by at least one substituent selected from the group consisting of alkyl groups having from 1 to 4 carbon atoms;

tri-substituted silyl groups in which the substituents are independently selected from the group consisting of alkyl groups having from 1 to 6 carbon atoms and aryl groups having from 6 to 10 carbon atoms;

heterocyclic groups which have 5 or 6 ring atoms, of which from 1 to 3 are selected from the group consisting of nitrogen, oxygen and sulfur hetero-atoms, said heterocyclic group being unsubstituted or being substituted by at least one substituent selected from the group consisting of substituents (c), defined below; and halogen atoms;

substituents (b)

alkyl groups having from 1 to 8 carbon atoms;

hydroxy groups;

alkoxy groups having from 1 to 20 carbon atoms;

aryl groups which have from 6 to 10 ring atoms and which are unsubstituted or which are substituted by at least one substituent selected from the group consisting of substituents (b), defined here, provided that, where substituent (b) is an aryl group, it is not substituted by a further group which is or contains an aryl group;

aryloxy groups which have from 6 to 10 ring atoms and which are unsubstituted or which are substituted by at least one substituent selected from the group consisting of substituents (b), defined here, provided that, where substituent (b) is an aryloxy group, it is not substituted by a further group which is or contains an aryl group;

aliphatic carboxylic acyloxy groups having from 1 to 20 carbon atoms;

aromatic carboxylic acyloxy groups in which the aryl part has from 6 to 10 ring carbon atoms and is unsubstituted or is substituted by at least one substituent selected from the group consisting of substituents (b), defined here, provided that, where substituent (b) is an aromatic carboxylic acyloxy group, it is not substituted by a further group which is or contains an aryl group;

groups of formula —$NR^4R^5$, —$CONHR^4R^5$ and —$OCONHR^4R^5$, where $R^4$ and $R^5$ are as defined above;

carboxy groups;

alkoxycarbonyl groups in which the alkoxy part has from 1 to 20 carbon atoms;

aryloxycarbonyl groups in which the aryl part has from 6 to 10 ring carbon atoms and is unsubstituted or is substituted by at least one substituent selected from the group consisting of substituents (b), defined here, provided that, where substituent (b) is an aryloxycarbonyl group, it is not substituted by a further group which is or contains an aryl group;

mercapto groups;

alkylthio groups having from 1 to 20 carbon atoms;

arylthio groups in which the aryl part has from 6 to 10 ring carbon atoms and is unsubstituted or is substituted by at least one substituent selected from the group consisting of substituents (b), defined here, provided that, where substituent (b) is an arylthio group, it is not substituted by a further group which is or contains an aryl group;

aralkylthio groups in which the aryl part has from 6 to 10 ring carbon atoms and is unsubstituted or is substituted by at least one substituent selected from the group consisting of substituents (b), defined here, provided that, where substituent (b) is an aralkylthio group, it is not substituted by a further group which is or contains an aryl group, and the alkyl part has from 1 to 4 carbon atoms;

aralkyldithio groups in which the aryl part has from 6 to 10 ring carbon atoms and is unsubstituted or is substituted by at least one substituent selected from the group consisting of substituents (b), defined here, provided that, where substituent (b) is an aralkyldithio group, it is not substituted by a further group which is or contains an aryl group, and the alkyl part has from 1 to 4 carbon atoms;

aryldithio groups in which the aryl part has from 6 to 10 ring carbon atoms and is unsubstituted or is substituted by at least one substituent selected from the group consisting of substituents (b), defined here, provided that, where substituent (b) is an aryldithio group, it is not substituted by a further group which is or contains an aryl group;

alkyldithio groups which have from 1 to 20 carbon atoms;

alkylsulfinyl groups which have from 1 to 20 carbon atoms;

arylsulfinyl groups in which the aryl part has from 6 to 10 ring carbon atoms and is unsubstituted or is substituted by at least one substituent selected from the group consisting of substituents (b), defined here, provided that, where substituent (b) is an arylsulfinyl group, it is not substituted by a further group which is or contains an aryl group;

alkylsulfonyl groups which have from 1 to 20 carbon atoms;

arylsulfonyl groups in which the aryl part has from 6 to 10 ring carbon atoms and is unsubstituted or is substituted by at least one substituent selected from the group consisting of substituents (b), defined here, provided that, where substituent (b) is an arylsulfinyl group, it is not substituted by a further group which is or contains an aryl group, and the alkyl part has from 1 to 4 carbon atoms;

cyano groups;

aliphatic carboxylic acyl groups having from 1 to 20 carbon atoms;

aromatic carboxylic acyl groups in which the aryl part has from 6 to 10 ring carbon atoms and is unsubstituted or is substituted by at least one substituent selected from the group consisting of substituents (b), defined here, provided that, where substituent (b) is an aromatic carboxylic acyl group, it is not substituted by a further group which is or contains an aryl group;

heterocyclic groups which have 5 or 6 ring atoms, of which from 1 to 3 are selected from the group consisting of nitrogen, oxygen and sulfur hetero-atoms, said heterocyclic group being unsubstituted or being substituted by at least one substituent selected from the group consisting of substituents (c), defined below; and halogen atoms;

substituents (c)

oxygen atoms (to form an oxo group);

alkyl groups having from 1 to 8 carbon atoms;

hydroxy groups;

alkoxy groups having from 1 to 20 carbon atoms;

aryl groups which have from 6 to 10 ring atoms and which are unsubstituted or which are substituted by at least one substituent selected from the group consisting of substituents (b), defined above;

aryloxy groups which have from 6 to 10 ring atoms and which are unsubstituted or which are substituted by at least one substituent selected from the group consisting of substituents (b), defined above;

aliphatic carboxylic acyloxy groups having from 1 to 20 carbon atoms;

aromatic carboxylic acyloxy groups in which the aryl part has from 6 to 10 ring carbon atoms and is unsubstituted or is substituted by at least one substituent selected from the group consisting of substituents (b), defined above;

groups of formula —$NR^4R^5$, —$CONHR^4R^5$ and —$OCONHR^4R^5$, where $R^4$ and $R^5$ are as defined above;

carboxy groups;

alkoxycarbonyl groups in which the alkoxy part has from 1 to 20 carbon atoms;

aryloxycarbonyl groups in which the aryl part has from 6 to 10 ring carbon atoms and is unsubstituted or is substituted by at least one substituent selected from the group consisting of substituents (b), defined above;

mercapto groups;

alkylthio groups having from 1 to 20 carbon atoms;

arylthio groups in which the aryl part has from 6 to 10 ring carbon atoms and is unsubstituted or is substituted by at least one substituent selected from the group consisting of substituents (b), defined above;

aralkylthio groups in which the aryl part has from 6 to 10 ring carbon atoms and is unsubstituted or is substituted by at least one substituent selected from the group consisting of substituents (b), defined above, and the alkyl part has from 1 to 4 carbon atoms;

aralkyldithio groups in which the aryl part has from 6 to 10 ring carbon atoms and is unsubstituted or is substituted by at least one substituent selected from the group consisting of substituents (b), defined above, and the alkyl part has from 1 to 4 carbon atoms;

aryldithio groups in which the aryl part has from 6 to 10 ring carbon atoms and is unsubstituted or is substituted by at least one substituent selected from the group consisting of substituents (b), defined above;

alkyldithio groups which have from 1 to 20 carbon atoms;

alkylsulfinyl groups which have from 1 to 20 carbon atoms;

arylsulfinyl groups in which the aryl part has from 6 to 10 ring carbon atoms and is unsubstituted or is substituted by at least one substituent selected from the group consisting of substituents (b), defined above;

alkylsulfonyl groups which have from 1 to 20 carbon atoms;

arylsulfonyl groups in which the aryl part has from 6 to 10 ring carbon atoms and is unsubstituted or is substituted by at least one substituent selected from the group consisting of substituents (b), defined above, and the alkyl part has from 1 to 4 carbon atoms;

cyano groups;

aliphatic carboxylic acyl groups having from 1 to 20 carbon atoms;

aromatic carboxylic acyl groups in which the aryl part has from 6 to 10 ring carbon atoms and is unsubstituted or is substituted by at least one substituent selected from the group consisting of substituents (b), defined above;

heterocyclic groups which have 5 or 6 ring atoms, of which from 1 to 3 are selected from the group consisting of nitrogen, oxygen and sulfur hetero-atoms, said heterocyclic group being unsubstituted or being substituted by at least one substituent selected from the group consisting of substituents (c), defined here, provided that, where substituent (c) is a heterocyclic group, it is not substituted by a further heterocyclic group; and halogen atoms;

PROVIDED THAT $R^1$ and $R^2$ do not both represent hydrogen atoms AND THAT $R^1$ and $R^2$ do not both represent acetyl groups;

and pharmaceutically acceptable salts thereof.

The invention also provides a pharmaceutical composition for the treatment or prophylaxis of tumors, which comprises an effective amount of an active compound in admixture with a pharmaceutically acceptable carrier or diluent, wherein said active compound is selected from the group consisting of compounds of formula (I) and salts thereof, as defined above.

The invention also provides a method for the treatment or prophylaxis of tumors, which comprises administering to an animal, e.g. a mammal, which may be human, an effective amount of an active compound, wherein said active compound is selected from the group consisting of compounds of formula (I) and salts thereof, as defined above.

The invention also provides various processes for preparing the compounds of the present invention, which are described in greater detail hereafter.

DETAILED DESCRIPTION OF INVENTION

In the compounds of the present invention, where $R^3$ represents an alkyl group, this has from 1 to 50 carbon atoms, and may be a straight or branched chain group. Examples of such groups include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups. Certain of the acylated radicicol derivatives of the present invention may not be easily soluble in the most common physiologically acceptable solvents, and in such cases (which most notably include the derivatives of the longer chain aliphatic acids), a special solvent system may be employed to solubilize the compound, as is well known in the art and can readily be determined by the man skilled in the art. However, to avoid the need for this, shorter chain alkyl groups among those represented by $R^3$ are preferred, for example those alkyl groups having from 1 to 25 carbon atoms, more preferably from 8 to 20 carbon atoms, and most preferably from 12 to 17 carbon atoms (i.e. the alkanoyl group represented by $R^1$ or $R^2$ would have from 2 to 26, more preferably from 9 to 21 and most preferably from 13 to 18, carbon atoms).

Where $R^3$ represents a substituted alkyl group, this may be any of those groups listed above, which is substituted by at least one of substituents (a), defined above and exemplified below.

In relation to these, and all substituted groups where a specific number of substituents is not given, there is no particular restriction on the number of such groups, except as may be required by the number of substitutable atoms, or possibly by steric constraints. In general, however, we prefer (provided there are sufficient subtitutable atoms) from 1 to 5 substituents, more preferably from 1 to 3 substituents.

Among substituents (a), are included aryl groups, which may be as defined above and exemplified below. Such substituted groups are aralkyl groups, and these preferably have from 1 to 4 carbon atoms in the alkyl part and from 1 to 10 carbon atoms in the aryl part. The aryl part may be substituted or unsubstituted. Examples of such aralkyl groups include the benzyl, phenethyl, 1-phenylethyl, 1-, 2- and 3-phenylpropyl, 1-, 2-, 3-, 4- and 5-phenylpentyl and the 1- and 2-naphthylmethyl groups.

Where $R^3$ represents an alkoxy group, this has from 1 to 20 carbon atoms, and may be a straight or branched chain group. Examples of such groups include the methoxy, ethoxy, propoxy, isopropoxy, butoxy, isobutoxy, sec-butoxy, t-butoxy, pentoxy, 3-methylbutoxy, 2,2-dimethylpropoxy, 1,1-dimethylpropoxy, hexyloxy, 1-methylpentyloxy, 4-methylpentyloxy, heptyloxy, 1-methylhexyloxy, 2-methylhexyloxy, 5-methylhexyloxy, 3-ethylpentyloxy, octyloxy, 2-methylheptyloxy, 6-methylheptyloxy, 2-ethylhexyloxy, 2-ethyl-3-methylpentyloxy, 3-ethyl-2-methylpentyloxy, nonyloxy, 2-methyloctyloxy, 7-methyloctyloxy, 4-ethylheptyloxy, 3-ethyl-2-methylhexyloxy, 2-ethyl-1-methylhexyloxy, decyloxy, 2-methylnonyloxy, 8-methylnonyloxy, 5-ethyloctyloxy, 3-ethyl-2-methylheptyloxy, 3,3-diethylhexyloxy, undecyloxy, 2-methyldecyloxy, 9-methyldecyloxy, 4-ethylnonyloxy, 3,5-dimethylnonyloxy, 3-propyloctyloxy, 5-ethyl-4-methyloctyloxy, 1-pentylhexyloxy, dodecyloxy, 1-methylundecyloxy, 10-methylundecyloxy, 3-ethyldecyloxy, 5-propylnonyloxy, 3,5-diethyloctyloxy, tridecyloxy, 11-methyldodecyloxy, 7-ethylundecyloxy, 4-propyldecyloxy, 5-ethyl-3-methyldecyloxy, 3-pentyloctyloxy, tetradecyloxy, 12-methyltridecyloxy, 8-ethyldodecyloxy, 6-propylundecyloxy, 4-butyldecyloxy, 2-pentylnonyloxy, pentadecyloxy, 13-methyltetradecyloxy, 10-ethyltridecyloxy, 7-propyldodecyloxy, 5-ethyl-3-methyldodecyloxy, 4-pentyldecyloxy, 1-hexylnonyloxy, hexadecyloxy, 14-methylpentadecyloxy, 6-ethyltetradecyloxy, 4-propyltridecyloxy, 2-butyldodecyloxy, heptadecyloxy, 15-methylhexadecyloxy, 7-ethylpentadecyloxy, 3-propyltetradecyloxy, 5-pentyldodecyloxy, octadecyloxy, 16-methylheptadecyloxy, 5-propylpentadecyloxy, nonadecyloxy, 17-methyloctadecyloxy, 4-ethylheptadecyloxy, icosyloxy and 18-methylnonadecyloxy, 3-ethyloctadecyloxy groups.

Where $R^3$ represents a substituted alkoxy group, this may be any of those groups listed above, which is substituted by at least one of substituents (a), defined above and exemplified below.

Where $R^3$ represents an alkenyl group, this has from 2 to 30 carbon atoms, and may be a straight or branched chain group. It may have 1 or more, preferably from 1 to 4, double bonds. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl groups.

Where $R^3$ represents a substituted alkenyl group, this may be any of those groups listed above, which is substituted by at least one of substituents (a), defined above and exemplified below.

Where $R^3$ represents an alkynyl group, this has from 2 to 10 carbon atoms, and may be a straight or branched chain group. Examples of such groups include the ethynyl, 1-propynyl, propargyl, 1-heptynyl, 1-octynyl and 1-decynyl groups.

Where $R^3$ represents a substituted alkynyl group, this may be any of those groups listed above, which is substituted by at least one of substituents (a), defined above and exemplified below.

Where $R^3$ represents an aryl group, this has from 6 to 14 ring atoms, in a single or multiple rings, and examples include the phenyl, 1-naphthyl, 2-naphthyl, fluorenyl, 1-anthryl and 1-phenanthryl groups. Such groups may be substituted or unsubstituted, and, if substituted, the substituents are selected from the group consisting of substituents (a), defined above and exemplified below.

Where $R^3$ represents an aryloxy group, this has from 6 to 14 ring atoms, in a single or multiple rings, and examples include the phenoxy, 1-naphthyloxy, 2-naphthyloxy, fluorenyloxy, 1-anthryloxy and 1-phenanthryloxy groups. Such groups may be substituted or unsubstituted, and, if substituted, the substituents are selected from the group consisting of substituents (a), defined above and exemplified below.

Where $R^3$ represents a heterocyclic group, this has 5 or 6 ring atoms. Of these atoms, from 1 to 3 are hetero-atoms selected from the group consisting of nitrogen, oxygen and sulfur hetero-atoms. Where there are 3 hetero-atoms, we prefer that at least one (more preferably 2) should be a nitrogen atom and one or two should be nitrogen, oxygen or sulfur atoms (and, where there are two, they may be the same or different). Where there are two hetero-atoms, these may be the same or different and they are selected from nitrogen, oxygen and sulfur atoms; however, more preferably one is a nitrogen atom and the other is a nitrogen, oxygen or sulfur atom. Such groups may be unsubstituted or they may be substituted by at least one (preferably from 1 to 3) of substituents (c), defined and exemplified above. Examples of such unsubstituted groups include the furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, tetrahydrofuranyl, tetrahydrothienyl, pyrrolidinyl, thiazolidinyl, thiazolinyl, isothiazolinyl, imidazolidinyl, imidazolinyl, oxazolinyl, isoxazolinyl, oxazolidinyl, pyrazolidinyl, piperazinyl, dioxopiperazinyl, tetrahydropyrimidinyl, dihydropyridazinyl, morpholinyl, thiomorpholinyl, pyrrolidonyl, piperidonyl, pyridonyl, 2H-pyrrolyl, furazanyl and pyrazolinyl groups, especially the furyl, pyrrolyl, pyridyl, thiazolyl, isothiazolyl, oxazolyl, isoxazolyl, imidazolyl, pyridazinyl, pyrrolidinyl, thiazolinyl, isothiazolinyl, imidazolyl, piperazinyl, dioxopiperazinyl, morpholinyl, pyrrolidonyl and piperidonyl groups. Such groups may be unsubstituted or they may have at least one substituent selected from the group consisting of substituents (c), defined above and exemplified below.

Where $R^3$ represents a cycloalkyl group, this has from 3 to 8 carbon atoms and may be unsubstituted or substituted. If it is substituted, it has at least one substituent selected from the group consisting of substituents (c), defined above and exemplified below. Examples of such groups include the cyclopropyl, cyclobutyl, cyclopentyl, cyclohexyl, cyclopentyl and cyclooctyl groups and substituted analogs thereof.

Where $R^3$ represents a cycloalkenyl group, this has from 5 to 8 carbon atoms and may be unsubstituted or substituted. If it is substituted, it has at least one substituent selected from the group consisting of substituents (c), defined above and exemplified below. It has one or more, preferably 1 or 2, more preferably 1, carbon-carbon double bond. Examples of such groups include the 1-cyclopenten-1-yl, 2-cyclopenten-1-yl, 1-cyclohexen-1-yl, 2-cyclohexen-1-yl, 3-cyclohexen-1-yl, 1-cylohepten-1-yl, 2-cyclohepten-1-yl, 1-cycloocten-1-yl and 3-cycloocten-1-yl groups and substituted analogs thereof.

Where $R^3$ represents a cycloalkyl group fused to an aryl group, the cycloalkyl part has from 3 to 8 carbon atoms and the aryl part has from 6 to 10 carbon atoms (and is preferably a benzene ring). The group may be unsubstituted or substituted. If it is substituted, it has at least one substituent selected from the group consisting of substituents (c), defined above and exemplified below. Examples of such groups include the indanyl and tetrahydronaphthyl groups.

Examples of groups and atoms which may be included in substituents (a) include:

1. hydroxy groups;
2. alkoxy groups which have from 1 to 20 carbon atoms and which are unsubstituted or are substituted by at least one substituent selected from the group consisting of alkoxy groups having from 1 to 4 carbon atoms, such as the methoxy, ethoxy, propoxy, isopropoxy, butoxy, isobutoxy, sec-butoxy, t-butoxy, pentyloxy, methoxymethoxy, 1-methoxyethoxy, 2-methoxyethoxy, butoxymethoxy, 2-butoxyethoxy, 3-ethoxypropoxy, 3-methylbutoxy, 2,2-dimethylpropoxy, 1,1-dimethylpropoxy, hexyloxy, 1-methylpentyloxy, 4-methylpentyloxy, heptyloxy, 1-methylhexyloxy, 2-methylhexyloxy, 5-methylhexyloxy, 3-ethylpentyloxy, octyloxy, 2-methylheptyloxy, 6-methylheptyloxy, 2-ethylhexyloxy, 2-ethyl-3-methylpentyloxy, 3-ethyl-2-methylpentyloxy, nonyloxy, 2-methyloctyloxy, 7-methyloctyloxy, 4-ethylheptyloxy, 3-ethyl-2-methylhexyloxy, 2-ethyl-1-methylhexyloxy, decyloxy, 2-methylnonyloxy, 8-methylnonyloxy, 5-ethyloctyloxy, 3-ethyl-2-methylheptyloxy, 3,3-diethylhexyloxy, undecyloxy, 2-methyldecyloxy, 9-methyldecyloxy, 4-ethylnonyloxy, 3,5-dimethylnonyloxy, 3-propyloctyloxy, 5-ethyl-4-methyloctyloxy, 1-pentylhexyloxy, dodecyloxy, 1-methylundecyloxy, 10-methylundecyloxy, 3-ethyldecyloxy, 5-propylnonyloxy, 3,5-diethyloctyloxy, tridecyloxy, 11-methyldodecyloxy, 7-ethylundecyloxy, 4-propyldecyloxy, 5-ethyl-3-methyldecyloxy, 3-pentyloctyloxy, tetradecyloxy, 12-methyltridecyloxy, 8-ethyldodecyloxy, 6-propylundecyloxy, 4-butyldecyloxy, 2-pentylnonyloxy, pentadecyloxy, 13-methyltetradecyloxy, 10-ethyltridecyloxy, 7-propyldodecyloxy, 5-ethyl-3-methyldodecyloxy, 4-pentyldecyloxy, 1-hexylnonyloxy, hexadecyloxy, 14-methylpentadecyloxy, 6-ethyltetradecyloxy, 4-propyltridecyloxy, 2-butyldodecyloxy, heptadecyloxy, 15-methylhexadecyloxy, 7-ethylpentadecyloxy, 3-propyltetradecyloxy, 5-pentyldodecyloxy, octadecyloxy, 16-methylheptadecyloxy, 5-propylpentadecyloxy, nonadecyloxy, 17-methyloctadecyloxy, 4-ethylheptadecyloxy, icosyloxy and 18-methylnonadecyloxy, 3-ethyloctadecyloxy groups;
3. aryl groups which have from 6 to 14 ring atoms and which are unsubstituted or which are substituted by at least one substituent selected from the group consisting of substituents (b), defined above and exemplified below, such as the phenyl, 1-naphthyl, 2-naphthyl, fluorenyl, 1-anthryl and 1-phenanthryl groups;
4. aryloxy groups which have from 6 to 10 ring atoms and which are unsubstituted or which are substituted by at least one substituent selected from the group consisting of substituents (b), defined above and exemplified below, such as the phenoxy, 1-naphthyloxy, 2-naphthyloxy, fluorenyloxy, 1-anthryloxy and 1-phenanthryloxy groups;
5. aliphatic carboxylic acyloxy groups having from 1 to 22, preferably from 1 to 20, carbon atoms, such as the formyloxy, acetoxy, propionyloxy, butyryloxy, isobutyryloxy, valeryloxy, isovaleryloxy, pivaloyloxy, hexanoyloxy, 2-methylpentanoyloxy, 2-ethylbutyryloxy, heptanoyloxy, 2-methylhexanoyloxy, 4-methylhexanoyloxy, 2-ethylpentanoyloxy, octanoyloxy, 2-methylheptanoyloxy, 4-methylheptanoyloxy, 2-ethylhexanoyloxy, nonanoyloxy, 2-methyloctanoyloxy, 5-methyloctanoyloxy, 2-ethylheptanoyloxy, nonylcarbonyloxy, decylcarbonyloxy, 3-methylnonylcarbonyloxy, 8-methylnonylcarbonyloxy, 3-ethyloctylcarbonyloxy, 3,7-dimethyloctylcarbonyloxy, undecylcarbonyloxy, dodecylcarbonyloxy, tridecylcarbonyloxy, tetradecylcarbonyloxy, pentadecylcarbonyloxy, hexadecylcarbonyloxy, 1-methylpentadecylcarbonyloxy, 14-methylpentadecylcarbonyloxy, 13,13-dimethyltetradecylcarbonyloxy, heptadecylcarbonyloxy, 15-methylhexadecylcarbonyloxy, octadecylcarbonyloxy, 1-methylheptadecylcarbonyloxy, nonadecylcarbonyloxy, icosylcarbonyloxy and henicosylcarbonyloxy groups;
6. aliphatic carboxylic acylthio groups having from 1 to 22, preferably from 1 to 20, carbon atoms, such as the formylthio, acetylthio, propionylthio, butyrylthio, isobutyrylthio, valerylthio, isovalerylthio, pivaloylthio, hexanoylthio, 2-methylpentanoylthio, 2-ethylbutyrylthio, heptanoylthio, 2-methylhexanoylthio, 4-methylhexanoylthio, 2-ethylpentanoylthio, octanoylthio, 2-methylheptanoylthio, 4-methylheptanoylthio, 2-ethylhexanoylthio, nonanoylthio, 2-methyloctanoylthio, 5-methyloctanoylthio, 2-ethylheptanoylthio, nonylcarbonylthio, decylcarbonylthio, 3-methylnonylcarbonylthio, 8-methylnonylcarbonylthio, 3-ethyloctylcarbonylthio, 3,7-dimethyloctylcarbonylthio, undecylcarbonylthio, dodecylcarbonylthio, tridecylcarbonylthio, tetradecylcarbonylthio, pentadecylcarbonylthio, hexadecylcarbonylthio, 1-methylpentadecylcarbonylthio, 14-methylpentadecylcarbonylthio, 13,13-dimethyltetradecylcarbonylthio, heptadecylcarbonylthio, 15-methylhexadecylcarbonylthio, octadecylcarbonylthio, 1-methylheptadecylcarbonylthio, nonadecylcarbonylthio, icosylcarbonylthio and henicosylcarbonylthio groups; such groups may be substituted or unsubstituted, and, if substituted, the substituents are selected from the group consisting of substituents (a), provided that any such substituent is not further substituted by a group which is or contains such an aliphatic carboxylic acyl group;
7. aromatic carboxylic acyloxy groups in which the aryl part has from 6 to 10 ring carbon atoms and is unsubstituted or is substituted by at least one substituent selected from the group consisting of substituents (b), defined above and exemplified below; examples include the benzoyl and naphthoyl groups and substituted analogs thereof;
8. groups of formula $-NR^4R^5$, $-CONHR^4R^5$ and $-OCONHR^4R^5$, where $R^4$ and $R^5$ are independently selected from the group consisting of:
hydrogen atoms; alkyl groups having from 1 to 4 carbon atoms (e.g. the methyl, ethyl, propyl, isopropyl, butyl, isobutyl, sec-butyl and t-butyl groups); aliphatic carboxylic acyloxy groups having from 1 to 20 carbon atoms and which are unsubstituted or are substituted by at least one substituent selected from the group consisting of substituents (a) other than said groups of formula $-NR^4R^5$, $-CONHR^4R^5$ and $-OCONHR^4R^5$ (e.g. as exemplified above); aromatic carboxylic acyloxy groups in which the aryl part has from 6 to 10 ring carbon atoms and is unsubstituted or is substituted by at least one substituent selected from the group consisting of substituents (b), defined above and exemplified below (e.g. as exemplified above); alkoxycarbonyl groups in which the alkoxy part has from 1 to 20 carbon atoms and which are unsubstituted or are substituted by at least one substituent selected from the group consisting of substituents (a) other than said groups of formula —$NR^4R^5$, —$CONHR^4R^5$ and —$OCONHR^4R^5$ (e.g. those in which the alkoxy part is as exemplified above); alkylthio groups which have from 1 to 4 carbon atoms and which are unsubstituted or are substituted by at least one substituent selected from the group consisting of substituents (a) other than said alkylthio groups (e.g. the methylthio, ethylthio, propylthio, isopropylthio, butylthio, isobutylthio, sec-butylthio and t-butylthio groups); and aryloxycarbonyl groups in which the aryl part has from 6 to 10 ring carbon atoms and is unsubstituted or is substituted by at least one substituent selected from the group consisting of substituents (b), defined below (e.g. the benzoyl and naphthoyl groups and substituted analogs thereof);

9. carboxy groups;

10. alkoxycarbonyl groups in which the alkoxy part has from 1 to 20 carbon atoms, such as those groups in which the alkoxy part is as exemplified above;

11. aryloxycarbonyl groups in which the aryl part has from 6 to 10 ring carbon atoms and is unsubstituted or is substituted by at least one substituent selected from the group consisting of substituents (b), defined below, such as those groups in which the aryloxy part is as exemplified above;

12. mercapto groups;

13. alkylthio groups having from 1 to 20 carbon atoms, such as the methylthio, ethylthio, propylthio, isopropylthio, butylthio, isobutylthio, sec-butylthio, t-butylthio, pentylthio, 3-methylbutylthio, 2,2-dimethylpropylthio, 1,1-dimethylpropylthio, hexylthio, 1-methylpentylthio, 4-methylpentylthio, heptylthio, 1-methylhexylthio, 2-methylhexylthio, 5-methylhexylthio, 3-ethylpentylthio, octylthio, 2-methylheptylthio, 6-methylheptylthio, 2-ethylhexylthio, 2-ethyl-3-methylpentylthio, 3-ethyl-2-methylpentylthio, nonylthio, 2-methyloctylthio, 7-methyloctylthio, 4-ethylheptylthio, 3-ethyl-2-methylhexylthio, 2-ethyl-1-methylhexylthio, decylthio, 2-methylnonylthio, 8-methylnonylthio, 5-ethyloctylthio, 3-ethyl-2-methylheptylthio, 3,3-diethylhexylthio, undecylthio, 2-methyldecylthio, 9-methyldecylylthio, 4-ethylnonylthio, 3,5-dimethylnonylthio, 3-propyloctylthio, 5-ethyl-4-methyloctylthio, 1-pentylhexylthio, dodecylthio, 1-methylundecylthio, 10-methylundecylthio, 3-ethyldecylthio, 5-propylnonylthio, 3,5-diethyloctylthio, tridecylthio, 11-methyldodecylthio, 7-ethylundecylthio, 4-propyldecylthio, 5-ethyl-3-methyldecylthio, 3-pentyloctylthio, tetradecylthio, 12-methyltridecylthio, 8-ethyldodecylthio, 6-propylundecylthio, 4-butyldecylthio, 2-pentylnonylthio, pentadecylthio, 13-methyltetradecylthio, 10-ethyltridecylthio, 7-propyldodecylthio, 5-ethyl-3-methyldodecylthio, 4-pentyldecylthio, 1-hexylnonylthio, hexadecylthio, 14-methylpentadecylthio, 6-ethyltetradecylthio, 4-propyltridecylthio, 2-butyldodecylthio, heptadecylthio, 15-methylhexadecylthio, 7-ethylpentadecylthio, 3-propyltetradecylthio, 5-pentyldodecylthio, octadecylthio, 16-methylheptadecylthio, 5-propylpentadecylthio, nonadecylthio, 17-methyloctadecylthio, 4-ethylheptadecylthio, icosylthio, 18-methylnonadecylthio and 3-ethyloctadecylthio groups;

14. arylthio groups in which the aryl part has from 6 to 10 ring carbon atoms and is unsubstituted or is substituted by at least one substituent selected from the group consisting of substituents (b), defined above and exemplified below (such as the phenylthio and naphthylthio groups and substituted analogs thereof);

15. aralkylthio groups in which the aryl part has from 6 to 10 ring carbon atoms and is unsubstituted or is substituted by at least one substituent selected from the group consisting of substituents (b), defined below, and the alkyl part has from 1 to 4 carbon atoms, such as the benzylthio, phenethylthio, 1-phenylethylthio, 1-, 2- and 3-phenylpropylthio, 1-, 2-, 3-, 4- and 5-phenylpentylthio and the 1- and 2-naphthylmethylthio groups;

16. aralkyldithio groups in which the aryl part has from 6 to 10 ring carbon atoms and is unsubstituted or is substituted by at least one substituent selected from the group consisting of substituents (b), defined below, and the alkyl part has from 1 to 4 carbon atoms, such as the benzyldithio, phenethyldithio, 1-phenylethyldithio, 1-, 2- and 3-phenylpropyldithio, 1-, 2-, 3-, 4- and 5-phenylpentyldithio and the 1- and 2-naphthylmethyldithio groups;

17. aryldithio groups in which the aryl part has from 6 to 10 ring carbon atoms and is unsubstituted or is substituted by at least one substituent selected from the group consisting of substituents (b), defined above and exemplified below (such as the phenyldithio and naphthyldithio groups and substituted analogs thereof);

18. alkyldithio groups which have from 1 to 20 carbon atoms, such as the dithio analogs of the alkylthio groups exemplified above;

19. alkylsulfinyl groups which have from 1 to 20 carbon atoms, such as the sulfinyl analogs of the alkylthio groups exemplified above;

20. arylsulfinyl groups in which the aryl part has from 6 to 10 ring carbon atoms and is unsubstituted or is substituted by at least one substituent selected from the group consisting of substituents (b), defined above and exemplified below, such as the sulfinyl analogs of the arylthio groups exemplified above;

21. alkylsulfonyl groups which have from 1 to 20 carbon atoms, such as the sulfonyl analogs of the alkylthio groups exemplified above;

22. arylsulfonyl groups in which the aryl part has from 6 to 10 ring carbon atoms and is unsubstituted or is substituted by at least one substituent selected from the group consisting of substituents (b), defined below, such as the sulfonyl analogs of the arylthio groups exemplified above;

23. cyano groups;

24. aliphatic carboxylic acyl groups having from 1 to 20 carbon atoms, such as the formyl, acetyl, propionyl, butyryl, isobutyryl, valeryl, isovaleryl, pivaloyl, hexanoyl, 2-methylpentanoyl, 2-ethylbutyryl, heptanoyl, 2-methylhexanoyl, 4-methylhexanoyl, 2-ethylpentanoyl, octanoyl, 2-methylheptanoyl, 4-methylheptanoyl, 2-ethylhexanoyl, nonanoyl, 2-methyloctanoyl, 5-methyloctanoyl, 2-ethylheptanoyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, icosylcarbonyl and henicosylcarbonyl groups;
25. aromatic carboxylic acyl groups in which the aryl part has from 6 to 10 ring carbon atoms and is unsubstituted or is substituted by at least one substituent selected from the group consisting of substituents (b), defined above and exemplified below, such as the benzoyl and naphthoyl groups and substituted analogs thereof;
26. cycloalkyl groups having from 3 to 8 ring atoms, and which are unsubstituted or are substituted by at least one substituent selected from the group consisting of alkyl groups having from 1 to 4 carbon atoms, such as the cyclopropyl, cyclobutyl, cyclopentyl, cyclohexyl, cyclopentyl and cyclooctyl groups and substituted analogs thereof, especially the unsubstituted groups and those having at least one methyl substituent;
27. cycloalkenyl groups having from 5 to 8 ring atoms, and which are unsubstituted or are substituted by at least one substituent selected from the group consisting of alkyl groups having from 1 to 4 carbon atoms, such as the 1-cyclopenten-1-yl, 2-cyclopenten-1-yl, 1-cyclohexen-1-yl, 2-cyclohexen-1-yl, 3-cyclohexen-1-yl, 1-cylohepten-1-yl, 2-cyclohepten-1-yl, 1-cycloocten-1-yl and 3-cycloocten-1-yl groups and substituted analogs thereof, especially the unsubstituted groups and those having at least one methyl substituent;
28. tri-substituted silyl groups in which the substituents are independently selected from the group consisting of alkyl groups having from 1 to 6 carbon atoms and aryl groups having from 6 to 10 carbon atoms, preferably in which all three or two or one of the substituents are alkyl groups having from 1 to 5, more preferably from 1 to 4, carbon atoms, and none, one or two of the substituents are aryl groups, as defined above, but preferably phenyl or substituted phenyl groups, preferably: tri(lower alkyl)silyl groups (such as the trimethylsilyl, triethylsilyl, isopropyldimethylsilyl, t-butyl-dimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, diphenylbutyl-silyl, diphenyl-t-butylsilyl, diphenylisopropylsilyl and phenyldiisopropylsilyl groups);
29. heterocyclic groups which have 5 or 6 ring atoms, of which from 1 to 3 are selected from the group consisting of nitrogen, oxygen and sulfur hetero-atoms, said heterocyclic group being unsubstituted or being substituted by at least one substituent selected from the group consisting of substituents (c), defined below, such as those defined above in relation to the groups which may be represented by $R^3$; and
30. halogen atoms, such as the chlorine, fluorine, bromine and iodine atoms.

Examples of the groups and atoms which may be included in substituents (b) include:
alkyl groups having from 1 to 8 carbon atoms, such as the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl and 3-ethyl-2-methylpentyl groups; and
hydroxy, alkoxy, aryl, aryloxy, aliphatic acyloxy, aromatic acyloxy, carboxy, alkoxycarbonyl, aryloxycarbonyl, mercapto, alkylthio, arylthio, aralkylthio, aralkyldithio, aryldithio, alkyldithio, alkylsulfinyl, arylsulfonyl, alkylsulfonyl, arylsulfonyl, cyano, aliphatic and aromatic acyl and heterocyclic groups and groups of formula —$NR^4R^5$, —$CONHR^4R^5$ and —$OCONHR^4R^5$, and halogen atoms, as exemplified in relation to substituents (a).

Substituent (c) may be an oxygen atom, to form an oxo group (>C=O) with the carbon atom to which it is attached, or it may be various other groups and atoms, as exemplified in relation to substituents (a) and (b).

Many of the compounds of the present invention have the anti-tumor activity referred to above. Others may be of value as intermediates in the preparation of other compounds of the present invention, which may have a greater activity.

Preferred classes of compounds of the present invention include those compounds of formula (I) in which $R^1$ and $R^2$ each represents a group of formula $R^3$—CO— and the groups represented by $R^3$ are the same or different and each is selected from the group consisting of:
unsubstituted alkyl groups having from 9 to 20 carbon atoms;
substituted alkyl groups having from 10 to 20 carbon atoms and substituted by at least one substituent selected from the group consisting of substituents (d), defined below;
unsubstituted alkenyl groups having from 9 to 20 carbon atoms;
substituted alkenyl groups having from 10 to 20 carbon atoms and substituted by at least one substituent selected from the group consisting of substituents (d), defined below;
unsubstituted alkynyl groups having from 8 to 10 carbon atoms; and
substituted alkynyl groups having from 8 to 10 carbon atoms and substituted by at least one substituent selected from the group consisting of substituents (d), defined below;
substituents (d):
hydroxy groups, protected hydroxy groups, amino groups, protected amino groups, groups of formula —$NR^6R^7$, where:
$R^6$ and $R^7$ are independently selected from the group consisting of alkyl groups having from 1 to 4 carbon atoms, alkylcarbonyl groups having a total of from 2 to 5 carbon atoms, benzoyl groups, substituted benzoyl groups in which the substituents are selected from the group consisting of substituents (b), defined above, alkoxycarbonyl groups having from 2 to 5 carbon atoms, phenoxycarbonyl groups and substituted phenoxycarbonyl groups in which the substituents are selected from the group consisting of substituents (b), defined above;
carboxy groups, protected carboxy groups, mercapto groups, protected mercapto groups, alkoxy groups having from 1 to 8 carbon atoms, alkylthio groups having 1 or 2 carbon atoms, phenyl groups, substituted phenyl groups in which the substituents are selected from the group consisting of substituents (b), defined above, phenoxy groups, substituted phenoxy groups in which the substituents are selected from the group consisting of substituents (b), defined above, alkylcarbonyloxy groups having from 2 to 9 carbon atoms, benzoyloxy groups, nitro groups, alkoxycarbonyl groups having from 2 to 5 carbon atoms, carbamoyl groups, alkylthio groups having from 1 to 8 carbon atoms, phenylthio groups, alkylthio groups having 1 or 2 carbon atoms and substituted by a phenyl group, alkyldithio groups having 1 or 2 carbon atoms and substituted by a phenyl group, phenyldithio groups, alkyldithio groups having from 1 to 8 carbon atoms, alkylsulfinyl groups having from 1 to 8 carbon atoms, phenylsulfinyl groups, alkylsulfonyl groups having from 1 to 8 carbon atoms, phenylsulfonyl groups, cyano groups, alkylcarbonyl groups having from 2 to 9 carbon atoms, benzoyl groups, carbamoyloxy groups, heterocyclic groups having 5 or 6 ring atoms, of which 1 is a hetero-atom selected from the group consisting of nitrogen, oxygen and sulfur hetero-atoms, and halogen atoms.

More preferred classes of compounds of the present invention include those compounds of formula (I) in which $R^1$ and $R^2$ each represents a group of formula $R^3$—CO— and the groups represented by $R^3$ are the same or different and each is selected from the group consisting of:

unsubstituted alkyl groups having from 9 to 20 carbon atoms;

substituted alkyl groups having from 10 to 20 carbon atoms and substituted by at least one substituent selected from the group consisting of substituents (e), defined below;

unsubstituted alkenyl groups having from 9 to 20 carbon atoms;

substituted alkenyl groups having from 10 to 20 carbon atoms and substituted by at least one substituent selected from the group consisting of substituents (e), defined below;

unsubstituted alkynyl groups having from 8 to 10 carbon atoms; and substituted alkynyl groups having from 8 to 10 carbon atoms and substituted by at least one substituent selected from the group consisting of substituents (e), defined below;

substituents (e):

hydroxy groups, protected hydroxy groups, amino groups, protected amino groups, carboxy groups, protected carboxy groups, mercapto groups, protected mercapto groups, alkoxy groups having from 1 to 8 carbon atoms and alkylthio groups having 1 or 2 carbon atoms.

The most preferred classes of compounds of the present invention include those compounds of formula (I) in which $R^1$ and $R^2$ each represents a group of formula $R^3$—CO— and the groups represented by $R^3$ are the same or different and each is selected from the group consisting of:

unsubstituted alkyl groups having from 9 to 20 carbon atoms; and unsubstituted alkenyl groups having from 9 to 20 carbon atoms.

In any of the compounds of the present invention which contains a hydroxy, amino, mercapto or carboxy group, any of these groups may be protected by a suitable protecting group. Where the protecting group is on a compound intended for use merely as a chemical intermediate, its nature is not critical to the invention and any of the well known protecting groups may be employed. Where the resulting compound is intended for therapeutic use, the protecting group should be pharmaceutically acceptable.

Examples of hydroxy-protecting groups include:

1. aliphatic acyl groups, e.g.: alkylcarbonyl groups preferably having from 1 to 20 carbon atoms, such as the formyl, acetyl, propionyl, butyryl, isobutyryl, pentanoyl, pivaloyl, valeryl, isovaleryl, octanoyl, lauroyl, myristoyl, tridecanoyl, palmitoyl and stearoyl groups; haloalkylcarbonyl groups, especially the haloacetyl groups, such as the chloroacetyl, dichloroacetyl, trichloroacetyl and trifluoroacetyl groups; lower alkoxyalkylcarbonyl groups, especially those having from 3 to 7 carbon atoms, such as the methoxyacetyl group; unsaturated alkylcarbonyl groups, such as the (E)-2-methyl-2-butenoyl group;

2. aromatic acyl groups, especially the arylcarbonyl groups, such as the benzoyl, α-naphthoyl and β-naphthoyl groups; haloarylcarbonyl groups, such as the 2-bromobenzoyl and 4-chlorobenzoyl groups; lower alkylarylcarbonyl groups, especially those in which the alkyl part has from 1 to 4 carbon atoms and the aryl part is a phenyl group, such as the 2,4,6-trimethylbenzoyl and 4-toluoyl groups; lower alkoxyarylcarbonyl groups, especially those in which the alkoxy part has from 1 to 4 carbon atoms and the aryl part is a phenyl group, such as the 4-anisoyl group; nitroarylcarbonyl groups, especially those in which the aryl part is a phenyl group, such as the 4-nitrobenzoyl and 2-nitrobenzoyl groups; lower alkoxycarbonylarylcarbonyl groups, especially those in which the alkoxy part has from 1 to 4 carbon atoms and the aryl part is a phenyl group, such as the 2-(methoxycarbonyl)benzoyl group; arylarylcarbonyl groups, especially those in which each aryl part is an optionally substituted phenyl group, such as the 4-phenylbenzoyl group;

3. tetrahydropyranyl and tetrahydrothiopyranyl groups, such as the tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups;

4. tetrahydrofuranyl and tetrahydrothienyl groups, such as the tetrahydrofuran-2-yl and tetrahydrothien-2-yl groups;

5. silyl groups, especially: tri-lower-alkylsilyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri-lower-alkylsilyl groups in which 1 or 2 of the alkyl groups has been replaced by an aryl groups, such as the diphenylmethylsilyl, diphenylbutylsilyl, diphenylisopropylsilyl and phenyldiisopropylsilyl groups;

6. alkoxymethyl groups, especially lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups; lower alkoxy-lower-alkoxymethyl groups, especially such groups in which each of the alkoxy parts has from 1 to 4 carbon atoms, such as the 2-methoxyethoxymethyl; halogen-substituted lower-alkoxymethyl groups, such as the 2,2,2-trichloroethoxymethyl and bis(2-chloroethoxy)methylgroups;

7. substituted ethyl groups, especially the lower alkoxyethyl groups, such as the 1-ethoxyethyl and 1-(isopropoxy)ethyl groups; haloethyl groups, such as the 2,2,2-trichloroethyl group; arylselenylethyl groups, such as the 2-(phenylselenyl)ethyl group;

8. aralkyl groups, and especially lower (e.g. having from 1 to 4 carbon atoms) alkyl groups which are substituted by from 1 to 3 aryl groups (especially having from 6 to 10 ring atoms), such as the benzyl, α-naphthylmethyl, β-naphthylmethyl, diphenylmethyl, triphenylmethyl, α-naphthyldiphenylmethyl and 9-anthrylmethyl groups; and such groups in which the aryl part is substituted with such substituent(s) as lower alkyl, lower alkoxy, nitro, halogen or cyano group(s), such as the 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl and piperonyl groups;

9. alkoxycarbonyl groups, including: lower alkoxycarbonyl groups, such as the methoxycarbonyl, ethoxycarbonyl, t-butoxycarbonyl and isobutoxycarbonyl groups; lower alkoxycarbonyl group substituted by at least one halogen atom or tri(lower alkyl)silyl group, such as the 2,2,2-trichloroethoxycarbonyl and 2-trimethylsilylethoxycarbonyl groups;

10. alkenyloxycarbonyl groups, such as the vinyloxycarbonyl and allyloxycarbonyl groups;
11. aralkyloxycarbonyl group in which the alkyl part preferably has from 1 to 4 carbon atoms and the aryl part or parts preferably has from 6 to 10 ring carabon atoms and which may optionally have 1 or 2 such substituents as lower alkoxy and/or nitro groups on its aryl ring, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The hydroxy-protecting groups mentioned above are for protection of the hydroxy group during a reaction. In addition to these, there may be mentioned protecting groups which can easily be hydrolyzed in vivo when administered to living body and which may be used for making a pro-drug, such as the pivaloyloxymethoxycarbonyl group.

Examples of amino-protecting group, although equally not particularly limited, include:
1. aliphatic acyl groups, including: alkylcarbonyl groups, such as the formyl, acetyl, propionyl, butyryl, isobutyryl, pentanoyl, pivaloyl, valeryl, isovaleryl, octanoyl, lauroyl, myristoyl, tridecanoyl, palmitoyl and stearoyl groups; haloaliphatic acyl groups, such as the chloroacetyl, dichloroacetyl, trichloroacetyl and trifluoroacetyl groups; lower alkoxyaliphatic acyl groups, such as the methoxyacetyl group; and unsaturated aliphatic acyl groups, such as the (E)-2-methyl-2-butenoyl group;
2. aromatic acyl groups, including: the arylcarbonyl groups, such as the benzoyl, α-naphthoyl and β-naphthoyl groups; haloarylcarbonyl groups, such as the 2-bromobenzoyl and 4-chlorobenzoyl groups; lower alkylarylcarbonyl groups, such as the 2,4,6-trimethylbenzoyl and 4-toluoyl groups; lower alkoxyarylcarbonyl groups, such as the 4-anisoyl group; nitroarylcarbonyl groups, such as the 4-nitrobenzoyl and 2-nitrobenzoyl groups; lower alkoxycarbonylarylcarbonyl groups, such as the 2-(methoxycarbonyl)benzoyl group; and arylarylcarbonyl groups, such as the 4-phenylbenzoyl group;
3. alkoxycarbonyl groups, including: the lower alkoxycarbonyl groups, such as the methoxycarbonyl, ethoxycarbonyl, t-butoxycarbonyl and isobutoxycarbonyl groups; lower alkoxycarbonyl groups substituted by one or more halogen atoms and/or tri(lower alkyl)silyl groups, such as the 2,2,2-trichloroethoxycarbonyl and 2-trimethylsilylethoxycarbonyl groups;
4. alkenyloxycarbonyl groups, such as the vinyloxycarbonyl and allyloxycarbonyl groups;
5. aralkyloxycarbonyl groups which may optionally be substituted by 1 or 2 lower alkoxy groups or nitro groups on its aryl ring, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups;
6. silyl groups, including: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; tri(lower alkyl) silyl groups in which 1 or 2 of the alkyl groups has been replaced by 1 or 2 aryl groups, such as the diphenylmethylsilyl, diphenylbutylsilyl, diphenylisopropylsilyl and phenyldiisopropylsilyl groups;
7. aralkyl groups, including: lower alkyl groups substituted by from 1 to 3 aryl groups, such as the benzyl, phenethyl, 3-phenylpropyl, α-naphtylmethyl, β-naphthylmethyl, diphenylmethyl, triphenylmethyl, α-naphthyldiphenylmethyl and 9-anthrylmethyl groups, and such groups in which the aryl part is substituted by such substituents as lower alkyl, lower alkoxy, nitro and cyano groups and halogen atoms, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl and piperonyl groups; and
8. substituted methylene groups capable of forming a Schiff base, such as the N,N-dimethylaminomethylene, benzylidene, 4-methoxybenzylidene, 4-nitrobenzylidene, salicylidene, 5-chlorosalicylidene, diphenylmethylene and (5-chloro-2-hydroxyphenyl)phenylmethylene groups.

Examples of mercapto-protecting groups include:
1. aralkyl groups, including monoarylalkyl groups, such as the benzyl, p-methoxybenzyl and p-nitrobenzyl groups; di- and tri-arylmethyl groups, such as the diphenylmethyl, 4,4'-dimethoxydiphenylmethyl and trityl groups;
2. pyranyl groups, such as the 2-tetrahydropyranyl group;
3. aliphatic and aromatic acyl groups, such as the acetyl and benzoyl groups;
4. aralkyloxycarbonyl groups, such as the benzyloxycarbonyl and p-methoxybenzyloxycarbonyl groups;
5. alkoxycarbonyl groups, such as the t-butoxycarbonyl group; and
6. pyridinesulfenyl groups, such as the S-2-pyridinesulfenyl and S-3-nitro-2-pyridinesulfenyl groups.

Examples of suitable carboxy-protecting groups which may be used for protection during a reaction include:
1. lower alkyl groups, such as the methyl, ethyl, propyl, isopropyl, butyl, isobutyl, sec-butyl, t-butyl, pentyl and hexyl groups;
2. halogenated lower alkyl groups, such as the 2,2,2-trichloroethyl, 2-bromoethyl, 2-chloroethyl, 2-fluoroethyl and 2,2-dibromoethyl groups;
3. aralkyl groups, including: lower alkyl groups substituted by from 1 to 3 aryl groups, such as the benzyl, phenethyl, 3-phenylpropyl, α-naphtylmethyl, β-naphthylmethyl, diphenylmethyl, triphenylmethyl, α-naphthyldiphenylmethyl and 9-anthrylmethyl groups and such groups in which the aryl part is substituted by such substituents as lower alkyl, lower alkoxy, nitro, halogen and cyano groups and atoms, for example the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl and piperonyl groups.

Alternatively, a carboxy-protecting group able to be hydrolyzed in vivo and so usable for preparing a pro-drug for administration to the living body may be used, for example:
1. alkoxymethyl groups, including: lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups; lower-alkoxy-lower-alkoxymethyl groups, such as the 2-methoxyethoxymethyl group; halogenated lower alkoxymethyl groups, such as the 2,2,2-trichloroethoxymethyl and bis(2-chloroethoxy)methyl groups;
2. substituted ethyl groups, including: lower alkoxyethyl groups, such as the 1-ethoxyethyl, 1-methyl-1-methoxyethyl and 1-(isopropoxy)ethyl groups; haloethyl groups, such as the 2,2,2-trichloroethyl groups; and arylselenylethyl groups, such as the 2-(phenylselenyl) ethyl group;

3. aliphatic acyloxymethyl groups, such as the acetoxymethyl, propionyloxymethyl, butyryloxymethyl and pivaloyloxymethyl groups;
4. 1-lower-alkoxycarbonyloxyethyl groups, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl 1-isobutoxycarbonyloxyethyl and 1-cyclohexyloxycarbonyloxyethyl groups;
5. the cyclohexyloxycarbonyloxy(cyclohexyl)methyl group;
6. the phthalidyl group; and
7. the (2-oxo-5-methyl-1,3-dioxolen-4-yl)methyl group.

The compounds of the invention may contain asymmetric carbon atoms and/or carbon-carbon double bonds and can, therefore, form optical and/or cis/trans isomers. Although these are all referred to herein by a single formula, the present invention envisages both mixtures of the isomers (whether as obtained in the course of synthesis or by mixing) and the individual isolated isomers (which may be prepared by stereo-specific synthesis techniques or by separation of a synthesised mixture using conventional methods).

Examples of specific compounds of the present invention are those compounds of formula (I), given above, in which $R^1$ and $R^2$ are as defined in the following Table 1. In the Table, the following abbreviations are used to refer to certain substituent groups:

| | |
|---|---|
| Ac | acetyl |
| Aoc | allyloxycarbonyl |
| Boz | benzoyl |
| Bu | butyl |
| cBu | cyclobutyl |
| Byr | butyryl |
| Bz | benzyl |
| Car | carbamoyl |
| Dco | decanoyl |
| Ddc | dodecyl |
| Et | ethyl |
| Etc | ethoxycarbonyl |
| Fmoc | fluoenylmethoxycarbonyl |
| Fur | furyl |
| cHex | cyclohexenyl |
| cHp | cycloheptyl |
| Hpo | heptanoyl |
| Hx | hexyl |
| cHx | cyclohexyl |
| Hxo | hexanoyl |
| Ind | indolyl |
| Isox | isoxazolyl |
| Me | methyl |
| Mec | methoxycarbonyl |
| Mem | methoxyethoxymethyl |
| Mom | methoxymethyl |
| Mor | morpholino |
| Np | naphthyl |
| Oc | octyl |
| cOc | cyclooctyl |
| cPen | cyclopentenyl |
| Ph | phenyl |
| Pip | piperidyl |
| Piz | piperazinyl |
| Pn | pentyl |
| cPn | cyclopentyl |
| Pr | propyl |
| cPr | cyclopropyl |
| Prn | propionyl |
| Pyr | pyridyl |
| Pyrd | pyrrolidinyl |
| Retio | retinoyl |
| Thi | thienyl |
| Thiz | thiazolyl |
| Troc | trichloroethoxycarbonyl |

TABLE 1

| Cpd. No. | $R^1$ | $R^2$ |
|---|---|---|
| 1 | CH$_3$CH$_2$CO— | CH$_3$CH$_2$CO— |
| 2 | CH$_3$CH$_2$CO— | H |
| 3 | H | CH$_3$CH$_2$CO— |
| 4 | CH$_3$CH$_2$CH$_2$CO— | CH$_3$CH$_2$CH$_2$CO— |
| 5 | CH$_3$(CH$_2$)$_3$CO— | CH$_3$(CH$_2$)$_3$CO— |
| 6 | CH$_3$(CH$_2$)$_4$CO— | CH$_3$(CH$_2$)$_4$CO— |
| 7 | CH$_3$(CH$_2$)$_5$CO— | CH$_3$(CH$_2$)$_5$CO— |
| 8 | H | CH$_3$(CH$_2$)$_5$CO— |
| 9 | CH$_3$(CH$_2$)$_6$CO— | CH$_3$(CH$_2$)$_6$CO— |
| 10 | H | CH$_3$(CH$_2$)$_6$CO— |
| 11 | CH$_3$(CH$_2$)$_7$CO— | CH$_3$(CH$_2$)$_7$CO— |
| 12 | H | CH$_3$(CH$_2$)$_7$CO— |
| 13 | CH$_3$(CH$_2$)$_8$CO— | CH$_3$(CH$_2$)$_8$CO— |
| 14 | H | CH$_3$(CH$_2$)$_8$CO— |
| 15 | CH$_3$(CH$_2$)$_9$CO— | CH$_3$(CH$_2$)$_9$CO— |
| 16 | H | CH$_3$(CH$_2$)$_9$CO— |
| 17 | CH$_3$(CH$_2$)$_{10}$CO— | CH$_3$(CH$_2$)$_{10}$CO— |
| 18 | H | CH$_3$(CH$_2$)$_{10}$CO— |
| 19 | CH$_3$(CH$_2$)$_{11}$CO— | CH$_3$(CH$_2$)$_{11}$CO— |
| 20 | H | CH$_3$(CH$_2$)$_{11}$CO— |
| 21 | CH$_3$(CH$_2$)$_{12}$CO— | CH$_3$(CH$_2$)$_{12}$CO— |
| 22 | H | CH$_3$(CH$_2$)$_{12}$CO— |
| 23 | CH$_3$(CH$_2$)$_{13}$CO— | CH$_3$(CH$_2$)$_{13}$CO— |
| 24 | H | CH$_3$(CH$_2$)$_{13}$CO— |
| 25 | CH$_3$(CH$_2$)$_{14}$CO— | CH$_3$(CH$_2$)$_{14}$CO— |
| 26 | CH$_3$(CH$_2$)$_{14}$CO— | H |
| 27 | H | CH$_3$(CH$_2$)$_{14}$CO— |
| 28 | CH$_3$(CH$_2$)$_{15}$CO— | CH$_3$(CH$_2$)$_{15}$CO— |
| 29 | CH$_3$(CH$_2$)$_{15}$CO— | H |
| 30 | H | CH$_3$(CH$_2$)$_{15}$CO— |
| 31 | CH$_3$(CH$_2$)$_{16}$CO— | CH$_3$(CH$_2$)$_{16}$CO— |
| 32 | CH$_3$(CH$_2$)$_{16}$CO— | H |

TABLE 1-continued

| Cpd. No. | R$^1$ | R$^2$ |
|---|---|---|
| 33 | H | CH$_3$(CH$_2$)$_{16}$CO— |
| 34 | CH$_3$(CH$_2$)$_{17}$CO— | CH$_3$(CH$_2$)$_{17}$CO— |
| 35 | H | CH$_3$(CH$_2$)$_{17}$CO— |
| 36 | CH$_3$(CH$_2$)$_{18}$CO— | CH$_3$(CH$_2$)$_{18}$CO— |
| 37 | H | CH$_3$(CH$_2$)$_{18}$CO— |
| 38 | CH$_3$(CH$_2$)$_{19}$CO— | CH$_3$(CH$_2$)$_{19}$CO— |
| 39 | H | CH$_3$(CH$_2$)$_{19}$CO— |
| 40 | CH$_3$(CH$_2$)$_{20}$CO— | CH$_3$(CH$_2$)$_{20}$CO— |
| 41 | H | CH$_3$(CH$_2$)$_{20}$CO— |
| 42 | (CH$_3$)$_2$CHCH$_2$CO— | (CH$_3$)$_2$CHCH$_2$CO— |
| 43 | H | (CH$_3$)$_2$CHCH$_2$CO— |
| 44 | (CH$_3$)$_3$CCO— | (CH$_3$)$_3$CCO— |
| 45 | H | (CH$_3$)$_3$CCO— |
| 46 | CH$_2$=CHCH$_2$CO— | CH$_2$=CHCH$_2$CO— |
| 47 | H | CH$_2$=CHCH$_2$CO— |
| 48 | CH$_3$CH=CHCO— | CH$_3$CH=CHCO— |
| 49 | H | CH$_3$CH=CHCO— |
| 50 | (CH$_3$)$_2$=CHCO— | (CH$_3$)$_2$=CHCO— |
| 51 | H | (CH$_3$)$_2$=CHCO— |
| 52 | EtCH=CHCO— | EtCH=CHCO— |
| 53 | H | EtCH=CHCO— |
| 54 | H$_2$C=CHCH$_2$CH$_2$CO— | H$_2$C=CHCH$_2$CH$_2$CO— |
| 55 | H | H$_2$C=CHCH$_2$CH$_2$CO— |
| 56 | PrCH=CHCO— | PrCH=CHCO— |
| 57 | H | PrCH=CHCO— |
| 58 | EtCH=CHCH$_2$CO— | EtCH=CHCH$_2$CO— |
| 59 | H | EtCH=CHCH$_2$CO— |
| 60 | PnCH=CHCO— | PnCH=CHCO— |
| 61 | H | PnCH=CHCO— |
| 62 | HxCH=CHCO— | HxCH=CHCO— |
| 63 | H | HxCH=CHCO— |
| 64 | H$_2$C=CH(CH$_2$)$_7$CO— | H$_2$C=CH(CH$_2$)$_7$CO— |
| 65 | H | H$_2$C=CH(CH$_2$)$_7$CO— |
| 66 | H$_2$C=CH(CH$_2$)$_8$CO— | H$_2$C=CH(CH$_2$)$_8$CO— |
| 67 | H | H$_2$C=CH(CH$_2$)$_8$CO— |
| 68 | BuCH=CH(CH$_2$)$_7$CO— | BuCH=CH(CH$_2$)$_7$CO— |
| 69 | H | BuCH=CH(CH$_2$)$_7$CO— |
| 70 | HxCH=CH(CH$_2$)$_7$CO— | HxCH=CH(CH$_2$)$_7$CO— |
| 71 | H | HxCH=CH(CH$_2$)$_7$CO— |
| 72 | OcCH=CH(CH$_2$)$_7$CO— | OcCH=CH(CH$_2$)$_7$CO— |
| 73 | H | OcCH=CH(CH$_2$)$_7$CO— |
| 74 | Bu(CH$_2$CH=CH)$_2$(CH$_2$)$_7$CO— | Bu(CH$_2$CH=CH)$_2$(CH$_2$)$_7$CO— |
| 75 | H | Bu(CH$_2$CH=CH)$_2$(CH$_2$)$_7$CO— |
| 76 | Me(CH$_2$CH=CH)$_3$(CH$_2$)$_7$CO— | Me(CH$_2$CH=CH)$_3$(CH$_2$)$_7$CO— |
| 77 | H | Me(CH$_2$CH=CH)$_3$(CH$_2$)$_7$CO— |
| 78 | Bu(CH$_2$CH=CH)$_3$(CH$_2$)$_4$CO— | Bu(CH$_2$CH=CH)$_3$(CH$_2$)$_4$CO— |
| 79 | Pn(CH=CHCH$_2$)$_4$(CH$_2$)$_2$CO— | Pn(CH=CHCH$_2$)$_4$(CH$_2$)$_2$CO— |
| 80 | Me(CH$_2$CH=CH)$_6$(CH$_2$)$_2$CO— | Me(CH$_2$CH=CH)$_6$(CH$_2$)$_2$CO— |
| 81 | H | Pn(CH=CHCH$_2$)$_4$(CH$_2$)$_2$CO— |
| 82 | HxC(OH)H—CH$_2$CH=CHCO— | HxC(OH)H—CH$_2$CH=CHCO— |
| 83 | H | HxC(OH)H—CH$_2$CH=CHCO— |
| 84 | HOCH$_2$(CH$_2$)$_{14}$CO— | HOCH$_2$(CH$_2$)$_{14}$CO— |
| 85 | H | HOCH$_2$(CH$_2$)$_{14}$CO— |
| 86 | (4-MeOPh)$_2$PhC—OCH$_2$(CH$_2$)$_{14}$CO— | (4-MeOPh)$_2$PhC—OCH$_2$(CH$_2$)$_{14}$CO— |
| 87 | H | (4-MeOPh)$_2$PhC—OCH$_2$(CH$_2$)$_{14}$CO— |
| 88 | HC≡C.CO | HC≡C.CO |
| 89 | H | HC≡C.CO |
| 90 | MeC≡C.CO | MeC≡C.CO |
| 91 | H | MeC≡C.CO |
| 92 | PnC≡C.CO | PnC≡C.CO |
| 93 | H | PnC≡C.CO |
| 94 | MeOCH$_2$.CO | MeOCH$_2$.CO |
| 95 | MeOCH$_2$.CO | H |
| 96 | H | MeOCH$_2$.CO |
| 97 | DdcOCH$_2$CH$_2$.CO | DdcOCH$_2$CH$_2$.CO |
| 98 | H | DdcOCH$_2$CH$_2$.CO |
| 99 | MeO(CH$_2$)$_9$.CO | MeO(CH$_2$)$_9$.CO |
| 100 | MeO(CH$_2$)$_{11}$.CO | MeO(CH$_2$)$_{11}$.CO |
| 101 | MeO(CH$_2$)$_{13}$.CO | MeO(CH$_2$)$_{13}$.CO |
| 102 | MeO(CH$_2$)$_{15}$.CO | MeO(CH$_2$)$_{15}$.CO |
| 103 | H | MeO(CH$_2$)$_{13}$.CO |
| 104 | PhOCH$_2$.CO | PhOCH$_2$.CO |
| 105 | H | PhOCH$_2$.CO |
| 106 | Bz.CO | Bz.CO |
| 107 | H | Bz.CO |
| 108 | 2-PhPrn | 2-PhPrn |

TABLE 1-continued

| Cpd. No. | R¹ | R² |
|---|---|---|
| 109 | H | 2-PhPrn |
| 110 | 3-PhPrn | 3-PhPrn |
| 111 | H | 3-PhPrn |
| 112 | 6-PhHxo | 6-PhHxo |
| 113 | PhCH=CH.CO | PhCH=CH.CO |
| 114 | H | PhCH=CH.CO |
| 115 | β—Np.CH$_2$.CO | β—Np.CH$_2$.CO |
| 116 | H | β—Np.CH$_2$.CO |
| 117 | Boz | Boz |
| 118 | H | Boz |
| 119 | 2-Fur.CO | 2-Fur.CO |
| 120 | H | 2-Fur.CO |
| 121 | 2-Fur.CH=CH.CO | 2-Fur.CH=CH.CO |
| 122 | 3-Thi.CO | 3-Thi.CO |
| 123 | H | 3-Thi.CO |
| 124 | 2-Thi.CH=CH.CO | 2-Thi.CH=CH.CO |
| 125 | 3-Thi.CO | H |
| 126 | 2-Thi.CO | 2-Thi.CO |
| 127 | H | 2-Thi.CO |
| 128 | 2-ThiCH$_2$.CO | 2-ThiCH$_2$.CO |
| 129 | H | 2-ThiCH$_2$.CO |
| 130 | 2-NH$_2$-4-Thiz.CH$_2$.CO | 2-NH$_2$-4-Thiz.CH$_2$.CO |
| 131 | H | 2-NH$_2$-4-Thiz.CH$_2$.CO |
| 132 | 5-oxo-2-Pyrd.CO | 5-oxo-2-Pyrd.CO |
| 133 | H | 5-oxo-2-Pyrd.CO |
| 134 | 3-Isox.CO | 3-Isox.CO |
| 135 | H | 3-Isox.CO |
| 136 | 4-Isox.CO | 4-Isox.CO |
| 137 | H | 4-Isox.CO |
| 138 | 6-oxo-2-Pip.CO | 6-oxo-2-Pip.CO |
| 139 | H | 6-oxo-2-Pip.CO |
| 140 | 3-NH$_2$Prn | 3-NH$_2$Prn |
| 141 | H | 3-NH$_2$Prn |
| 142 | 6-NH$_2$Hxo | 6-NH$_2$Hxo |
| 143 | H | 6-NH$_2$Hxo |
| 144 | H$_2$N(CH$_2$)$_{11}$.CO | H$_2$N(CH$_2$)$_{11}$.CO |
| 145 | H$_2$N(CH$_2$)$_{11}$.CO | H |
| 146 | H$_2$N(CH$_2$)$_{15}$.CO | H$_2$N(CH$_2$)$_{15}$.CO |
| 147 | H$_2$N(CH$_2$)$_{15}$.CO | H |
| 148 | TrocNH(CH$_2$)$_2$.CO | TrocNH(CH$_2$)$_2$.CO |
| 149 | TrocNH(CH$_2$)$_2$.CO | H |
| 150 | TrocNH(CH$_2$)$_5$.CO | TrocNH(CH$_2$)$_5$.CO |
| 151 | TrocNH(CH$_2$)$_5$.CO | H |
| 152 | TrocNH(CH$_2$)$_{11}$.CO | TrocNH(CH$_2$)$_{11}$.CO |
| 153 | H | TrocNH(CH$_2$)$_{11}$.CO |
| 154 | TrocNH(CH$_2$)$_{15}$.CO | TrocNH(CH$_2$)$_{15}$.CO |
| 155 | H | TrocNH(CH$_2$)$_{15}$.CO |
| 156 | AocNH(CH$_2$)$_2$.CO | AocNH(CH$_2$)$_2$.CO |
| 157 | H | AocNH(CH$_2$)$_2$.CO |
| 158 | AocNH(CH$_2$)$_5$.CO | AocNH(CH$_2$)$_5$.CO |
| 159 | AocNH(CH$_2$)$_5$.CO | H |
| 160 | AocNH(CH$_2$)$_{11}$.CO | AocNH(CH$_2$)$_{11}$.CO |
| 161 | H | AocNH(CH$_2$)$_{11}$.CO |
| 162 | AocNH(CH$_2$)$_{15}$.CO | AocNH(CH$_2$)$_{15}$.CO |
| 163 | H | AocNH(CH$_2$)$_{15}$.CO |
| 164 | FmocNH(CH$_2$)$_{11}$.CO | FmocNH(CH$_2$)$_{11}$.CO |
| 165 | Ph$_3$C.S.NH(CH$_2$)$_{11}$.CO | Ph$_3$C.S.NH(CH$_2$)$_{11}$.CO |
| 166 | ClCH$_2$CO | ClCH$_2$CO |
| 167 | H | ClCH$_2$CO |
| 168 | FCH$_2$CO | FCH$_2$CO |
| 169 | H | FCH$_2$CO |
| 170 | BrCH$_2$CO | BrCH$_2$CO |
| 171 | H | BrCH$_2$CO |
| 172 | BrCH$_2$CO | H |
| 173 | ICH$_2$CO | ICH$_2$CO |
| 174 | ICH$_2$CO | H |
| 175 | H | ICH$_2$CO |
| 176 | MeSCH$_2$CO | MeSCH$_2$CO |
| 177 | H | MeSCH$_2$CO |
| 178 | MeS(CH$_2$)$_2$CO | MeS(CH$_2$)$_2$CO |
| 179 | MeS(CH$_2$)$_9$CO | MeS(CH$_2$)$_9$CO |
| 180 | MeS(CH$_2$)$_{11}$CO | MeS(CH$_2$)$_{11}$CO |
| 181 | MeS(CH$_2$)$_{15}$CO | MeS(CH$_2$)$_{15}$CO |
| 182 | MeSO$_2$CH$_2$CO | MeSO$_2$CH$_2$CO |
| 183 | H | MeSO$_2$CH$_2$CO |
| 184 | MeSO$_2$(CH$_2$)$_9$CO | MeSO$_2$(CH$_2$)$_9$CO |

TABLE 1-continued

| Cpd. No. | R¹ | R² |
|---|---|---|
| 185 | MeSO$_2$(CH$_2$)$_{11}$CO | MeSO$_2$(CH$_2$)$_{11}$CO |
| 186 | MeSO$_2$(CH$_2$)$_{15}$CO | MeSO$_2$(CH$_2$)$_{15}$CO |
| 187 | MeSO.CH$_2$CO | MeSO.CH$_2$CO |
| 188 | H | MeSO.CH$_2$CO |
| 189 | MeSO(CH$_2$)$_9$CO | MeSO(CH$_2$)$_9$CO |
| 190 | MeSO(CH$_2$)$_{11}$CO | MeSO(CH$_2$)$_{11}$CO |
| 191 | MeSO(CH$_2$)$_{15}$CO | MeSO(CH$_2$)$_{15}$CO |
| 192 | HxS.CH$_2$CO | HxS.CH$_2$CO |
| 193 | H | HxS.CH$_2$CO |
| 194 | DdcS.CH$_2$CO | DdcS.CH$_2$CO |
| 195 | H | DdcS.CH$_2$CO |
| 196 | PhS.CH$_2$CO | PhS.CH$_2$CO |
| 197 | H | PhS.CH$_2$CO |
| 198 | PhS(CH$_2$)$_9$CO | PhS(CH$_2$)$_9$CO |
| 199 | PhS(CH$_2$)$_{11}$CO | PhS(CH$_2$)$_{11}$CO |
| 200 | PhS(CH$_2$)$_{15}$CO | PhS(CH$_2$)$_{15}$CO |
| 201 | 2-PhEt.S.CH$_2$CO | 2-PhEt.S.CH$_2$CO |
| 202 | H | 2-PhEt.S.CH$_2$CO |
| 203 | Bz.SS.CH$_2$CO | Bz.SS.CH$_2$CO |
| 204 | H | Bz.SS.CH$_2$CO |
| 205 | Bz.SS(CH$_2$)$_9$CO | Bz.SS(CH$_2$)$_9$CO |
| 206 | Bz.SS(CH$_2$)$_{11}$CO | Bz.SS(CH$_2$)$_{11}$CO |
| 207 | Bz.SS(CH$_2$)$_{15}$CO | Bz.SS(CH$_2$)$_{15}$CO |
| 208 | Et$_2$NCH$_2$CO | Et$_2$NCH$_2$CO |
| 209 | Et$_2$NCH$_2$CO | H |
| 210 | Et$_2$N(CH$_2$)$_9$CO | Et$_2$N(CH$_2$)$_9$CO |
| 211 | Et$_2$N(CH$_2$)$_{11}$CO | Et$_2$N(CH$_2$)$_{11}$CO |
| 212 | Et$_2$N(CH$_2$)$_{15}$CO | Et$_2$N(CH$_2$)$_{15}$CO |
| 213 | 1-Me-4-Piz.CH$_2$CO | 1-Me-4-Piz.CH$_2$CO |
| 214 | H | 1-Me-4-Piz.CH$_2$CO |
| 215 | 1-Me-4-Piz.(CH$_2$)$_{15}$CO | 1-Me-4-Piz.(CH$_2$)$_{15}$CO |
| 216 | Me$_2$N(CH$_2$)$_9$CO | Me$_2$N(CH$_2$)$_9$CO |
| 217 | Me$_2$N(CH$_2$)$_{11}$CO | Me$_2$N(CH$_2$)$_{11}$CO |
| 218 | Me$_2$N(CH$_2$)$_{15}$CO | Me$_2$N(CH$_2$)$_{15}$CO |
| 219 | 4-Mor.CH$_2$CO | 4-Mor.CH$_2$CO |
| 220 | 4-Mor.CH$_2$CO | H |
| 221 | 4-Mor(CH$_2$)$_{15}$CO | 4-Mor(CH$_2$)$_{15}$CO |
| 222 | 4-Mor(CH$_2$)$_{15}$CO | H |
| 223 | 1-Pyrd.CH$_2$CO | 1-Pyrd.CH$_2$CO |
| 224 | H | 1-Pyrd.CH$_2$CO |
| 225 | 1-Pyrd(CH$_2$)$_{15}$CO | 1-Pyrd(CH$_2$)$_{15}$CO |
| 226 | H | 1-Pyrd(CH$_2$)$_{15}$CO |
| 227 | Etc(CH$_2$)$_{12}$CO | Etc(CH$_2$)$_{12}$CO |
| 228 | H | Etc(CH$_2$)$_{12}$CO |
| 229 | Mec(CH$_2$)$_{10}$CO | Mec(CH$_2$)$_{10}$CO |
| 230 | Car(CH$_2$)$_{12}$CO | Car(CH$_2$)$_{12}$CO |
| 231 | H | Car(CH$_2$)$_{12}$CO |
| 232 | Car(CH$_2$)$_{10}$CO | Car(CH$_2$)$_{10}$CO |
| 233 | Car(CH$_2$)$_{14}$CO | Car(CH$_2$)$_{14}$CO |
| 234 | HOOC(CH$_2$)$_{12}$CO | HOOC(CH$_2$)$_{12}$CO |
| 235 | HOOC(CH$_2$)$_{12}$CO | H |
| 236 | NC(CH$_2$)$_{10}$CO | NC(CH$_2$)$_{10}$CO |
| 237 | NC(CH$_2$)$_{15}$CO | NC(CH$_2$)$_{15}$CO |
| 238 | HO(CH$_2$)$_2$CO | HO(CH$_2$)$_2$CO |
| 239 | H | HO(CH$_2$)$_2$CO |
| 240 | HO(CH$_2$)$_5$CO | HO(CH$_2$)$_5$CO |
| 241 | H | HO(CH$_2$)$_5$CO |
| 242 | HO(CH$_2$)$_9$CO | HO(CH$_2$)$_9$CO |
| 243 | H | HO(CH$_2$)$_9$CO |
| 244 | HO(CH$_2$)$_{11}$CO | HO(CH$_2$)$_{11}$CO |
| 245 | H | HO(CH$_2$)$_{11}$CO |
| 246 | HO(CH$_2$)$_{15}$CO | HO(CH$_2$)$_{15}$CO |
| 247 | H | HO(CH$_2$)$_{15}$CO |
| 248 | MemO(CH$_2$)$_9$CO | MemO(CH$_2$)$_9$CO |
| 249 | MemO(CH$_2$)$_{11}$CO | MemO(CH$_2$)$_{11}$CO |
| 250 | MemO(CH$_2$)$_{15}$CO | MemO(CH$_2$)$_{15}$CO |
| 251 | MomO(CH$_2$)$_9$CO | MomO(CH$_2$)$_9$CO |
| 252 | MomO(CH$_2$)$_{11}$CO | MomO(CH$_2$)$_{11}$CO |
| 253 | MomO(CH$_2$)$_{15}$CO | MomO(CH$_2$)$_{15}$CO |
| 254 | HS(CH$_2$)$_2$CO | HS(CH$_2$)$_2$CO |
| 255 | HS(CH$_2$)$_2$CO | H |
| 256 | HS(CH$_2$)$_5$CO | HS(CH$_2$)$_5$CO |
| 257 | HS(CH$_2$)$_5$CO | H |
| 258 | HS(CH$_2$)$_{11}$CO | HS(CH$_2$)$_{11}$CO |
| 259 | HS(CH$_2$)$_{11}$CO | H |
| 260 | HS(CH$_2$)$_{15}$CO | HS(CH$_2$)$_{15}$CO |

TABLE 1-continued

| Cpd. No. | R¹ | R² |
| --- | --- | --- |
| 261 | HS(CH$_2$)$_{15}$CO | H |
| 262 | Ac.S(CH$_2$)$_9$CO | Ac.S(CH$_2$)$_9$CO |
| 263 | Ac.S(CH$_2$)$_{11}$CO | Ac.S(CH$_2$)$_{11}$CO |
| 264 | Ac.S(CH$_2$)$_{15}$CO | Ac.S(CH$_2$)$_{15}$CO |
| 265 | 4-PrBoz | 4-PrBoz |
| 266 | H | 4-PrBoz |
| 267 | 4-PhByr | 4-PhByr |
| 268 | 4-PhByr | H |
| 269 | 6-PhHxo | 6-PhHxo |
| 270 | 6-PhHxo | H |
| 271 | MecCH(NHAc).(CH$_2$)$_{10}$CO | MecCH(NHAc).(CH$_2$)$_{10}$CO |
| 272 | MecCH(NHAc).(CH$_2$)$_{12}$CO | MecCH(NHAc).(CH$_2$)$_{12}$CO |
| 273 | MecCH(NHAc).(CH$_2$)$_{16}$CO | MecCH(NHAc).(CH$_2$)$_{16}$CO |
| 274 | 1-Ind.CO | 1-Ind.CO |
| 275 | 1-Ind.CO | H |
| 276 | 1-(4H-cOc)CO | 1-(4H-cOc)CO |
| 277 | 1-(4H-cOc)CO | H |
| 278 | 2-PhOPrn | 2-PhOPrn |
| 279 | 2-PhOPrn | H |
| 280 | 3-Pyr.CH=CHCO | 3-Pyr.CH=CHCO |
| 281 | 3-Pyr.CH=CHCO | H |
| 282 | 2-Pyr.CH$_2$CO | 2-Pyr.CH$_2$CO |
| 283 | 2-Pyr.CH$_2$CO | H |
| 284 | 2-HxDco | 2-HxDco |
| 285 | H | 2-HxDco |
| 286 | 2-PnHpo | 2-PnHpo |
| 287 | H | 2-PnHpo |
| 288 | Me(CH$_2$)$_{14}$CO | Me(CH$_2$)$_{16}$CO |
| 289 | Me(CH$_2$)$_{16}$CO | Me(CH$_2$)$_{14}$CO |
| 290 | Me(CH$_2$)$_{16}$CO | OcCH=CH(CH$_2$)$_7$CO |
| 291 | Me(CH$_2$)$_{16}$CO | Me(CH$_2$)$_{12}$CO |
| 292 | Me(CH$_2$)$_{16}$CO | CH$_2$=CH(CH$_2$)$_8$CO |
| 293 | cPrCO | cPrCO |
| 294 | H | cPrCO |
| 295 | cBuCO | cBuCO |
| 296 | H | cBuCO |
| 297 | cPnCO | cPnCO |
| 298 | H | cPnCO |
| 299 | cPnCO | H |
| 300 | cHxCO | cHxCO |
| 301 | H | cHxCO |
| 302 | cHxCO | H |
| 303 | cHpCO | cHpCO |
| 304 | H | cHpCO |
| 305 | cOcCO | H |
| 306 | cOcCO | cOcCO |
| 307 | H | cOcCO |
| 308 | 1-cPenCO | 1-cPenCO |
| 309 | H | 1-cPenCO |
| 310 | 3-cHexCO | 3-cHexCO |
| 311 | H | 3-cHexCO |
| 312 | 3-cHexCO | H |
| 313 | 4-cHexCO | 4-cHexCO |
| 314 | 1-cHexCO | 1-cHexCO |
| 315 | 2-HOcPnCO | 2-HOcPnCO |
| 316 | 2-HOcPnCO | H |
| 317 | 4-NH$_2$cHxCO | 4-NH$_2$cHxCO |
| 318 | 4-NH$_2$cHxCO | H |
| 319 | 2-ClcHxCO | 2-ClcHxCO |
| 320 | Retio | Retio |
| 321 | H | Retio |
| 322 | Retio | H |
| 323 | Me(CH$_2$)$_{14}$CO | OcCH=CH(CH$_2$)$_7$CO |
| 324 | Me(CH$_2$)$_{14}$CO | Me(CH$_2$)$_{12}$CO |
| 325 | Me(CH$_2$)$_{14}$CO | CH$_2$=CH(CH$_2$)$_8$CO |
| 326 | Me$_3$SiCH$_2$CH$_2$OCH$_2$O(CH$_2$)$_{15}$CO | Me$_3$SiCH$_2$CH$_2$OCH$_2$O(CH$_2$)$_{15}$CO |
| 327 | MeSCH$_2$O(CH$_2$)$_9$CO | MeSCH$_2$O(CH$_2$)$_9$CO |
| 328 | MeSCH$_2$O(CH$_2$)$_{11}$CO | MeSCH$_2$O(CH$_2$)$_{11}$CO |
| 329 | MeSCH$_2$O(CH$_2$)$_{15}$CO | MeSCH$_2$O(CH$_2$)$_{15}$CO |

Of the compounds listed above, the following are preferred, that is to say Compounds No. 13, 15, 17, 19, 21, 23, 25, 28, 31, 34, 36, 38, 64, 66, 68, 70, 72, 74, 76, 78, 79, 80, 82, 84, 86, 99, 100, 101, 102, 144, 146, 152, 154, 160, 162, 164, 165, 179, 180, 181, 184, 185, 186, 189, 190, 191, 198, 199, 200, 205, 206, 207, 210, 211, 212, 215, 216, 217, 218, 221, 225, 227, 229, 230, 232, 233, 234, 236, 237, 242, 244, 246, 248, 249, 250, 251, 252, 253, 258, 260, 262, 263, 264, 271, 272, 273, 284, 286, 288, 289, 290, 291, 292, 323, 324, 325, 326, 327, 328 and 329, of which Compounds No. 13, 15, 17, 19, 21, 23, 25, 28, 31, 34, 36, 38, 64, 66, 68, 70, 72, 74, 76, 78, 79, 80, 82, 84, 86, 99, 100, 101, 102, 144, 146, 152, 154, 160, 162, 164, 165, 179, 180, 181, 198, 199, 200, 205, 206, 207, 210, 211, 212, 216, 217, 218, 227, 229, 230, 232, 233, 234, 242, 244, 246, 248, 249, 250, 251, 252, 253, 258, 260, 262, 263, 264, 284, 286, 288, 289, 290, 291, 292, 323, 324, 325, 326, 327, 328 and 329 are more preferred, and Compounds No. 13, 15, 17, 19, 21, 23, 25, 28, 31, 34, 36, 38, 64, 66, 68, 70, 72, 74, 76, 78, 79, 80, 82, 284, 286, 288, 289, 290, 291, 292, 323, 324, 325, 327, 328 and 329 are still more preferred. The most preferred individual compounds are Compounds No.:

15. 14,16-diundecanoylradicicol;
17. 14,16-dilauroylradicicol;
19. 14,16-ditridecanoylradicicol;
21. 14,16-dimyristoylradicicol;
23. 14,16-dipentadecanoylradicicol;
25. 14,16-dipalmitoylradicicol;
28. 14,16-diheptadecanoylradicicol;
31. 14,16-distearoylradicicol;
70. 14,16-dipalmitoleoylradicicol;
72. 14,16-dioleoylradicicol, and its isomeric 14,16-dielaidoylradicicol;
76. 14,16-dilinolenoylradicicol;
84. 14,16-di(16-hydroxypalmitoyl)radicicol;
146. 14,16-di(16-aminopalmitoyl)radicicol;
234. 14,16-di(16-carboxytridecanoyl)radicicol;
260. 14,16-di(16-mercaptopalmitoyl)radicicol;
288. 16-palmitoyl-14-stearoylradicicol;
323. 14-elaidoyl-16-palmitoylradicicol; and
325. 16-palmitoyl-14-(10-undecenoyl)radicicol.

The compounds of the present invention may be prepared by a variety of methods well known for preparing acylated compounds from the corresponding hydroxy compound. For example, compounds of formula (I) may be prepared by reacting a compound of formula (II):

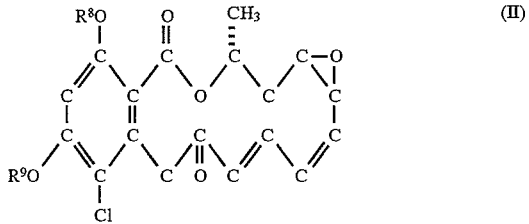

[in which either both of $R^8$ and $R^9$ represents a hydrogen atom or one of $R^8$ and $R^9$ represents a hydrogen atom and the other represents a hydroxy-protecting group, which may be one of the groups defined for $R^1$ and $R^2$ (other than a hydrogen atom) or any of the hydroxy-protecting groups exemplified above] with a compound of formula (III):

(in which $R^3$ is as defined above) or with a reactive derivative thereof, and, if required, removing any protecting group, to give said compound of formula (I).

Radicicol itself is the compound of formula (II) in which both $R^8$ and $R^9$ represent hydrogen atoms.

The reaction of the compound of formula (II) with a carboxylic acid of formula (III):

(in which $R^3$ is as defined above) or with a reactive derivative thereof can be conducted using any acylation reaction known this field.

If a carboxylic acid of formula (III) is used in the form of the free acid, the reaction is preferably effected in the presence of a suitable condensation agent, for example 1,1'-oxalyldiimidazole, 2,2'-dipyridyl disulfide, N,N'-dicyclohexylcarbodiimide (DCC), N,N'-disuccinimidyl carbonate, N,N'-bis(2-oxo-3-oxazolidinyl)phosphinic chloride, N,N'-carbodiimidazole, N,N'-disuccinimidyl oxalate (DSO), N,N'-diphthalimide oxalate (DPO), N,N'-bis (norbornenylsuccinimidyl)oxalate (BBTO), 1,1'-bis (benzotriazolyl)oxalate (BBTO), 1,1'-bis(6-chlorobenzotriazolyl)oxalate (BCTO) or 1,1'-bis(6-trifluoromethylbenzotriazolyl)oxalate (BTBO).

When a condensation agent is employed, the reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethyleneglycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphorotriamide; and sulfoxides, such as dimethyl sulfoxide and sulfolane.

The reaction can take place over a wide range of temperatures, and the precise reaction temperature is not critical to the invention. In general, we find it convenient to carry out the reaction at a temperature of from $-10°$ C. to $130°$ C.

If $R^1$ and $R^2$ are the same in the compound of formula (I), the compound of the present invention can be obtained by reaction of a compound of formula (II) as defined above with 2 and more equivalents of a carboxylic acid and a condensation agent or of a reactive derivative of the carboxylic acid. If a compound in which one of $R^1$ and $R^2$ represents a hydrogen atom is desired, it can be obtained by using less than 2 equivalents, preferably from 1 to 1.5 equivalents, of the carboxylic acid and a condensation agent or of a reactive derivative of the carboxylic acid.

If $R^1$ and $R^2$ both represent acyl groups which are different from each other in the compound of formula (I), the desired compound can be obtained by reaction of a compound of formula (II) in which one of $R^8$ and $R^9$ represents a hydrogen atom with 1 or more equivalents of the carboxylic acid and a condensation agent or of a reactive derivative of the carboxylic acid.

Examples of reactive derivatives of the carboxylic acid of formula (III) include: acid halides, such as the acid chloride and the acid bromide; and acid anhydrides.

When an acid halide is employed, the reaction is preferably conducted in an inert organic solvent in the presence of an acid binding agent. There is no particular restriction on the nature of the solvent to be employed, provided that it has no adverse effect on the reaction or on the reagents involved and that it can dissolve the reagents, at least to some extent.

Examples of suitable solvents include: aromatic hydrocarbons, such as benzene, toluene and xylene; halogenated hydrocarbons, especially halogenated aliphatic hydrocarbons, such as chloroform, methylene chloride and trichloroethane; ethers, such as diethyl ether, tetrahydrofuran and dioxane; aliphatic dialkylamides, which may be fatty acid amides, such as dimethylformamide and dimethylacetamide; nitriles, such as acetonitrile; ketones, such as acetone; dimethyl sulfoxide; and pyridine. The acid binding agent may be any such compound which binds to an acid and does not interfere with the reaction, and examples include: alkali metal hydroxides, such as sodium hydroxide and potassium hydroxide; alkali metal carbonates, such as sodium carbonate and potassium carbonate; and organic bases, such as triethylamine, pyridine, 4-dimethylaminopyridine and 1-methylimidazole.

The reaction can take place over a wide range of temperatures, and the precise reaction temperature is not critical to the invention. In general, we find it convenient to carry out the reaction at a temperature of from −10° C. to 130° C.

When an acid anhydride is employed, the reaction is preferably carried out in the presence of an inert organic solvent, or in the absence of an inert organic solvent by using an excess of the acid anhydride. There is no particular restriction on the nature of the solvent which may be employed, provided that it has no adverse effect on the reaction or on the reagents involved and that it can dissolve the reagents, at least to some extent. Examples of suitable solvents include: aromatic hydrocarbons, such as benzene, toluene and xylene; and ethers, such as dioxane, tetrahydrofuran, diethyleneglycol dimethyl ether.

The reaction can take place over a wide range of temperatures, and the precise reaction temperature is not critical to the invention. In general, we find it convenient to carry out the reaction at a temperature of from room temperature to 160° C.

The desired compound thus obtained can be collected, separated and purified by any suitable techniques. For example, one suitable recovery procedure comprises: pouring the reaction solution into water; extracted the resulting mixture with a water-immiscible solvent, such as benzene, ether or ethyl acetate; and finally removing the solvent e.g. by distillation to obtain the desired compound. The desired compound may, if necessary, be further purified by various methods, including: adsorption chromalography or ion exchange chromalography using various carriers, such as active carbon or silica gel; by gel filtration by using a Sephadex (trade mark) column; or by recrystallization from an ether (e.g. diethyl ether), ethyl acetate or chloroform.

When the compound of formula (II) contains a protecting group, the desired compound of formula (I) can be obtained by its removal, if necessary.

The removal of protecting group is required, the reaction employed will, as is well known in the art, vary depending upon the nature of the protecting group, and may be carried out using conventional procedures known in the technology of this field, for example as follows.

If a silyl group is employed as the hydroxy-protecting group, it can generally be removed by treatment with a compound capable of forming fluorine anions, such as tetrabutylammonium fluoride. The reaction is preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran and dioxane.

The reaction can take place over a wide range of temperatures, and the precise reaction temperature is not critical to the invention. In general, we find it convenient to carry out the reaction at a temperature of about room temperature. The time required for the reaction may also vary widely, depending on many factors, notably the reaction temperature and the nature of the reagents. However, provided that the reaction is effected under the preferred conditions outlined above, a period of from 10 to 18 hours will usually suffice.

If the hydroxy group is protected by an aralkyl or aralkyloxycarbonyl group, it can be removed by contact with a reducing agent. The removal is preferably performed by means of a catalytic reduction, which may take place at room temperature, by using a catalyst, such as palladium-carbon, platinum or Raney nickel. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; aliphatic acids, such as acetic acid; and a mixtures of any one or more of these organic solvents with water.

The reaction can take place over a wide range of temperatures, and the precise reaction temperature is not critical to the invention. In general, we find it convenient to carry out the reaction at a temperature of from 0° C. to room temperature. The time required for the reaction may also vary widely, depending on many factors, notably the reaction temperature and the nature of the reagents. However, provided that the reaction is effected under the preferred conditions outlined above, a period of from 5 minutes to 12 hours will usually suffice.

Such groups can be also removed by treating the compound with lithium or sodium in a liquid ammonia or in an alcohol, such as methanol or ethanol at a relatively low temperature, for example from −78° C. to −20° C.

Such groups can also be removed by using aluminum chloride-sodium iodide or an alkylsilyl halide, such as trimethylsilyl iodide. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitriles, such as acetonitile; halogenated hydrocarbons, especially halogenated aliphatic hydrocarbons, such as methylene chloride and chloroform; and mixtures of any two or more of these solvents.

The reaction can take place over a wide range of temperatures, and the precise reaction temperature is not critical to the invention. In general, we find it convenient to carry out the reaction at a temperature of from 0° C. to 50° C.

When the reaction substrate contains a sulfur atom, aluminum chloride-sodium iodide is preferably employed.

If the hydroxy-protecting group is an aliphatic acyl, aromatic acyl or alkoxycarbonyl group, it can be removed by treatment with a base in the presence of a solvent. The base employed is not particularly limited provided that it does not affect other parts of the compounds. The reaction is preferably performed using one of the following bases: metal alcoholates, such as sodium methoxide; aqueous ammonia; alkali metal carbonates, such as sodium carbonate and potassium carbonate; alkali metal hydroxides, such as sodium hydroxide and potassium hydroxide; and concentrated ammonia-methanol. There is no particular restriction on the nature of the solvent to be employed, provided that it has no adverse effect on the reaction or on the reagents involved and that it can dissolve the reagents, at least to some extent, and any solvent commonly used for hydrolysis reactions can equally be used here. Examples of suitable solvents include: alcohols, such as methanol, ethanol and propanol; ethers, such as tetrahydrofuran and dioxane; and mixtures of any one or more of these organic solvents with water.

The reaction can take place over a wide range of temperatures, and the precise reaction temperature is not critical to the invention. In general, we find it convenient to carry out the reaction at a temperature of from 0° C. to 150° C. in order to inhibit any side reaction. The time required for the reaction may also vary widely, depending on many factors, notably the reaction temperature and the nature of the reagents. However, provided that the reaction is effected under the preferred conditions outlined above, a period of from 1 to 10 hours will usually suffice.

When the hydroxy-protecting group is an alkoxymethyl, tetrahydropyranyl, tetrahydrothiopyranyl, tetrahydrofuranyl, tetrahydrothiofuranyl or substituted ethyl group, it can generally be removed by treatment with an acid in a solvent. Examples of suitable acids include: hydrochloric acid, acetic acid-sulfuric acid, p-toluenesulfonic acid and acetic acid. A strong acidic cation exchange resin, such as Dowex 50W can be employed instead. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; and mixtures of any one or more of these solvents with water.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents. However, provided that the reaction is effected under the preferred conditions outlined above, a period of from 10 minutes to 18 hours will usually suffice.

When the hydroxy-protecting group is an alkenyloxycarbonyl group, it can be removed by treatment with a base under similar conditions to those mentioned above for the case when the hydroxy-protecting group is an aliphatic acyl, aromatic acyl or alkoxycarbonyl group.

When the hydroxy-protecting group is an aryloxycarbonyl group, it can easily be removed using palladium together with triphenylphosphine or nickeltetracarbonyl with few side reactions.

When the amino-protecting group is a trialkylsilyl group, it can be removed by treating the compound with a compound as capable of forming fluorine anions, for example tetrabutylammonium fluoride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran and dioxane. The reaction can take place over a wide range of temperatures, and the precise reaction temperature is not critical to the invention. In general, we find it convenient to carry out the reaction at a temperature of about room temperature. The time required for the reaction may also vary widely, depending on many factors, notably the reaction temperature and the nature of the reagents. However, provided that the reaction is effected under the preferred conditions outlined above, a period of from 10 to 18 hours will usually suffice.

When the amino-protecting group is an aliphatic acyl, aromatic acyl or alkoxycarbonyl group or a substituted methylene group capable of forming a Schiff base, it can be removed by treatment with an acid or a base in the presence of an aqueous solvent. Suitable acids include hydrochloric acid, sulfuric acid, phosphoric acid and hydrobromic acid. Suitable bases may be selected from any commonly known bases, provided that they do not affect the other parts of the compound, and examples include: alkali metal carbonates, such as sodium carbonate and potassium carbonate; alkali metal hydroxides, such as sodium hydroxide and potassium hydroxide; and concentrated ammonia-methanol. There is no particular restriction on the nature of the solvent to be employed, provided that it has no adverse effect on the reaction or on the reagents involved and that it can dissolve the reagents, at least to some extent, and any solvent commonly used for hydrolysis reactions may equally be employed here. Examples of suitable solvents include: water; mixtures of one or more alcohols, such as methanol, ethanol or propanol, with water; and mixtures of one or more ethers, such as tetrahydrofuran or dioxane, with water. The reaction can take place over a wide range of temperatures, and the precise reaction temperature is not critical to the invention. In general, we find it convenient to carry out the reaction at a temperature of from 0° C. to 150° C., in order to inhibit any side reaction. The time required for the reaction may also vary widely, depending on many factors, notably the reaction temperature and the nature of the reagents. However, provided that the reaction is effected under the preferred conditions outlined above, a period of from 1 to 10 hours will usually suffice.

When the amino-protecting group is an aralkyl or aralkyloxycarbonyl group, it can preferably be removed by catalytic reduction at room temperature using, for example, platinum or palladium-on-carbon; or by using an oxidizing agent.

For the reductive removal, there is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol and isopropanol; ethers, such as diethyl ether, tetrahydrofuran and dioxane; aromatic hydrocarbons, such as toluene, benzene and xylene; aliphatic hydrocarbons, such as hexane and cyclohexane; esters, such as ethyl acetate and propyl acetate; aliphatic acids, such as acetic acid; and mixtures of any one or more of these solvents with water.

Preferred catalysts which may be used in this reaction are not particularly limited, provided that they are capable of use in catalytic reduction; and examples include: palladium-on-carbon, Raney nickel, platinum oxide, platinum black, rhodium-on-aluminum oxide, triphenylphosphine-on-rhodium chloride and palladium-on-barium sulfate.

Although there is no particular restriction on the pressure employed, the reaction is usually carried out at from 1 to 10 atmospheres.

The reaction can take place over a wide range of temperatures, and the precise reaction temperature is not critical to the invention, although the preferred temperature will vary, as is known in the art, depending upon the starting materials and the catalyst. In general, we find it convenient to carry out the reaction at a temperature of from 0° C. to 100° C. The time required for the reaction may also vary widely, depending on many factors, notably the reaction temperature and the nature of the reagents. However, provided that the reaction is effected under the preferred conditions outlined above, a period of from 5 minutes to 24 hours will usually suffice.

For the oxidative removal, there is no particular restriction on the nature of the solvent to be employed, provided that it has no adverse effect on the reaction or on the reagents involved and that it can dissolve the reagents, at least to some extent. Examples of suitable solvents include: aqueous organic solvents; preferred organic solvents which may be used include: ketones, such as acetone; halogenated hydrocarbons, especially halogenated aliphatic hydrocarbons, such as methylene chloride, chloroform and carbon tetrachloride; nitriles, such as acetonitrile; ethers, such as diethyl ether, tetrahydrofuran and dioxane; amides, which may be fatty acid amides, such as dimethylformamide, dimethylacetamide and hexamethylphosphorotriamide; and sulfoxides, such as dimethyl sulfoxide.

There is no particular restriction on the nature of the oxidizing agent employed, provided that it is capable of use for oxidation, and preferred examples include: potassium persulfate, sodium persulfate, ammonium cerium nitrate (CAN) and 2,3-dichloro-5,6-dicyano-p-benzoquinone (DDQ).

The reaction can take place over a wide range of temperatures, and the precise reaction temperature is not critical to the invention. In general, we find it convenient to carry out the reaction at a temperature of from 0° C. to 150° C., depending on the starting materials and the catalyst employed. The time required for the reaction may also vary widely, depending on many factors, notably the reaction temperature and the nature of the reagents. However, provided that the reaction is effected under the preferred conditions outlined above, a period of from 10 minutes to 24 hours will usually suffice.

When the amino-protecting group is an alkenyloxycarbonyl group, it can be removed by treatment with a base under similar conditions to those employed when the protecting group is an aliphatic acyl, aromatic acyl or lower alkoxycarbonyl group. In particular, when the amino-protecting group is an allyloxycarbonyl group, it can be removed conveniently and with few side reaction by using palladium and triphenylphosphine or nickeltetracarbonyl.

When the mercapto-protecting group is an aralkyl or aralkyloxycarbonyl group, it can generally be removed by contact with a reducing agent. For example, the removal may be performed by catalytic reduction at room temperature using palladium-on-carbon, platinum or Raney nickel as the catalyst. The reaction is conducted in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; aliphatic acids, such as acetic acid; and mixtures of any one or more of these solvents with water. The reaction can take place over a wide range of temperatures, and the precise reaction temperature is not critical to the invention. In general, we find it convenient to carry out the reaction at a temperature of from 0° C. to room temperature, depending on the starting materials and the reducing agent employed. The time required for the reaction may also vary widely, depending on many factors, notably the reaction temperature and the nature of the reagents. However, provided that the reaction is effected under the preferred conditions outlined above, a period of from 5 minutes to 12 hours will usually suffice.

Such groups can alternatively be removed by treatment with lithium or sodium in liquid ammonia or an alcohol, such as methanol or ethanol, at a relatively low temperature, e.g. from −78° C. to −20° C.

Alternatively, such groups can be removed by using aluminum chloride-sodium iodide or an alkylsilyl halide, such as trimethylsilyl iodide. The reaction is carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; halogenated hydrocarbons, especially halogenated aliphatic hydrocarbons, such as methylene chloride and chloroform; and mixtures of any two or more of these solvents. The reaction can take place over a wide range of temperatures, and the precise reaction temperature is not critical to the invention. In general, we find it convenient to carry out the reaction at a temperature of from 0° C. to 50° C., depending on the starting materials. The time required for the reaction may also vary widely, depending on many factors, notably the reaction temperature and the nature of the reagents.

When the mercapto-protecting group is an alkoxycarbonyl group, such as a t-butoxycarbonyl group or an arylmethyl group, it can be removed by treatment with an acid in the presence of a solvent. Preferred acids include, for example, trifluoroacetic acid and acetic acid-hydrobromic acid. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; and mixtures of any one or more of these solvents with water. The reaction can take place over a wide range of temperatures, and the precise reaction temperature is not critical to the invention. In general, we find it convenient to carry out the reaction at a temperature of from 0° C. to 50° C., depending on the starting materials and the acid employed. The time required for the reaction may also vary widely, depending on many factors, notably the reaction temperature and the nature of the reagents. However, provided that the reaction is effected under the preferred conditions outlined above, a period of from 10 minutes to 18 hours will usually suffice.

When the mercapto-protecting group is an aliphatic acyl, aromatic acyl or alkoxycarbonyl group, it can be removed by treatment with a base in the presence of a solvent. There is no particular restriction on the nature of the base employed, provided that it does not affect the other parts of the compound, and examples include: metal alcoholates, such as sodium methoxide; aqueous ammonia; alkali metal carbonates, such as sodium carbonate and potassium carbonate; alkali metal hydroxides, such as sodium hydroxide and potassium hydroxide; and concentrated ammonia-methanol. There is no particular restriction on the nature of the solvent to be employed, provided that it has no adverse effect on the reaction or on the reagents involved and that it can dissolve the reagents, at least to some extent, and any solvent commonly employed for hydrolysis reactions may equally be employed here. Examples of suitable solvents include: water; alcohols, such as methanol, ethanol and propanol; ethers, such as tetrahydrofuran and dioxane; and mixture of any one or more of these organic solvents with water. The reaction can take place over a wide range of temperatures, and the precise reaction temperature is not critical to the invention. In general, we find it convenient to carry out the reaction at a temperature of from 0° C. to 150° C., depending on the starting materials and the base employed, in order to inhibit any side reaction. The time required for the reaction may also vary widely, depending on many factors, notably the reaction temperature and the nature of the reagents. However, provided that the reaction is effected under the preferred conditions outlined above, a period of from 1 to 10 hours will usually suffice.

When the mercapto-protecting group is a tetrahydropyranyl group, it can generally be removed by treatment with an acid in a solvent. Preferred acids which may be used in this reaction include hydrochloric acid, acetic acid-sulfuric acid, p-toluenesulfonic acid and acetic acid. A strong acidic cation exchange resins, such as Dowex 50W may be employed instead. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; and mixtures of any one or more of these solvents with water. The reaction can take place over a wide range of temperatures, and the precise reaction temperature is not critical to the invention. In general, we find it convenient to carry out the reaction at a temperature of from 0° C. to 50° C., depending on the starting materials and the acid employed. The time required for the reaction may also vary widely, depending on many factors, notably the reaction temperature and the nature of the reagents. However, provided that the reaction is effected under the preferred conditions outlined above, a period of from 10 minutes to 18 hours will usually suffice.

When the mercapto-protecting group is an alkenyloxycarbonyl group, it can be removed by treatment with a base under similar conditions to those employed when the protecting group is an aliphatic acyl, aromatic acyl or alkoxycarbonyl group.

In particular, when the mercapto-protecting group is an allyloxycarbonyl group, it can be removed conveniently and with few side reactions by using palladium and triphenylphosphine or nickeltetracarbonyl.

When the mercapto-protecting group is an S-2-pyridinesulfenyl or S-3-nitro-2-pyridinesulfenyl group, it can be removed by reaction with a secondary amine, such as triphenylphosphine, pyrrolidine, piperidine or morpholine.

When the carboxy-protecting group is a lower alkyl group or an aryl group, it can be removed by treatment with an acid or a base.

Suitable acids include hydrochloric acid, sulfuric acid, phosphoric acid and hydrobromic acid. Suitable bases do not affect other parts of the compound, and examples include alkali metal carbonates, such as sodium carbonate and potassium carbonate, alkali metal hydroxides, such as sodium hydroxide and potassium hydroxide, and concentrated ammonia-methanol.

There is no particular restriction on the nature of the solvent to be employed, provided that it has no adverse effect on the reaction or on the reagents involved and that it can dissolve the reagents, at least to some extent, and any solvent commonly used for hydrolysis reactions may equally be used here. Examples of suitable solvents include: water; and mixtures of water with an alcohol, such as methanol, ethanol or propanol, or with an ether, such as tetrahydrofuran or dioxane. The reaction can take place over a wide range of temperatures, and the precise reaction temperature is not critical to the invention. In general, we find it convenient to carry out the reaction at a temperature of from 0° C. to 150° C., depending on the starting materials and the base employed, in order to inhibit any side reaction. The time required for the reaction may also vary widely, depending on many factors, notably the reaction temperature and the nature of the reagents. However, provided that the reaction is effected under the preferred conditions outlined above, a period of from 1 to 10 hours will usually suffice.

When the carboxy-protecting group is a di-aryl-substituted methyl group, such as a diphenylmethyl group, it can generally be removed under acidic conditions. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include aromatic hydrocarbons, such as anisole. Suitable acids include fluoroorganic acids, such as trifluoroacetic acid. The reaction can take place over a wide range of temperatures, and the precise reaction temperature is not critical to the invention. In general, we find it convenient to carry out the reaction at a temperature of about room temperature, depending on the starting materials. The time required for the reaction may also vary widely, depending on many factors, notably the reaction temperature and the nature of the reagents. However, provided that the reaction is effected under the preferred conditions outlined above, a period of from 30 minutes to 10 hours will usually suffice.

When the carboxy-protecting group is an aralkyl or halogenated lower alkyl group, it can be removed in general by contact with a reducing agent.

When the carboxy-protecting group is a halogenated lower alkyl group, zinc-acetic acid is preferably employed as the reducing agent. When the carboxy-protecting group is an aralkyl group, it can be removed by catalytic reduction by using palladium-carbon or platinum as the catalyst, or by using an alkali metal sulfides, such as potassium sulfide or sodium sulfide.

These reactions may be conducted in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; aliphatic acids, such as acetic acid; and mixtures of any one or more of these solvents with water. The reaction can take place over a wide range of temperatures, and the precise reaction temperature is not critical to the invention. In general, we find it convenient to carry out the reaction at a temperature of from 0° C. to near room temperature, depending on the starting materials and the reducing agent employed. The time required for the reaction may also vary widely, depending on many factors, notably the reaction temperature and the nature of the reagents. However, provided that the reaction is effected under the preferred conditions outlined above, a period of from 5 minutes to 12 hours will usually suffice.

When the carboxy-protecting group is an alkoxymethyl group, it can generally be removed by treatment with an acid. Preferred acids include hydrochloric acid, acetic acid-sulfuric acid and p-toluenesulfonic acid-acetic acid. The reaction is conducted in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; and mixtures of any one or more of these solvents with water. The reaction can take place over a wide range of temperatures, and the precise reaction temperature is not critical to the invention. In general, we find it convenient to carry out the reaction at a temperature of from 0° C. to 50° C., depending on the starting materials and the acid employed. The time required for the reaction may also vary widely, depending on many factors, notably the reaction temperature and the nature of the reagents. However, provided that the reaction is effected under the preferred conditions outlined above, a period of from 10 minutes to 18 hours will usually suffice.

In addition, where the compound thus obtained is a carboxylic acid compound, if desired, its corresponding alkali metal salt can be prepared by various conventional procedures, for example as follows: The carboxylic acid compound is dissolved in a mixed solvent of water with a water-immiscible organic solvent, such as ethyl acetate, then an aqueous solution of an alkali metal carbonate and an alkali metal bicarbonates, such as sodium bicarbonate and potassium carbonate, is added to the solution, preferably at from 0° C. to room temperature; the pH of the solution is then adjusted to a value of near 7, and the resulting separated precipitate is collected by filtration.

Furthermore, the salt or the carboxylic acid compound can be converted to its corresponding ester in which the carboxylic acid is protected by a protecting group which can easily be hydrolyzed in vivo by the procedures below: The salt or the acid is dissolved in an ether, such as tetrahydrofuran, or a polar solvent, such as N,N-dimethylformamide, dimethyl sulfoxide, hexamethylphosphorotriamide or triethylphosphate, and allowed to react with two equivalents of an organic base, such as triethylamine or dicyclohexylamine, an alkali metal hydride, such as sodium hydride, or an alkali metal carbonate or bicarbonate, such as sodium bicarbonate, sodium carbonate or potassium carbonate, to prepare its salt; and then the salt is allowed to react with an aliphatic acyloxymethyl halide, such as acetoxymethyl chloride or propionyloxymethyl bromide, a 1-(lower alkoxy)carbonyloxyethyl halide, such as 1-methoxycarbonyloxyethyl chloride or 1-ethoxycarbonyloxyethyl iodide, a phthalidyl halide, or a (2-oxo-5-methyl-1,3-dioxoren-4-yl)methyl halide. There is no particular restriction on the nature of the solvent to be employed, provided that it has no adverse effect on the reaction or on the reagents involved and that it can dissolve the reagents, at least to some extent. Examples of suitable solvents include any of the polar solvents mentioned above. The reaction can take place over a wide range of temperatures, and the precise reaction temperature is not critical to the invention. In general, we find it convenient to carry out the reaction at a temperature of from 0° C. to 100° C., depending on the starting materials, solvent and reagents employed. The time required for the reaction may also vary widely, depending on many factors, notably the reaction temperature and the nature of the reagents. However, provided that the reaction is effected under the preferred conditions outlined above, a period of from 0.5 to 10 hours will usually suffice, y be preferably employed.

Many of the radicicol derivatives of the present invention show a strong antitumor effect against transplanted M5076 cells in mice, and are therefore expected to demonstrate activity against solid type tumors in general.

Accordingly, the radicicol derivatives of the present invention can be used in warm-blooded animals, including humans, as an anti-tumor agent against these kinds of tumoral diseases. The compounds may be administered by any convenient route, for example by parenteral administration methods, such as intravenous injection, subcutaneous injection, intramuscular injection or by suppositories; or oral administration by using, for example, capsules, powders or granules.

The dosage to an adult human may vary depending on the nature of the disease, the route of administration and the administration frequency and period. However, a daily dosage of from 1 to 100 mg in a single dose or in divided doses may be given.

The radicicol derivative of the present invention may be administered in combination with other antitumor agents, for example, nitrosourea agents such as ACNU or BCNU, cisplatin, 5-FU, Daunomycin, adriamycin, mitomycin C and etoposide. In addition, preparations of the radicicol derivative can be provided for administration according to any conventional method. Therefore, the present invention covers any pharmaceutical preparations and compositions containing the radicicol derivatives of the present invention. The form will, of course, vary depending upon the route of administration.

For example, compositions for injection can be provided in the form of ampoules, each containing a unit dose amount, or in the form of a container containing multiple doses. The composition may sometimes contain additives such as emulsifiers, stabilizers and/or dispersants, and may often be in the form of a powder which is intended to be dissolved by the pharmacist in a suitable solvent, such as a pyrogen-free sterilized aqueous solvent, just before use. Such a preparation can be prepared, for example, as follows: The radicicol derivative is dissolved in acetone, and the acetone solution is poured into vials, water is added, and then the mixture is lyophilized. On the other hand, compositions for oral administration can be provided by means of capsules, powders, granules or syrups each containing a suitable amount of one or more of the radicicol derivatives of the present invention.

BIOLOGICAL ACTIVITY

The test animals used were female mice, 8 weeks old, of the $BDF_1$ strain, weighing 20–25 g. The mice were purchased from Charles River Japan Inc., Kanagawa, Japan. The mice were divided into experimental groups, each group containing 6 mice, and all mice within each group were treated identically. Each mouse was inoculated subcutaneouly with $1 \times 10^6$ viable cells (the number of cells was measured by a dye exclusion method under microscopy) of the mouse fibrosarcoma M5076.

The test compounds (80 mg) listed in the following Table, except radicicol, were dissolved in 0.2 ml of N,N-dimethylacetamide (DMA) and to the solution was added 0.2 ml of 40° C.-warmed HCO60 (polyoxyethylene hydrogenated caster oil 60). Immediately thereafter 3.6 ml of 40° C.-warmed physiological saline was added to form a colloidal solution or a suspension. The final concentration of DMA and HCO60 was 5% v/v, each. Radicicol was dissolved in 0.25 mg/ml of DMA and the solution was dispersed slowly into 3.75 ml of 10% Emulphor(trade mark)- physiological saline stirred well with a stirring rod. The final concentration of DMA was 6.25%. The solution was administered intravenously (in the case of a suspension it was administered intraperitoneally) on the first, fifth and ninth days following inoculation of the fibrosarcoma cells. The period for which the mice survived and the % inhibition of tumor growth were determined. A control group was treated identically, except that no active compound was administered.

The anti-tumor effect is shown in the following Table as the increase in life span [ILS (%)] and the growth inhibition [GI (%)], calculated from the following equations [R. I. Geran et al., Cancer Chemother. Rept., 3 (1972)]:

$$ILS(\%) + (Dt/Dc - 1) \times 100$$

where

Dt=median survival time (days) of mice in the treated group; and

Dc=median survival time (days) of mice in the control group.

In this experiment, Dc was 40–47 days.

$$GI(\%) = (1 - TDt/TDC) \times 100$$

where

TDt=average value of tumor sizes on the fourteenth day in the treated group; and TDc=average value of tumor sizes on the fourteenth day in the control group tumor size=(tumor length+tumor width )/2.

The compounds of the invention are identified in the following Table by the numbers assigned to them in the foregoing list.

TABLE 2

| Cpd No. | dose (mg/kg) | route | growth Inhibition (%) | ILS (%) |
|---|---|---|---|---|
| 17 | 200 | iv | 89 | 24 |
| 19 | 200 | iv | 89 | 9 |
| 21 | 200 | iv | 91 | 35 |
| 23 | 200 | iv | 95 | 35 |
| 25 | 200 | iv | 100 | 43 |
| 28 | 200 | iv | 95 | 27 |
| 31 | 200 | ip | 66 | −4 |
| 70 | 200 | iv | 65 | 31 |
| 72(cis) | 200 | iv | 80 | 4 |
| 72(trans) | 200 | iv | 86 | 9 |
| 76 | 200 | iv | 74 | 11 |
| radicicol | 150 | iv | 5 | −29 |

As is shown in the above Table, all of the compounds tested exhibited higher anti-tumor activitives than radicicol in the solid type tumor model (M5076 fibrosarcome sc implanted) in terms of both of tumor growth inhibition and increase in life span.

The invention is further illustrated by the following non-limiting Examples.

EXAMPLE 1

14,16-Dipalmitoylradicicol 1.6 g of radicicol was dissolved in 37 ml of dry benzene, and the solution was placed on an ice bath. While the solution was still on the ice bath, 2.2 ml of pyridine and a catalytic amount of dimethylaminopyridine were added to it, after which 20 ml of benzene containing 1.32 g of palmitoyl chloride was added dropwise. The reaction solution was then stirred for 1 hour on an ice bath, and ice water was added; it was then extracted with ethyl acetate. The organic layer was washed with an aqueous solution of sodium bicarbonate, with water and with a saturated solution of sodium chloride, in that order, after which it was dried over anhydrous magnesium sulfate. The magnesium sulfate was removed by filtration, and the solvent was then removed from the filtrate by distillation under reduced pressure. 2.70 g of an oily residue were thus obtained, and this was subjected to silica gel column chromatography using a 1:1 by volume mixture of hexane and ethyl acetate as the eluent, to obtain a crystalline substance having an Rf value of 0.64 (developing solvent, hexane:ethyl acetate=3:1 by volume). Recrystallization of this from hexane afforded 1.47 g of the title compound.

Nuclear Magnetic Resonance Spectrum (CDCl$_3$) δ ppm: 0.88 (6H, triplet, J=6.3 Hz); 1.21–1.42 (5OH, multiplet); 1.53 (3H, doublet, J=4.8 Hz); 1.63–1.79 (3H, multiplet); 2.37–2.45 (1H, multiplet); 2.49 (2H, triplet, J=6.8 Hz); 2.58 (2H, triplet, J=7.3 Hz); 2.99–3.02 (1H, multiplet); 3.52 (1H, multiplet); 3.91, 4.03 (2H, AB-quartet, J=16.1 Hz); 5.39–5.41 (1H, multiplet); 5.78 (1H, doublet of doublets, J=3.9 & 10.7 Hz); 6.06 (1H, doublet, J=16.1 Hz); 6.14 (1H, doublet of doublets, J=10.7 & 10.3 Hz); 7.01 (1H, singlet); 7.52 (1H, doublet of doublets, J=16.0 & 10.3 Hz).

Infrared Absorption Spectrum (Nujol—trade mark) ν$_{max}$ cm$^{-1}$: 1759, 1722.

EXAMPLE 2

14-Palmitoylradicicol

After the silica gel column chromatography of the mixture obtained as described in Example 1, 866 mg of the title compound having an Rf value of 0.31 (developing solvent, hexane:ethyl acetate=1:1 by volume) were obtained. Recrystallization from hexane afforded 731 mg of the title compound as white crystals.

Nuclear Magnetic Resonance Spectrum (CDCl$_3$) δ ppm: 0.88 (3H, triplet, J=6.3 Hz); 1.20–1.50 (24H, multiplet); 1.54 (3H, doublet, J=6.3 Hz); 1.72–1.80 (2H, multiplet); 1.85–1.96 (1H, multiplet); 2.34–2.42 (1H, multiplet); 2.59 (2H, triplet, J=7.3 Hz); 2.92–2.97 (1H, multiplet); 3.17 (1H, multiplet); 3.97, 4.69 (2H, AB-quartet, J=16.0 Hz); 5.53–5.58 (1H, multiplet); 5.83 (1H, doublet of doublets, J=10.7 & 3.0 Hz); 6.10 (1H, doublet, J=16.1 Hz); 6.14 (1H, doublet of doublets, J=10.7 & 9.2 Hz); 6.84 (1H, singlet); 7.42 (1H, doublet of doublets, J=17.0 & 9.2 Hz); 10.78 (1H, singlet).

Infrared Absorption Spectrum (Nujol) ν$_{max}$ cm$^{-1}$: 1772, 1717.

Elemental analysis: Calculated for C$_{34}$H$_{47}$O$_7$Cl: C, 67.70%; H, 7.85%; Cl, 5.88%. Found: C, 67.43%; H, 7.77%; Cl, 6.15%.

EXAMPLE 3

14,16-Di(octanoyl)radicicol

A procedure similar to that described in Example 1 was repeated, except that a mixture of 320 mg of radicicol, 7.4 ml of dry benzene, 880 μl of pyridine, a catalytic amount of dimethylaminopyridine and 338 mg (2.4 times the equimolar amount) of octanoyl chloride were used, to give 1.514 mg (yield 95%) of the title compound as an oily substance.

Nuclear Magnetic Resonance Spectrum (CDCl$_3$) δ ppm: 0.84–0.96 (6H, multiplet); 1.22–1.45 (17H, multiplet); 1.53

(3H, doublet, J=6.8 Hz); 1.51–1.62 (1H, multiplet); 1.64–1.80 (4H, multiplet); 2.36–2.44 (1H, multiplet); 2.50 (2H, triplet, J=7.4 Hz); 2.58 (2H, triplet, J=7.3 Hz); 2.96–3.04 (1H, multiplet); 3.52 (1H, multiplet); 3.91, 4.03 (2H, AB-quartet, J=16.1 Hz); 5.34–5.45 (1H, multiplet); 5.78 (1H, doublet of doublets, J=10.7 & 3.4 Hz); 6.06 (1H, doublet, J=16.1 Hz); 6.15 (1H, doublet of doublets, J=10.2 & 10.7 Hz); 7.01 (1H, singlet); 7.52 (1H, doublet of doublets, J=16.0 & 10.2 Hz);

Infrared Absorption Spectrum (CHCl$_3$) $v_{max}$ cm$^{-1}$: 1765, 1735

EXAMPLE 4

14,16-Di(behenoyl)radicicol

A methylene chloride solution containing 2.24 g of behenoyl chloride was added dropwise to a mixed solution of 1.459 g of radicicol, 37 ml of dry methylene chloride, 1.9 ml of pyridine and a catalytic amount of dimethylaminopyridine on an ice bath. The mixture was then reacted and treated as described in Example 1, to give a crystalline product having an Rf value of 0.80 (developing solvent, benzene:ethyl acetate=9:1 by volume). Recrystallization of this from hexane afforded 1.63 g of the title compound.

Nuclear Magnetic Resonance Spectrum (CDCl$_3$) δ ppm: 0.88 (6H, doublet, J=6.4 Hz); 1.24–1.45 (72H, multiplet); 1.54 (3H, doublet, J=6.8 Hz); 1.48–1.81 (5H, multiplet); 2.37–2.46 (1H, multiplet); 2.49 (2H, triplet, J=7.3 Hz); 2.58 (2H, triplet, J=7.3 Hz); 2.99–3.02 (1H, multiplet); 3.52 (1H, multiplet); 3.91, 4.03 (2H, AB-quartet, J=16.6 Hz); 5.36–5.45 (1H, multiplet); 5.78 (1H, doublet of doublets, J=11.0 & 3.9 Hz); 6.06 (1H, doublet, J=16.2 Hz); 6.14 (1H, doublet of doublets, J=11.0 & 10.3 Hz); 7.01 (1H, singlet); 7.52 (1H, doublet of doublets, J=11.0 & 10.3 Hz).

Infrared Absorption Spectrum (CHCl$_3$) $v_{max}$ cm$^{-1}$: 1770, 1738.

Elemental analysis: Calculated for $C_{62}H_{101}O_8Cl$: C, 73.74%; H, 10.08%; Cl, 3.51%. Found: C, 73.71%; H, 9.84%; Cl, 3.52%.

EXAMPLE 5

14-Behenoylradicicol

After the silica gel column chromatography of the mixture obtained as described in Example 4, a crystalline product having an Rf value of 0.64 (developing solvent, benzene:ethyl acetate=9:1 by volume) was obtained. Recrystallization of this from hexane afforded 463 mg of the title compound.

Nuclear Magnetic Resonance Spectrum (CDCl$_3$) δ ppm: 0.85 (3H, triplet, J=7.3 Hz); 1.22–1.45 (37H, multiplet); 1.54 (3H, doublet, J=6.8 Hz); 1.72–1.83 (2H, multiplet); 1.85–1.97 (1H, multiplet); 2.33–2.42 (1H, multiplet); 2.53 (2H, triplet, J=7.4 Hz); 2.93–2.97 (1H, multiplet); 3.16 (1H, multiplet); 3.96, 4.69 (2H, AB-quartet, J=16.6 Hz); 5.52–5.63 (1H, multiplet); 5.83 (1H, doublet of doublets, J=110 & 2.4 Hz); 6.10 (1H, doublet, J=16.1 Hz); 6.18 (1H, doublet of doublets, J=16.0 & 11.0 Hz); 6.84 (1H, singlet); 7.42 (1H, doublet of doublets, J=16.0 & 9.3 Hz); 10.78 (1H, singlet).

Infrared Absorption Spectrum (CHCl$_3$) $v_{max}$ cm$^{-1}$: 1770, 1725.

Elemental analysis: Calculated for $C_{40}H_{59}O_7Cl$: C, 69.90%; H, 8.65%; Cl, 5.16%. Found: C, 69.87%; H, 8.56%; Cl, 5.18%.

EXAMPLE 6

14,16-Di(stearoyl)radicicol

A procedure similar to that described in Example 4 was repeated, except that a mixed solution containing 1.459 g of radicicol, 37 ml of dry methylene chloride, 1.9 ml of pyridine, a catalytic amount of dimethylaminopyridine and 1.454 g of stearoyl chloride were reacted and treated, to give 923 mg of the title compound as crystals.

Nuclear Magnetic Resonance Spectrum (CDCl$_3$) δ ppm: 0.88 (6H, triplet, J=6.4 Hz); 1.21–1.42 (56H, multiplet); 1.53 (3H, doublet, J=6.8 Hz); 1.50–1.62 (1H, multiplet); 1.65–1.80 (4H, multiplet); 2.37–2.46 (1H, multiplet); 2.49 (2H, triplet, J=6.8 Hz); 2.58 (2H, triplet, J=7.3 Hz); 2.99–3.05 (1H, multiplet); 3.52 (1H, multiplet); 3.91, 4.63 (2H, AB-quartet, J=16.6 Hz); 5.35–5.46 (1H, multiplet); 5.78 (1H, doublet of doublets, J=10.7 & 3.9 Hz); 6.06 (1H, doublet, J=16.2 Hz); 6.14 (1H, doublet of doublets, J=10.7 & 10.3 Hz); 7.01 (1H, singlet); 7.52 (1H, doublet of doublets, J=16.0 & 10.3 Hz).

Infrared Absorption Spectrum (CHCl$_3$) $v_{max}$ cm$^{-1}$: 1772, 1740.

Elemental analysis: Calculated for $C_{54}H_{85}O_8Cl$: C, 72.25%; H, 9.54%; Cl, 3.95%. Found: C, 72.29%; H, 9.30%; Cl, 3.92%.

EXAMPLE 7

14-Stearoylradicicol

After the silica gel column chromatography of the mixture obtained as described in Example 6, a reaction product having an Rf value of 0.35 (developing solvent, hexane:ethyl acetate=2:1 by volume) was obtained. Recrystallization of this from hexane afforded 1.09 g of the title compound.

Nuclear Magnetic Resonance Spectrum (CDCl$_3$, 270 MHz) δ ppm: 0.88 (3H, triplet, J=6.4 Hz); 1.19–1.42 (29H, multiplet); 1.54 (3H, doublet, J=6.4 Hz); 1.72–1.80 (1H, multiplet); 1.86–1.96 (1H, multiplet); 2.33–2.42 (1H, multiplet); 2.59 (2H, triplet, J=7.4 Hz); 2.92–2.97 (1H, multiplet); 3.16 (1H, multiplet); 3.97, 4.69 (2H, AB-quartet, J=16.6 Hz); 5.53–5.62 (1H, multiplet); 5.83 (1H, doublet of doublets, J=10.7 & 2.4 Hz); 6.10 (1H, doublet, J=16.1 Hz); 6.18 (1H, doublet of doublets, J=10.7 & 9.3 Hz); 6.84 (1H, singlet); 7.42 (1H, doublet of doublets, J=16.0 & 9,3 Hz); 0.78 (1H, singlet).

Infrared Absorption Spectrum (CHCl$_3$) $v_{max}$ cm$^{-1}$: 1772, 1730

Elemental analysis: Calculated for $C_{36}H_{51}O_7Cl$: C, 68.50%; H, 8.14%; Cl, 5.62%. Found: C, 68.59%; H, 8.17%; Cl, 5.38%.

EXAMPLE 8

14,16-Di(oleoyl)radicicol

A procedure similar to that described in Example 4 was repeated, except that a mixed solution of 1.641 g of radicicol, 40 ml of dry methylene chloride, 2.14 ml of pyridine, a catalytic amount of dimethylaminopyridine and 1.49 g of oleoyl chloride were reacted and treated, to give 1.736 g of the title compound having an Rf value of 0.83 (developing solvent, hexane:ethyl acetate=2:1 by volume) as an oily substance.

Nuclear Magnetic Resonance Spectrum (CDCl$_3$, 270 MHz) δ ppm: 0.88 (6H, triplet, J=6.4 Hz); 1.22–1.42 (42H, multiplet); 1.53 (3H, doublet, J=6.3 Hz); 1.63–1.80 (4H, multiplet); 1.93–2.08 (7H, multiplet); 2.36–2.44 (1H, multiplet); 2.49 (2H, triplet, J=7.8 Hz); 2.58 (2H, triplet, J=7.3 Hz); 2.98–3.03 (1H, multiplet); 3.52 (1H, multiplet); 3.91, 4.03 (2H, AB-quartet, J=16.6 Hz); 5.28–5.46 (5H, multiplet); 5.78 (1H, doublet of doublets, J=10.8 & 3.9 Hz); 6.06 (1H, doublet, J=16.2 Hz); 6.14 (1H, doublet of doublets, J=10.8 & 10.3 Hz); 7.01 (1H, singlet); 7.52 (1H, doublet of doublets, J=16.4 & 10.3 Hz).

Infrared Absorption Spectrum (CHCl$_3$) $v_{max}$ cm$^{-1}$: 1770, 1742.

EXAMPLE 9

14-Oleoylradicicol

After, the silica gel column chromatography of the mixture obtained as described in Example 8, 872 mg of the title compound having an Rf value of 0.43 (developing solvent, hexane:ethyl acetate, 2:1 by volume) were obtained as an oily substance.

Nuclear Magnetic Resonance Spectrum (CDCl$_3$, 270 MHz) δ ppm: 0.87 (3H, triplet, J=6.4 Hz); 1.26–1.46 (22H, multiplet); 1.54 (3H, doublet, J=6.8 Hz); 1.72–1.80 (1H, multiplet); 1.86–2.00 (4H, multiplet); 2.33–2.43 (1H, multiplet); 2.59 (2H, triplet, J=7.4 Hz); 2.96–2.98 (1H, multiplet); 3.16 (1H, multiplet); 3.98, 4.68 (2H, AB-quartet, J=16.6 Hz); 5.32–5.41 (2H, multiplet); 5.52–5.61 (1H, multiplet); 5.83 (1H, doublet of doublets, J=10.0 & 2.9 Hz); 6.10 (1H, doublet, J=16.1 Hz); 6.18 (1H, doublet of doublets, J=10.0 & 8.8 Hz); 6.84 (1H, singlet); 7.42 (1H, doublet of doublets, J=16.1 & 8.8 Hz); 0.7 (1H, singlet).

Infrared Absorption Spectrum (CHCl$_3$) $v_{max}$ cm$^{-1}$: 1775, 1732.

EXAMPLE 10

14,16-Di(elaidoyl)radicicol

A procedure similar to that described in Example 4 was repeated, except that a mixed solution containing 1.641 g of radicicol, 40 ml of dry methylene chloride, 2.14 ml of pyridine, a catalytic amount of dimethylaminopyridine and 1.49 g of elaidoyl chloride was reacted and treated, to give 1.24 g of the title compound having an Rf value of 0.84 (developing solvent, hexane:ethyl acetate=2:1 by volume) as an oily substance.

Nuclear Magnetic Resonance Spectrum (CDCl$_3$, 270 MHz) δ ppm: 0.87 (6H, triplet, J=6.3 Hz); 1.26–1.48 (42H, multiplet); 1.53 (3H, doublet, J=6.3 Hz); 1.62–1.79 (4H, multiplet); 1.95–2.05 (7H, multiplet); 2.37–2.42 (1H, multiplet); 2.49 (2H, triplet, J=7.3 Hz); 2.58 (2H, triplet, J=7.3 Hz); 2.98–3.03 (1H, multiplet); 3.51 (1H, multiplet); 3.91, 4.03 (2H, AB-quartet, J=16.6 Hz); 5.30–5.46 (5H, multiplet); 5.78 (1H, doublet of doublets, J=10.7 & 3.9 Hz); 6.06 (1H, doublet, J=16.1 Hz); 6.14 (1H, doublet of doublets, J=10.7 & 10.7 Hz); 7.01 (1H, singlet); 7.52 (1H, doublet of doublets, J=16.0 & 10.7 Hz).

Infrared Absorption Spectrum (CHCl$_3$) $v_{max}$ cm$^{-1}$: 1772, 1740.

EXAMPLE 11

14-Elaidoylradicicol

After the silica gel column chromatography of the mixture obtained as described in Example 10, a product having an Rf value of 0.40 (developing solvent, hexane:ethyl acetate=2:1 by volume) was obtained. Recrystallization of this product from hexane afforded 1.22 g of the title compound as white crystals.

Nuclear Magnetic Resonance Spectrum (CDCl$_3$, 270 MHz) δ ppm: 0.87 (3H, triplet, J=6.3 Hz); 1.26–1.42 (21H, multiplet); 1.54 (3H, doublet, J=6.3 Hz); 1.72–1.80 (2H, multiplet); 1.86–1.96 (5H, multiplet); 2.33–2.43 (1H, multiplet); 2.59 (2H, triplet, J=7.3 Hz); 2.92–2.97 (1H, multiplet); 3.16 (1H, multiplet); 3.97, 4.69 (2H, AB-quartet, J=16.6 Hz); 5.51–5.59 (1H, multiplet); 5.83 (1H, doublet of doublets, J=10.7 & 2.9 Hz); 6.09 (1H, doublet, J=16.1 Hz); 6.18 (1H, doublet of doublets, J=10.7 & 8.7 Hz); 6.84 (1H, singlet); 7.42 (1H, doublet of doublets, J=16.0 & 8.7 Hz); 10.78 (1H, singlet).

Infrared Absorption Spectrum (CHCl$_3$) $v_{max}$ cm$^{-1}$: 1772, 1730.

EXAMPLE 12

14,16-Bis(2,2,2-trichloroethoxycarbonylaminohexanoyl)radicicol 182 mg of radicicol were dissolved in 6 ml of dry tetrahydrofuran, and 383 mg of 2,2,2-trichloroethoxycarbonylaminohexanoic acid, 363 mg of dicyclohexylcarbodiimide and a catalytic amount of dimethylaminopyridine were added at room temperature to the resulting solution; it was then stirred at the same temperature for 2 hours. At the end of this time, the dicyclohexylurea which was produced by a side reaction was filtered off. Water was added to the filtrate and the resulting mixture was extracted with ethyl acetate. The ethyl acetate solution was washed with an aqueous solution of sodium bicarbonate and then with water, after which it was dried over anhydrous magnesium sulfate. The solvent was then removed by distillation under reduced pressure. The resulting residue was purified by silica gel column chromatography, using a 1:1 by volume mixture of hexane and ethyl acetate as the eluent. After condensation of the eluate having an Rf value of 0.75 (developing solvent, ethyl acetate:hexane=2:1 by volume), 191 mg of the title compound was obtained.

Nuclear Magnetic Resonance Spectrum (CDCl$_3$, 270 MHz) δ ppm: 1.15–1.98 (13H, multiplet); 1.53 (3H, doublet, J=6.3 Hz); 2.40–2.46 (1H, multiplet); 2.50–2.56 (2H, multiplet); 2.61 (2H, triplet, J=7.3 Hz); 3.00–3.04 (1H, multiplet); 3.24 (2H, triplet, J=6.8 Hz); 3.29 (2H, triplet, J=6.9 Hz); 3.52 (1H, multiplet); 3.93, 4.01 (2H, AB-quartet, J=16.1 Hz); 4.72 (4H, singlet); 4.95–5.04 (1H, multiplet); 5.06–5.17 (1H, multiplet); 5.40–5.45 (1H, multiplet); 5.80 (1H, doublet of doublets, J=10.7 & 3.9 Hz); 6.06 (1H, doublet, J=16.1 Hz); 6.15 (1H, doublet of doublets, J=10.2 & 10.7 Hz); 7.03 (1H, singlet); 7.53 (1H, doublet of doublets, J=10.7 & 10.2 Hz).

Infrared Absorption Spectrum (CHCl$_3$) $v_{max}$ cm$^{-1}$: 1770, 1740.

EXAMPLE 13

16-(2,2,2-Trichloroethoxycarbonylaminohexanoyl)radicicol

The eluate having an Rf value of 0.51 (developing solvent, ethyl acetate:hexane=2:1 by volume) in the silica gel column chromatography of the mixture obtained as described in Example 12 was condensed, to give 28 mg of the title compound.

Nuclear Magnetic Resonance Spectrum (CDCl$_3$, 270 MHz) δ ppm: 1.53 (3H, doublet, J=6.3 Hz); 1.42–1.78 (7H, multiplet); 2.35–2.44 (1H, multiplet); 2.50–2.56 (2H, multiplet); 2.98–3.04 (1H, multiplet); 3.25 (1H, triplet, J=6.4 Hz); 3.27 (1H, triplet, J=6.3 Hz); 3.56 (1H, multiplet); 4.01, 4.02 (2H, AB-quartet, J=16.1 Hz); 4.72 (2H, singlet); 5.08–5.16 (1H, multiplet); 5.38–5.48 (1H, multiplet); 5.79 (1H, doublet of doublets, J=10.8 & 3.9 Hz); 6.06 (1H, doublet, J=16.1 Hz); 6.11 (1H, singlet); 6.15 (1H, doublet of doublets, J=10.8 & 10.2 Hz); 6.78 (1H, singlet); 7.58 (1H, doublet of doublets, J=16.0 & 10.2 Hz).

EXAMPLE 14

14,16-Di(methoxyacetyl)radicicol 82 mg of radicicol, 4 ml of dry methylene chloride, 255 μl of pyridine, a catalytic amount of dimethylaminopyridine and 412 mg of methoxyacetyl chloride were reacted together, and then the product was treated, in each case in a similar manner to that described in Example 4, to give a mixture. This mixture was purified by silica gel short column chromatography using a 3:1 by volume mixture of ethyl acetate and hexane as the eluent, to give 255 mg of the title compound as an oily substance.

Nuclear Magnetic Resonance Spectrum (CDCl$_3$, 270 MHz) δ ppm: 1.54 (3H, doublet, J=6.3 Hz); 1.53–1.68 (1H, multiplet); 2.37–2.43 (1H, multiplet); 2.98–3.05 (1H, multiplet); 3.50 (3H, singlet); 3.52 (1H, multiplet); 3.53 (3H, singlet); 3.95, 4.07 (2H, AB-quartet, J=16.1 Hz); 4.23 (2H, singlet); 4.33 (2H, singlet); 5.36–5.46 (1H, multiplet); 5.78 (1H, doublet of doublets, J=11.2 & 3.9 Hz); 6.06 (1H, doublet, J=16.1 Hz); 6.15 (1H, doublet of doublets, J=11.2 & 10.8 Hz); 7.26 (1H, singlet); 7.49 (1H, doublet of doublets, J=16.0 & 10.8 Hz).

Infrared Absorption Spectrum (CHCl$_3$) ν$_{max}$ cm$^{-1}$: 1792, 1740.

EXAMPLE 15

14-Methoxyacetylradicicol 1.54 g of 14,16-di(methoxyacetyl)radicicol (prepared as described in Example 14) was dissolved in 20 ml of ethyl acetate, and 15 g of silica gel were added to the resulting solution; the mixture was then stirred for 23 hours at room temperature. At the end of this time, the silica gel was removed by filtration, and the solution was washed well with ethyl acetate. The filtrate and the washings were combined and condensed by evaporation under reduced pressure, and the resulting residue was purified by silica gel column chromatography using a 2:1 by volume mixture of ethyl acetate and hexane as the eluent. The eluate having an Rf value of 0.50 (developing solvent, ethyl acetate:hexane=2:1 by volume) was collected and condensed, to give 340 mg of the title compound as an oily substance.

Nuclear Magnetic Resonance Spectrum (CDCl$_3$, 270 MHz) δ ppm: 1.53 (3H, doublet, J=6.8 Hz); 1.86–1.97 (1H, multiplet); 2.34–2.42 (1H, multiplet); 2.92–2.97 (1H, multiplet); 3.17 (1H, multiplet); 3.53 (3H, singlet); 3.98, 4.70 (2H, AB-quartet, J=16.6 Hz); 5.51–5.60 (1H, multiplet); 5.84 (1H, doublet of doublets, J=10.7 & 2.9 Hz); 6.10 (1H, doublet, J=16.1 Hz); 6.18 (1H, doublet of doublets, J=10.7 & 9.2 Hz); 6.89 (1H, singlet); 7.42 (1H, doublet of doublets, J=17.0 & 9.2 Hz); 0.79 (1H, singlet).

Infrared Absorption Spectrum (CHCl$_3$) ν$_{max}$ cm$^{-1}$: 1790, 1725.

EXAMPLE 16

16-Methoxyacetylradicicol

The eluate having an Rf value of 0.42 (developing solvent, ethyl acetate:hexane=2:1 by volume) obtained in the course of the silica gel column chromatography described in Example 15 was collected and condensed, to give 357 mg of the title compound.

Nuclear Magnetic Resonance Spectrum (CDCl$_3$, 270 MHz) δ ppm: 1.51 (3H, doublet, J=6.9 Hz); 1.58–1.67 (1H, multiplet); 2.34–2.42 (1H, multiplet); 2.98–3.04 (1H, multiplet); 3.51 (3H, singlet); 3.52 (1H, multiplet); 4.00, 4.13 (2H, AB-quartet, J=16.1 Hz); 4.24 (2H, singlet); 5.32–5.42 (1H, multiplet); 5.77 (1H, doublet of doublets, J=10.7 & 3.9 Hz); 5.99 (1H, singlet); 6.06 (1H, doublet, J=16.1 Hz); 6.15 (1H, doublet of doublets, J=10.7 & 10.2 Hz); 6.82 (1H, singlet); 7.52 (1H, doublet of doublets, J=16.0 & 10.2 Hz).

Infrared Absorption Spectrum (CHCl$_3$) ν$_{max}$ cm$^{-1}$: 1782, 1730.

EXAMPLE 17

14,16-Di(benzoyl)radicicol

Following a procedure similar to that described in Example 4, 1.459 g of radicicol, 37 ml of dry methylene chloride, 1.9 ml of pyridine, a catalytic amount of dimethylaminopyridine and 618 mg of benzoyl chloride were reacted together, and the product was treated, to give 965 mg of the title compound as crystals.

Nuclear Magnetic Resonance Spectrum (CDCl$_3$, 270 MHz) δ ppm: 1.24–1.38 (1H, multiplet); 1.39 (3H, doublet, J=6.3 Hz); 2.13–2.20 (1H, multiplet); 2.94–2.99 (1H, multiplet); 3.61 (1H, multiplet); 3.97, 4.23 (2H, AB-quartet, J=16.1 Hz); 5.09–5.18 (1H, multiplet); 5.77 (1H, doublet of doublets, J=10.7 & 4.3 Hz); 6.08 (1H, doublet, J=16.1 Hz); 6.17 (1H, doublet of doublets, J=10.7 & 7.3 Hz); 7.26 (1H, singlet); 7.43–7.71 (6H, multiplet); 8.17 (1H, doublet of doublets, J=17.0 & 7.3 Hz); 8.12–8.23 (4H, multiplet).

Infrared Absorption Spectrum (Nujol) ν$_{max}$ cm$^{-1}$: 1748, 1728.

Elemental analysis: Calculated for $C_{32}H_{25}O_8Cl$: C, 67.08%; H, 4.40%; Cl, 6.19%. Found: C, 67.11%; H, 4.58%; Cl, 6.25%.

EXAMPLE 18

14-Benzoylradicicol

After the silica gel column chromatography described in Example 17, 756 mg of the title compound having an Rf value of 0.61 (developing solvent, ethyl acetate:hexane=2:1 by volume) was obtained as an oily substance.

Nuclear Magnetic Resonance Spectrum (CDCl$_3$, 270 MHz) δ ppm: 1.56 (3H, doublet, J=6.8 Hz); 1.88–1.98 (1H, multiplet); 2.34–2.44 (1H, multiplet); 2.93–2.98 (1H, multiplet); 3.20 (1H, multiplet); 4.02, 4.72 (2H, AB-quartet, J=16.6 Hz); 5.55–5.65 (1H, multiplet); 6.12 (1H, doublet, J=16.6 Hz); 6.21 (1H, doublet of doublets, J=10.7 & 10.4 Hz); 7.03 (1H, singlet); 7.45 (1H, doublet of doublets, J=14.0 & 8.7 Hz); 7.41–7.70 (3H, multiplet); 8.18 (2H, multiplet); 10.82 (1H, singlet).

Infrared Absorption Spectrum (CHCl$_3$) ν$_{max}$ cm$^{-1}$: 1750.

EXAMPLE 19

14,16-Di(phenoxyacetyl)radicicol

Following a procedure similar to that described in Example 4, 1.459 g of radicicol, 37 ml of dry methylene chloride, 1.9 ml of pyridine, a catalytic amount of dimethylaminopyridine and 819 mg of phenoxyacetyl chloride were reacted together, and the product was treated, to give 661 mg of the title compound as an oily substance.

Nuclear Magnetic Resonance Spectrum (CDCl$_3$, 270 MHz) δ ppm: 1.33–1.43 (1H, multiplet); 1.50 (3H, doublet, J=6.3 Hz); 2.21–2.31 (1H, multiplet); 2.94–2.99 (1H, multiplet); 3.44 (1H, multiplet); 3.95, 4.03 (2H, AB-quartet, J=16.6 Hz); 4.82 (2H, singlet); 4.93 (2H, singlet); 5.29–5.38 (1H, multiplet); 5.78 (1H, doublet of doublets, J=10.7 & 3.4 Hz); 6.05 (1H, doublet, J=16.2 Hz); 6.13 (1H, doublet of doublets, J=10.7 & 10.7 Hz); 6.93–7.17 (6H, multiplet); 7.27 (1H, singlet); 7.30–7.38 (4H, multiplet); 7.51 (1H, doublet of doublets, J=16.0 & 10.7 Hz).

Infrared Absorption Spectrum (CHCl$_3$) ν$_{max}$ cm$^{-1}$: 1796, 1738.

EXAMPLE 20

14,16-Di(phenylacetyl)radicicol

Following a procedure similar to that described in Example 4, but reacting 1.641 g of radicicol, 40 ml of dry methylene chloride, 2.14 ml of pyridine, a catalytic amount of dimethylaminopyridine and 765 mg of phenylacetyl chloride, 926 mg of the title compound were obtained.

Nuclear Magnetic Resonance Spectrum (CDCl$_3$, 270 MHz) δ ppm: 0.98–1.08 (1H, multiplet); 1.43 (3H, doublet, J=6.4 Hz); 2.07–2.17 (1H, multiplet); 2.85–2.93 (1H, multiplet); 3.36 (1H, multiplet); 3.71–3.98 (2H, multiplet); 3.88 (4H, singlet); 4.93–5.05 (1H, multiplet); 5.75 (1H, doublet of doublets, J=10.7 & 3.9 Hz); 6.00 (1H, doublet, J=16.1 Hz); 6.09 (1H, doublet of doublets, J=10.7 & 10.3 Hz); 6.98 (1H, singlet); 7.30–7.36 (10H, multiplet); 7.45 (1H, doublet of doublets, J=16.0 & 10.3 Hz).

Infrared Absorption Spectrum (CHCl$_3$) ν$_{max}$ cm$^{-1}$: 1775, 1745.

EXAMPLE 21

14-Phenylacetylradicicol

After the silica gel column chromatography described in Example 20, 403 mg of the title compound having an Rf value of 0.43 (developing solvent, ethyl acetate:hexane=1:1 by volume) were obtained.

Nuclear Magnetic Resonance Spectrum (CDCl$_3$, 270 MHz) δ ppm: 1.53 (3H, doublet, J=6.8 Hz); 1.85–1.95 (1H, multiplet); 2.35–2.43 (1H, multiplet); 2.91–2.96 (1H, multiplet); 3.14 (1H, multiplet); 3.90 (2H, singlet); 3.95, 4.67 (2H, AB-quartet, J=16.2 Hz); 5.51–5.58 (1H, multiplet); 5.82 (1H, doublet of doublets, J=10.8 & 2.9 Hz); 6.08 (1H, doublet, J=16.6 Hz); 6.16 (1H, doublet of doublets, J=10.8 & 9.3 Hz); 6.82 (1H, singlet); 7.35 (5H, multiplet); 7.40 (1H, doublet of doublets, J=16.0 & 9.3 Hz); 0.76 (1H, singlet).

Infrared Absorption Spectrum (CHCl$_3$) ν$_{max}$ cm$^{-1}$: 1770, 1728.

EXAMPLE 22

14,16-Di(chloroacetyl)radicicol

Following a procedure similar to that described in Example 4, but using 1.82 g of radicicol, 40 ml of dry methylene chloride, 2.55 ml of pyridine, a catalytic amount of dimethylaminopyridine and 1.24 ml of chloroacetyl chloride, 2.6 g of the title compound were obtained.

Nuclear Magnetic Resonance Spectrum (CDCl$_3$, 270 MHz) δ ppm: 1.55 (3H, doublet, J=6.4 Hz); 1.52–1.66 (1H, multiplet); 2.36–2.46 (1H, multiplet); 2.98–3.05 (1H, multiplet); 3.48 (1H, multiplet); 3.94, 4.06 (2H, AB-quartet, J=16.6 Hz); 4.24 (2H, singlet); 4.34 (2H, singlet); 5.38–5.48 (1H, multiplet); 5.80 (1H, doublet of doublets, J=11.0 & 3.4 Hz); 6.06 (1H, doublet, J=16.2 Hz); 6.15 (1H, doublet of doublets, J=11.0 & 10.3 Hz); 7.25 (1H, singlet); 7.49 (1H, doublet of doublets, J=16.2 & 10.3 Hz).

Infrared Absorption Spectrum (CHCl$_3$) ν$_{max}$ cm$^{-1}$: 1795, 1765, 1740.

EXAMPLE 23

14,16-Di(2-thenoyl)radicicol

Following a procedure similar to that described in Example 4, but using 1.094 g of radicicol, 28 ml of dry methylene chloride, 1.4 ml of pyridine, a catalytic amount of dimethylaminopyridine and 528 mg of 2-thenoyl chloride, 1.39 g of the title compound was obtained.

Nuclear Magnetic Resonance Spectrum (CDCl$_3$, 270 MHz) δ ppm: 1.43 (3H, doublet, J=6.8 Hz); 1.34–1.45 (1H, multiplet); 2.18–2.26 (1H, multiplet); 2.96–3.03 (1H, multiplet); 3.58 (1H, multiplet); 3.96, 4.23 (2H, AB-quartet, J=16.1 Hz); 5.14–5.26 (1H, multiplet); 5.76 (1H, doublet of doublets, J=11.0 & 4.3 Hz); 6.07 (1H, doublet, J=16.1 Hz); 6.16 (1H, doublet of doublets, J=11.0 & 10.2 Hz); 7.18–7.21 (2H, multiplet); 7.26 (1H, singlet); 7.45 (1H, doublet of doublets, J=16.6 & 10.2 Hz); 7.72 (2H, multiplet); 7.96–8.03 (2H, multiplet).

Infrared Absorption Spectrum (CHCl$_3$) ν$_{max}$ cm$^{-1}$: 1745, 1725.

Elemental analysis Calculated for $C_{28}H_{21}O_8ClS_2$: C, 57.40%; H, 3.62%; Cl, 6.06%. Found: C, 57.61%; H, 3.76%; Cl, 5.93%.

EXAMPLE 24

14-(2-Thenoyl)radicicol

After the silica gel column chromatography described in Example 23, 204 mg of the title compound having an Rf value of 0.27 (developing solvent, benzene:ethyl acetate= 6:1 by volume) was obtained.

Nuclear Magnetic Resonance Spectrum (CDCl$_3$, 270 MHz) δ ppm: 1.55 (3H, doublet, J=6.9 Hz); 1.87–1.98 (1H, multiplet); 2.34–2.43 (1H, multiplet); 2.93–2.98 (1H, multiplet); 3.18 (1H, multiplet); 4.05, 4.71 (2H, AB-quartet, J=16.0 Hz); 5.53–5.65 (1H, multiplet); 5.85 (1H, doublet of doublets, J=10.7 & 2.4 Hz); 6.12 (1H, doublet, J=10.7 Hz); 6.19 (1H, doublet of doublets, J=10.7 & 9.3 Hz); 7.04 (1H, singlet); 7.18–7.21 (1H, multiplet); 7.44 (1H, doublet of doublets, J=16.0 & 9.3 Hz); 7.70–7.73 (1H, multiplet); 8.00 (1H, multiplet); 10.80 (1H, singlet).

Infrared Absorption Spectrum (CHCl$_3$) ν$_{max}$ cm$^{-1}$: 1740, 1720.

EXAMPLE 25

14-Stearoyl-16-palmitoylradicicol

Following a procedure similar to that described in Example 4, but using 442 mg of 14-stearoylradicicol (prepared as described in Example 7), 20 ml of dry methylene chloride, 186 μl of pyridine, a catalytic amount of dimethylaminopyridine and 202 mg of palmitoyl chloride, and then purifying the reaction mixture by silica gel column chromatography using a 2:1 by volume mixture of hexane and ethyl acetate, 581 mg of the title compound were obtained as crystals. Recrystallization of this product from pentane afforded 302 mg of white crystals.

Nuclear Magnetic Resonance Spectrum (CDCl$_3$, 270 MHz) δ ppm: 0.88 (6H, triplet, J=6.3 Hz); 1.22–1.42 (52H, multiplet); 1.54 (3H, doublet, J=6.8 Hz); 1.48–1.62 (1H, multiplet); 1.64–1.81 (4H, multiplet); 2.35–2.44 (1H, multiplet); 2.49 (2H, triplet, J=6.8 Hz); 2.58 (2H, triplet, J=7.3 Hz); 2.97–3.04 (1H, multiplet); 3.54 (1H, multiplet); 3.91, 4.03 (2H, AB-quartet, J=16.6 Hz); 5.36–5.45 (1H, multiplet); 5.78 (1H, doublet of doublets, J=10.7 & 3.9 Hz); 6.06 (1H, doublet, J=16.2 Hz); 6.14 (1H, doublet of doublets, J=10.7 & 10.3 Hz); 7.01 (1H, singlet); 7.52 (1H, doublet of doublets, J=16.1 & 10.3 Hz).

Infrared Absorption Spectrum (CHCl$_3$) ν$_{max}$ cm$^{-1}$: 1770, 1740.

EXAMPLE 26

14,16-Di(10-undecenoyl)radicicol

Following a procedure similar to that described in Example 1, but using 1459 mg of radicicol, 973 mg of 10-undecenoyl chloride, 37 ml of dry methylene chloride, 1.9 ml of pyridine and a catalytic amount of dimethylaminopyridine, 840 mg of the title compound were obtained.

Nuclear Magnetic Resonance Spectrum (CDCl$_3$, 270 MHz) δ ppm: 1.25–1.80 (24H, multiplet); 1.48–1.58 (1H, multiplet); 1.53 (3H, doublet, J=6.3 Hz); 1.99–2.10 (4H, multiplet); 2.35–2.47 (1H, multiplet); 2.49 (2H, triplet, J=7.7 Hz); 2.58 (2H, triplet, J=7.3 Hz); 2.93–3.04 (1H, multiplet); 3.51 (1H, multiplet); 3.91 & 4.03 (2H, AB-quartet, J=16.1 Hz); 4.90–5.04 (2H×2, multiplet); 5.35–5.46 (1H, multiplet); 5.74–5.90 (3H, multiplet); 6.06 (1H, doublet, J=16.1 Hz); 6.15 (1H, doublet of doublets, J=10.7 & 10.2 Hz); 7.01 (1H, singlet); 7.52 (1H, doublet of doublets, J=16.1 & 10.2 Hz).

Infrared Absorption Spectrum (CHCl$_3$) ν$_{max}$ cm$^{-1}$: 1770, 1735.

Mass spectrum (m/e): 696 (M$^+$)

Elemental analysis: Calculated for C$_{40}$H$_{53}$O$_8$Cl: C, 68.90%; H, 7.66%; Cl, 5.08%. Found: C, 68.02%; H, 7.53%, Cl, 5.41%.

EXAMPLE 27

14-(10-Undecenoyl)radicicol

The reaction mixture obtained in the final product treatment employed in Example 26 was fractionated and purified by chromatography through silica gel using a 2:1 by volume mixture of hexane and ethyl acetate as the eluent, to give 360 mg of the title compound having an Rf value of 0.3 (developing solvent, a 2:1 by volume mixture of hexane and ethyl acetate).

Nuclear Magnetic Resonance Spectrum (CDCl$_3$, 270 MHz) δ ppm: 1.25–1.48 (12H, multiplet); 1.55 (3H, doublet, J=6.8 Hz); 1.70–1.82 (2H, multiplet); 1.86–1.98 (1H, multiplet); 2.02–2.10 (2H, multiplet); 2.33–2.43 (1H, multiplet); 2.59 (2H, triplet, J=7.3 Hz); 2.93–2.98 (1H, multiplet); 3.17 (1H, multiplet); 3.97 and 4.69 (2H, AB-quartet, J=16.6 Hz); 4.92–5.03 (2H, multiplet); 5.51–5.62 (1H, multiplet); 5.73–5.90 (2H, multiplet); 6.10 (1H, doublet, J=16.1 Hz); 6.18 (1H, doublet of doublets, J=10.2, 9.28 Hz); 6.84 (1H, singlet); 7.43 (1H, doublet of doublets, J=16 1, 9.2 Hz); 10.78 (1H, singlet).

Infrared Absorption Spectrum (CHCl$_3$) ν$_{max}$ cm$^{-1}$: 1770, 1730.

Mass spectrum (m/e): 530 (M$^+$), 364.

EXAMPLE 28

14,16-Di(2-thenoyl)radicicol

Following a procedure similar to that described in Example 1, but using 1094 mg of radicicol, 528 mg of 2-thenoyl chloride, 28 ml of dry methylene chloride, 1.4 ml of pyridine and a catalytic amount of dimethylaminopyridine 1.0 g of the title compound was obtained.

Nuclear Magnetic Resonance Spectrum (CDCl$_3$, 270 MHz) δ ppm: 1.43 (3H, doublet, J=6.8 Hz); 1.34–1.45 (1H, multiplet); 2.18–2.26 (1H, multiplet); 2.96–3.03 (1H, multiplet); 3.58 (1H, multiplet); 3.96 & 4.23 (2H, AB-quartet, J=16.1 Hz); 5.14–5.26 (1H, multiplet); 5.76 (1H, doublet of doublets, J=11.0 & 4.3 Hz); 6.07 (1H, doublet, J=16.1 Hz); 6.16 (1H, doublet of doublets, J=11.0 & 10.2 Hz); 7.18–7.21 (2H, multiplet); 7.26 (1H, singlet); 7.45 (1H, doublet of doublets, J=16.6 & 10.2 Hz); 7.72 (2H, multiplet); 7.96–8.03 (2H, multiplet).

Infrared Absorption Spectrum (CHCl$_3$) ν$_{max}$ cm$^{-1}$: 1745, 1725.

Mass spectrum (m/e): 584 (M$^+$), 473.

Elemental analysis: Calculated for C$_{28}$H$_{21}$O$_8$ClS$_2$: C, 57.40%; H, 3.62%; Cl, 6.06%. Found: C, 57.61%; H, 3.76%; Cl, 5.93%.

EXAMPLE 29

14-(2-Thenoyl)radicicol

The reaction mixture obtained in the final product treatment employed in Example 28 was fractionated and purified by chromatography through silica gel, using a 6:1 by volume mixture of benzene and ethyl acetate as the eluent, to give 204 mg of the title compound having an Rf value of 0.27 (developing solvent, a 6:1 by volume mixture of benzene and ethyl acetate).

Nuclear Magnetic Resonance Spectrum (CDCl$_3$, 270 MHz) δ ppm: 1.55 (3H, doublet, J=6.9 Hz); 1.87–1.98 (1H, multiplet); 2.34–2.43 (1H, multiplet); 2.93–2.98 (1H, multiplet); 3.18 (1H, multiplet); 4.05 & 4.71 (2H, AB-quartet, J=16.0 Hz); 5.53–5.65 (1H, multiplet); 5.85 (1H, doublet of doublets, J=10.7 & 2.4 Hz); 6.12 (1H, doublet, J=17.0 Hz); 6.19 (1H, doublet of doublets, J=10.7 & 9.3 Hz); 7.04 (1H, singlet); 7.18–7.21 (1H, multiplet); 7.44 (1H, doublet of doublets, J=16.0 & 9.3 Hz); 7.70–7.73 (1H, multiplet); 8.00 (1H, multiplet); 10.21 (1H, singlet).

Infrared Absorption Spectrum (CHCl$_3$) ν$_{max}$ cm$^{-1}$: 1740, 1720.

Mass spectrum (m/e): 474 (M$^+$), 364.

EXAMPLE 30

14-Elaidoyl-16-palmitoylradicicol

Following a procedure similar to that described in Example 25, but using 500 mg of 14-elaidoylradicicol, 303 mg of palmitoyl chloride, 20 ml of dry methylene chloride, 0.2 ml of pyridine and a catalytic amount of dimethylaminopyridine, 484 mg of the title compound were obtained.

Nuclear Magnetic Resonance Spectrum (CDCl$_3$, 270 MHz) δ ppm: 0.87 (6H, triplet, J=6.8 Hz); 1.2–18 (48H, multiplet); 1.53 (3H, doublet, J=6.3 Hz); 1.92–2.00 (4H, multiplet); 2.35–2.45 (1H, multiplet); 2.49 (2H, triplet, J=7.8 Hz); 2.58 (2H, triplet, J=7.3 Hz); 2.96–3.05 (1H, multiplet); 3.52 (1H, multiplet); 3.91 & 4.03 (2H, AB-quartet, J=16.6 Hz); 5.36–5.47 (3H, multiplet); 5.78 (1H, doublet of doublets, J=10.7 & 3.4 Hz); 6.06 (1H, doublet, J=16.1 Hz); 6.14 (1H, doublet of doublets, J=18.7 & 10.2 Hz); 7.01 (1H, singlet); 7.51 (1H, doublet of doublets, J=16.1 & 10.2 Hz).

Infrared Absorption Spectrum (CHCl$_3$) $v_{max}$ cm$^{-1}$: 1770, 1735.

Elemental analysis Calculated for C$_{52}$H$_{79}$O$_8$Cl: C, 71.98%; H, 9.18%; Cl, 4.09%. Found: C, 71.26%; H, 9.45%; Cl, 3.93%.

EXAMPLE 31

14,16-Dimyristoylradicicol

Following a procedure similar to that described in Example 1, but using 1.28 g of radicicol, 1.04 g of myristoyl chloride, 35 ml of dry methylene chloride, 1.76 ml of pyridine and a catalytic amount of dimethylaminopyridine, 0.80 g of the title compound was obtained.

Nuclear Magnetic Resonance Spectrum (CDCl$_3$, 270 MHz) δ ppm: 0.88 (6H, triplet, J=6.6 Hz); 1.2–1.5 (40H, multiplet); 1.54 (3H, doublet, J=6.8 Hz); 1.45–1.6 (1H, multiplet); 1.6–1.8 (4H, multiplet); 2.35–2.45 (1H, multiplet); 2.50 (2H, triplet, J=6.8 Hz); 2.59 (2H, triplet, J=7.5 Hz); 2.98–3.04 (1H, multiplet); 3.50–3.53 (1H, multiplet); 3.92 (1H, doublet, J=16.4 Hz); 4.03 (1H, doublet, J=16.4 Hz); 5.3–5.5 (1H, multiplet); 5.79 (1H, doublet of doublets, J=10.7 & 3.9 Hz); 6.06 (1H, doublet, 16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1735.

Elemental analysis: Calculated for C$_{46}$H$_{69}$O$_8$Cl: C, 70.34%; H, 8.85%; Cl, 4.51%. Found: C, 70.43%; H, 8.68%; Cl, 4.46%.

EXAMPLE 32

14-Myristoylradicicol

The reaction mixture obtained in the final product treatment employed in Example 31 was fractionated and purified by chromatography through silica gel, using a 2:1 by volume mixture of hexane and ethyl acetate as the eluent, to give 543 mg of the title compound having an Rf value of 0.7 (developing solvent, a 1:1 by volume mixture of hexane and ethyl acetate).

Nuclear Magnetic Resonance Spectrum (CDCl$_3$, 270 MHz) δ ppm: 1.26 (3H, triplet, J=6.9 Hz); 1.2–1.5 (20H, multiplet); 1.55 (3H, doublet, J=6.8 Hz); 1.7–1.8 (2H, multiplet); 1.85–2.0 (1H, multiplet); 2.38 (1H, doublet of triplets, J=15.6 & 3.4 Hz); 2.59 (2H, triplet, J=7.5 Hz); 2.95 (1H, doublet of triplets, J=8.8 & 2.4 Hz); 3.16 (1H, multiplet); 3.98 (1H, doublet, J=16.6 Hz); 4.69 (1H, doublet, J=16.6 Hz); 5.52–5.59 (1H, multiplet); 5.84 (1H, doublet of doublets, J=10.7 & 2.4 Hz); 6.10 (1H, doublet, J=16.1 Hz); 6.18 (1H, doublet of doublets, J=10.7 & 10.3 Hz); 6.84 (1H, singlet); 7.43 (1H, doublet of doublets, J=16.1 & 10.3 Hz).

Infrared Absorption Spectrum (CHCl$_3$) $v_{max}$ cm$^{-1}$: 1770.

Elemental analysis: Calculated for C$_{32}$H$_{43}$O$_7$Cl: C, 66.83%; H, 7.54%; Cl, 6.16%. Found: C, 66.83%; H, 7.60%; Cl, 6.01%.

EXAMPLE 33

14-Myristoyl-16-palmitoylradicicol

Following a procedure similar to that described in Example 25, but using 539 mg of 14-myristoylradicicol, 509 mg of palmitoyl chloride, 15 ml of dry methylene chloride, 0.47 ml of pyridine and a catalytic amount of dimethylaminopyridine, 742 mg of the title compound were obtained.

Nuclear Magnetic Resonance Spectrum (CDCl$_3$, 270 MHz) δ ppm: 0.88 (6H, triplet, J=6.6 Hz); 1.2–1.5 (44H, multiplet); 1.54 (3H, doublet, J=6.8 Hz); 1.5–1.6 (1H, multiplet); 1.6–1.8 (4H, multiplet); 2.3–2.45 (1H, multiplet); 2.50 (2H, triplet, J=7.3 Hz); 2.59 (2H, triplet, J=7.6 Hz); 2.98–3.04 (1H, multiplet); 3.51–3.52 (1H, multiplet); 3.92 (1H, doublet, J=16.1 Hz); 4.03 (1H, doublet, J=16.1 Hz); 5.38–5.43 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1740.

Elemental analysis: Calculated for C$_{48}$H$_{73}$O$_8$Cl: C, 70.87%; H, 9.04%; Cl, 4.36%. Found: C, 70.21%; H, 9.32%; Cl, 3.95%.

EXAMPLE 34

14,16-Dilinoleoylradicicol

Following a procedure similar to that described in Example 1, but using 814 mg of radicicol, 800 mg of linoleoyl chloride, 22 ml of dry methylene chloride, 1.09 ml of pyridine and a catalytic amount of dimethylaminopyridine, 761 mg of the title compound were obtained.

Nuclear Magnetic Resonance Spectrum (CDCl$_3$, 270 MHz) δ ppm: 0.89 (6H, triplet, J=6.8 Hz); 1.2–1.4 (28H, multiplet); 1.54 (3H, doublet, J=7.8 Hz); 1.49–1.61 (1H, multiplet); 1.63–1.80 (4H, multiplet); 2.0–2.1 (8H, multiplet); 2.36–2.44 (1H, multiplet); 2.50 (2H, triplet, J=7.8 Hz); 2.59 (2H, triplet, J=7.6 Hz); 2.78 (4H, doublet of doublets, J=5.9 & 5.4 Hz); 2.98–3.03 (1H, multiplet); 3.52 (1H, multiplet); 3.92 (1H, doublet, J=16.3 Hz); 4.03 (1H, doublet, J=16.3 Hz); 5.25–5.45 (9H, multiplet); 5.79 (1H, doublet of doublets, J=10.3 & 3.7 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1740.

Elemental analysis: Calculated for C$_{54}$H$_{76}$O$_8$Cl: C, 72.99%; H, 8.62%; Cl, 3.99%. Found: C, 72.89%; H, 8.79%; Cl, 3.94%.

EXAMPLE 35

14-Linoleoylradicicol

The reaction mixture obtained in the final product treatment employed in Example 34 was fractionated and purified by chromatography through silica gel, using a 2:1 by volume mixture of hexane and ethyl acetate as the eluent, to give 662 mg of the title compound having an Rf value of 0.72 (developing solvent, a 1:1 by volume mixture of hexane and ethyl acetate).

Nuclear Magnetic Resonance Spectrum (CDCl$_3$, 270 MHz) δ ppm: 0.89 (3H, triplet, J=6.3 Hz); 1.2–1.5 (14H, multiplet); 1.55 (3H, doublet, J=6.8 Hz); 1.5–1.8 (3H, multiplet); 1.8–2.3 (4H, multiplet); 2.38 (1H, doublet of triplets, J=15.1 & 3.4 Hz); 2.60 (3H, triplet, J=7.2 Hz); 2.78 (1H, triplet, J=5.9 Hz); 2.9–3.0 (1H, multiplet); 3.17 (1H, broad singlet); 3.98 (1H, doublet, J=16.9 Hz); 4.38 (1H, doublet, J=16.9 Hz); 5.25–5.45 (2H, multiplet); 5.5–5.7 (3H, multiplet); 5.86 (1H, doublet of doublets, J=10.2 & 5.8 Hz); 6.11 (1H, doublet, J=16.1 Hz); 6.18 (1H, triplet, J=9.3 Hz); 6.84 (1H, singlet); 7.43 (1H, doublet of doublets, J=16.1 & 9.3 Hz).

Infrared Absorption Spectrum (CHCl$_3$) $v_{max}$ cm$^{-1}$: 1770, 1730.

EXAMPLE 36

14,16-Diretinoylradicicol

Following a procedure similar to that described in Example 12, but using 277 mg of radicicol, 665 mg of trans-vitamin A acid (trans-retinoic acid), 10 ml of dry tetrahydrofuran, 470 mg of dicyclohexylcarbodiimide and a catalytic amount of dimethylaminopyridine, 388 mg of the title compound were obtained.

Nuclear Magnetic Resonance Spectrum (CDCl$_3$, 270 MHz) δ ppm: 1.03 (6H, singlet); 1.04 (6H, singlet); 1.4–1.7 (9H, multiplet); 1.50 (3H, doublet, J=6.8 Hz); 1.72 (6H, singlet); 2.02 (3H, singlet); 2.03 (3H, singlet); 1.95–2.1 (4H, multiplet); 2.25–2.4 (1H, multiplet); 2.38 (3H, singlet); 2.39 (3H, singlet); 2.95–3.0 (1H, multiplet); 3.63 (1H, multiplet); 3.92 (1H, doublet, J=15.6 Hz); 4.15 (1H, doublet, J=15.6 Hz); 5.2–5.3 (1H, multiplet); 5.74 (1H, doublet of doublets, J=11.2, 4.9 Hz); 5.92 (1H, singlet); 5.99 (1H, singlet); 6.06 (1H, doublet, J=16.1 Hz); 6.1–6.25 (3H, multiplet); 6.25–6.4 (4H, multiplet); 7.10 (1H, singlet); 7.05–7.18 (2H, multiplet); 7.46 (1H, doublet of doublets, J=16.1 & 10.3 Hz).

Infrared Absorption Spectrum (CHCl$_3$) $v_{max}$ cm$^{-1}$: 1740.

Elemental analysis: Calculated for C$_{42}$H$_{45}$O$_8$Cl: C, 70.73%; H, 6.36%; Cl, 4.97%. Found: C, 70.38%; H, 6.46%; Cl, 4.66%.

EXAMPLE 37

14-(10-Undecenoyl)-16-palmittoylradicicol

Following a procedure similar to that described in Example 1, but using 400 mg of 14-(10-undecenoyl) radicicol (prepared as described in Example 27), 329 mg of palmitoyl chloride, 15 ml of dry methylene chloride, 0.19 ml of pyridine and a catalytic amount of dimethylaminopyridine, 477 mg of the title compound were obtained.

Nuclear Magnetic Resonance Spectrum (CDCl$_3$, 270 MHz) δ ppm: 0.88 (3H, triplet, J=6.8 Hz) 1.2–1.8 (39H, multiplet); 1.53 (3H, doublet, J=6.3 Hz); 2.00–2.10 (2H, multiplet); 2.36–2.45 (1H, multiplet); 2.49 (2H, triplet, J=6.3 Hz); 2.58 (2H, triplet, J=7.3 Hz); 2.97–3.05 (1H, multiplet); 3.52 (1H, multiplet); 3.91 & 4.03 (2H, AB-quartet, J=16.1 Hz); 4.90–5.03 (2H, multiplet); 5.35–5.47 (1H, multiplet); 5.75–5.90 (2H, multiplet); 6.06 (1H, doublet, J=16.6 Hz); 6.14 (1H, doublet of doublets, J=11.2 & 10.2 Hz); 7.01 (1H, singlet); 7.52 (1H, doublet of doublets, J=16.1 & 10.2 Hz).

Infrared Absorption Spectrum (CHCl$_3$) $v_{max}$ cm$^{-1}$: 1766, 1735.

Mass spectrum (m/e): 768 (M$^+$), 602, 364.

EXAMPLE 38

14,16-Bis(3-methylthiopropionyl)radicicol

Following a procedure similar to that described in Example 1, but using 1.56 g of radicicol, 0.71 g of 3-methylthiopropionyl chloride, 40 ml of dry methylene chloride, 2.15 ml of pyridine and a catalytic amount of dimethylaminopyridine, 447 mg of the title compound were obtained.

Nuclear Magnetic Resonance Spectrum (CDCl$_3$, 270 MHz) δ ppm: 1.54 (3H, triplet, J=6.4 Hz); 2.16 (3H, singlet); 2.17 (3H, singlet); 2.41 (1H, doublet of triplets, J=14.7 & 3.4 Hz); 2.83 (4H, singlet); 2.83–2.95 (4H, multiplet); 3.01 (1H, doublet of triplets, J=11.3 & 2.9 Hz); 3.51 (1H, multiplet); 3.93 (1H, doublet, J=16.4 Hz); 4.03 (1H, doublet, J=16.4 Hz); 5.42–5.47 (1H, multiplet); 5.80 (1H, doublet of doublets, J=10.7 & 3.4 Hz); 6.07 (1H, doublet, J=16.1 Hz); 6.15 (1H, doublet of doublets, J=10.7 & 10.3 Hz); 7.10 (1H, singlet); 7.52 (1H, doublet of doublets, J=16.1 & 10.3 Hz).

Infrared Absorption Spectrum (CHCl$_3$) $v_{max}$ cm$^{-1}$: 1775, 1740.

Elemental analysis: Calculated for C$_{26}$H$_{29}$O$_8$S$_2$Cl: C, 54.87%; H, 5.14; Cl, 6.23, S: 11.27%. Found: C, 55.26%; H, 5.37; Cl, 6.14, S: 11.01%.

EXAMPLE 39

14,16-Dipalmitoleoylradicicol

Following a procedure similar to that described in Example 12, but using 365 mg of radicicol, 636 mg of palmitoleic acid, 20 ml of dry methylene chloride, 716 mg of dicyclohexylcarbodiimide and a catalytic amount of dimethylaminopyridine, 654 mg of the title compound were obtained.

Nuclear Magnetic Resonance Spectrum (CDCl$_3$, 270 MHz) δ ppm: 0.88 (6H, triplet, J=6.6 Hz); 1.2–1.4 (32H, multiplet); 1.54 (3H, doublet, J=6.8 Hz); 1.5–1.6 (1H, multiplet); 1.6–1.8 (4H, multiplet); 1.9–2.1 (8H, multiplet); 2.35–2.45 (1H, multiplet); 2.50 (2H, triplet, J=7.3 Hz); 2.59 (2H, triplet, J=7.6 Hz); 2.98–3.04 (1H, multiplet); 3.52 (1H, multiplet); 3.92 (1H, doublet, J=16.4 Hz); 4.03 (1H, doublet, J=16.4 Hz); 5.3–5.5 (5H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1740.

Elemental analysis: Calculated for C$_{50}$H$_{73}$O$_8$Cl: C, 71.70%; H, 8.79%; Cl, 4.23%. Found: C, 72.09%; H, 8.89%; Cl, 3.56%.

EXAMPLE 40

14,16-Diisopalmitoylradicicol

Following a procedure similar to that described in Example 12, but using 500 mg of radicicol, 878 mg of isopalmitic acid, 20 ml of dry tetrahydrofuran, 848 mg of dicyclohexylcarbodiimide and a catalytic amount of dimethylaminopyridine, 1.12 g of the title compound were obtained.

Nuclear Magnetic Resonance Spectrum (CDCl$_3$, 270 MHz) δ ppm: 0.85–0.9 (12H, multiplet); 1.2–1.5 (40H, multiplet); 1.55 (3H, doublet, J=6.4 Hz); 1.4–1.9 (9H, multiplet); 2.40 (1H, doublet of doublets, J=14.6 & 2.6 Hz); 2.45–2.65 (2H, multiplet); 3.01 (1H, doublet of triplets, J=8.8 & 2.6 Hz); 3.53 (1H, multiplet); 3.89 (1H, doublet, J=16.4 Hz); 3.96 (1H, doublet, J=16.4 Hz); 5.4–5.5 (1H, multiplet); 5.84 (1H, doublet of doublets, J=10.7 & 3.4 Hz); 6.07 (1H, doublet, J=16.1 Hz); 6.15 (1H, triplet, J=10.7 Hz); 6.92 (1H, singlet); 7.62 (1H, doublet of doublets, J=16.1 & 10.7 Hz).

Infrared Absorption Spectrum (CHCl$_3$) $v_{max}$ cm$^{-1}$: 1770, 1740.

Elemental analysis: Calculated for C$_{50}$H$_{77}$O$_8$Cl: C, 71.36%; H, 9.22%; Cl, 4.21%. Found: C, 71.31%; H, 9.32%; Cl, 3.96%.

EXAMPLE 41

16-Palmitoylradicicol

Following a procedure similar to that described in Example 12, but using 364 mg of radicicol, 384 mg of palmitic acid, 15 ml of dry tetrahydrofuran, 309 mg of dicyclohexylcarbodiimide and a catalytic amount of dimethylaminopyridine, 62 mg of the title compound were obtained.

Nuclear Magnetic Resonance Spectrum (CDCl$_3$, 270 MHz) δ ppm: 0.88 (3H, triplet, J=6.3 Hz); 1.51 (3H, doublet, J=6.3 Hz); 1.20–1.76 (27H, multiplet); 2.34–2.43 (1H, multiplet); 2.50 (2H, triplet, J=7.8 Hz); 2.96–3.04 (1H, multiplet); 3.56 (1H, multiplet); 3.96 & 4.06 (2H, AB-quartet, J=16.6 Hz); 5.34–5.45 (1H, multiplet); 5.78 (1H, doublet of doublets, J=10.7 & 3.9 Hz); 6.04 (1H, singlet); 6.06 (1H, doublet, J=16.6 Hz); 6.15 (1H, doublet of doublets, J=10.7 & 10.2 Hz); 6.77 (1H, singlet); 7.56 (1H, doublet of doublets, J=16.1 & 10.2 Hz).

Infrared Absorption Spectrum (CHCl$_3$) $v_{max}$ cm$^{-1}$: 1765, 1730.

Mass spectrum (m/e): 602 (M$^+$).

Elemental analysis: Calculated for C$_{34}$H$_{47}$O$_7$Cl: C, 67.70%; H, 7.85%; Cl, 5.88%. Found: C, 67.10%; H, 7.62%; Cl, 5.72%.

EXAMPLE 42

14,16-Di(2-octynoyl)radicicol

Following a procedure similar to that described in Example 12, but using 730 mg of radicicol, 701 mg of 2-octynoic acid, 15 ml of dry tetrahydrofuran, 1.03 g of dicyclohexylcarbodiimide and a catalytic amount of dimethylaminopyridine, 611 mg of the title compound were obtained.

Nuclear Magnetic Resonance Spectrum (CDCl$_3$, 270 MHz) δ ppm: 0.91 (3H, triplet, J=6.8 Hz); 0.92 (3H, triplet, J=7.3 Hz); 1.2–1.6 (8H, multiplet); 1.56 (3H, doublet, J=6.8 Hz); 1.5–1.7 (4H, multiplet); 1.7–1.8 (1H, multiplet); 2.35–2.47 (5H, multiplet); 3.0–3.1 (1H, multiplet); 3.5–3.55 (1H, multiplet); 3.93 (1H, doublet, J=16.1 Hz); 4.26 (1H, doublet, J=16.1 Hz); 5.2–5.35 (1H, multiplet); 5.69 (1H, doublet of doublets, J=10.7 & 5.1 Hz); 6.06 (1H, doublet, J=16.1 Hz); 6.15 (1H, doublet of doublets, J=10.7 & 9.8 Hz); 7.11 (1H, singlet); 7.34 (1H, doublet of doublets, J=16.1 & 9.8 Hz).

Infrared Absorption Spectrum (CHCl$_3$) $v_{max}$ cm$^{-1}$: 2250, 1745.

Elemental analysis: Calculated for C$_{34}$H$_{37}$O$_8$Cl: C, 67.04%; H, 6.12%%; Cl, 5.82%. Found: C, 66.76%; H, 6.21%%; Cl, 5.76%.

EXAMPLE 43

14,16-Bis(12-allyloxycarbonylaminododecanoyl)radicicol

Following a procedure similar to that described in Example 12, but using 547 mg of radicicol, 3.75 g of 12-allyloxycarbonylaminododecanoic acid, 15 ml of dry 1-methyl-2-pyrrolidinone, 1.6 g of dicyclohexylcarbodiimide and a catalytic amount of dimethylaminopyridine, 418 mg of the title compound were obtained.

Nuclear Magnetic Resonance Spectrum (CDCl$_3$, 270 MHz) δ ppm: 1.2–1.61 (32H, multiplet); 1.54 (3H, doublet, J=6.8 Hz); 1.6–1.8 (4H, multiplet); 2.41 (1H, doublet of triplets, J=14.7 & 3.4 Hz); 2.50 (2H, triplet, J=7.3 Hz); 2.58 (2H, triplet, J=7.6 Hz); 3.01 (1H, doublet of triplets, J=8.3 & 4.3 Hz); 3.1–3.2 (4H, multiplet); 3.52 (1H, multiplet); 3.92 (1H, doublet, J=16.1 Hz); 4.03 (1H, doublet, J=16.1 Hz); 4.56 (4H, doublet, J=5.4 Hz); 4.72 (2H, broad singlet); 5.20 (2H, doublet of doublets, J=10.3 & 1.2 Hz); 5.30 (2H, doublet of doublets, J=17.1 & 1.2 Hz); 5.38–5.43 (1H, multiplet); 5.79 (1H, doublet of doublets, J=10.7 & 3.9 Hz); 5.85–5.99 (2H, multiplet); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1720.

Elemental analysis: Calculated for C$_{50}$H$_{71}$O$_{12}$N$_2$Cl: C, 67.74%; H, 7.72%; N, 3.02%; Cl, 3.82%. Found: C, 64.75%; H, 7.72%; N, 3.28%; Cl, 3.62%.

EXAMPLE 44

14,16-Dipentadecanoylradicicol

Following a procedure similar to that described in Example 12, but using 500 mg of radicicol, 830 mg of pentadecanoic acid, 15 ml of dry tetrahydrofuran, 707 mg of dicyclohexylcarbodiimide and a catalytic amount of dimethylaminopyridine, 782 mg of the title compound were obtained.

Nuclear Magnetic Resonance Spectrum (CDCl$_3$, 270 MHz) δ ppm: 0.88 (6H, triplet, J=6.6 Hz); 1.2–1.5 (44H, multiplet); 1.54 (3H, doublet, J=6.4 Hz); 1.5–1.6 (1H, multiplet); 1.6–1.8 (4H, multiplet); 2.40 (1H, triplet, J=13.7 & 3.1 Hz); 2.49 (2H, triplet, J=7.3 Hz); 2.59 (2H, triplet, J=7.6 Hz); 2.99–3.04 (1H, multiplet); 3.52 (1H, multiplet); 3.92 (1H, doublet, J=16.1 Hz); 4.03 (1H, doublet, J=16.1 Hz); 5.38–5.43 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.53 (1H, doublet of doublets, J=16.1 & 10.3 Hz).

Infrared Absorption Spectrum (CHCl$_3$) $v_{max}$ cm$^{-1}$: 1770, 1735.

Elemental analysis: Calculated for C$_{48}$H$_{73}$O$_8$Cl: C, 70.87%; H, 9.04%; Cl, 4.36%. Found: C, 71.11%; H, 9.16%; Cl, 3.97%.

EXAMPLE 45

14,16-Diheptadecanoylradicicol

Following a procedure similar to that described in Example 1, but using 730 mg of radicicol, 693 mg of heptadecanoyl chloride, 25 ml of dry methylene chloride, 1 ml of pyridine and a catalytic amount of dimethylaminopyridine, 539 mg of the title compound were obtained.

Nuclear Magnetic Resonance Spectrum (CDCl$_3$, 270 MHz) δ ppm: 0.88 (6H, triplet, J=6.6 Hz); 1.2–1.5 (52H, multiplet); 1.54 (3H, doublet, J=7.8 Hz); 1.5–1.6 (1H, multiplet); 1.6–1.8 (4H, multiplet); 2.40 (1H, doublet of triplets, J=14.7 & 3.4 Hz); 2.49 (2H, triplet, J=7.3 Hz); 2.59 (2H, triplet, J=7.6 Hz); 2.98–3.04 (1H, multiplet); 3.52 (1H, multiplet); 3.92 (1H, doublet, J=16.1 Hz); 4.03 (1H, doublet, J=16.1 Hz); 5.38–5.43 (1H, multiplet); 5.79 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1735.

Elemental analysis: Calculated for C$_{52}$H$_{81}$O$_8$Cl: C, 71.82%; H, 8.39%; Cl, 4.08%. Found: C, 71.98%; H, 9.42%; Cl, 3.93%.

EXAMPLE 46

14-Heptadecanoylradicicol

The reaction mixture obtained in the final product treatment employed in Example 45 was fractionated and purified by chromatography through silica gel, using a 3:1 by volume mixture of hexane and ethyl acetate as the eluent, to give 640 mg of the title compound having an Rf value of 0.5 (developing solvent, a 2:1 by volume mixture of hexane and ethyl acetate).

Nuclear Magnetic Resonance Spectrum (CDCl$_3$, 270 MHz) δ ppm: 0.88 (3H, triplet, J=6.6 Hz); 1.2–1.5 (26H, multiplet); 1.55 (3H, doublet, J=6.8 Hz); 1.7–1.85 (2H, multiplet); 1.85–2.0 (1H, multiplet); 2.38 (1H, doublet of triplets, J=16.1 & 2.4 Hz); 2.60 (2H, triplet, J=7.3 Hz); 2.92–2.97 (1H, multiplet); 3.17 (1H, multiplet); 3.98 (1H, doublet, J=16.6 Hz); 4.69 (1H, doublet, J=16.6 Hz); 5.52–5.60 (1H, multiplet); 5.84 (1H, doublet of doublets, J=10.7 & 2.9 Hz); 6.11 (1H, doublet, J=16.1 Hz); 6.18 (1H, doublet of doublets, J=10.7 & 10.3 Hz); 6.84 (1H, singlet); 7.43 (1H, doublet of doublets, J=16.1 & 10.3 Hz).

Infrared Absorption Spectrum (CHCl$_3$) $v_{max}$ cm$^{-1}$: 1770, 1730.

Elemental analysis: Calculated for C$_{35}$H$_{49}$O$_7$Cl: C, 68.11%; H, 8.00%; Cl, 5.74%. Found: C, 68.55%; H, 8.39%; Cl, 5.27%.

EXAMPLE 47

14,16-Bis{16-[(2-trimethylsilylethoxy)methoxy]hexadecanoyl]}radicicol

Following a procedure similar to that described in Example 12, but using 121 mg of radicicol, 470 mg of 16-[(2-trimethylsilylethoxy)methoxy]hexadecanoic acid, 7 ml of dry tetrahydrofuran, 240 mg of dicyclohexylcarbodiimide and a catalytic amount of dimethylaminopyridine, 481 mg of the title compound were obtained.

Nuclear Magnetic Resonance Spectrum (CDCl$_3$, 270 MHz) δ ppm: 0.88–0.95 (4H, multiplet); 1.1–2.0 (52H, multiplet); 1.51 (3H, doublet, J=6.8 Hz); 2.35–2.60 (5H, multiplet); 3.0 (1H, multiplet); 3.46–3.65 (9H, multiplet); 3.91 (1H, doublet, J=16.1 Hz); 4.00 (1H, doublet, J=16.1 Hz); 4.64 (4H, singlet); 5.37 (1H, multiplet); 5.76 (1H, doublet of doublets, J=10.7 & 3.9 Hz); 6.04 (1H, doublet, J=16.1 Hz); 6.12 (1H, doublet of doublets, J=10.7 & 10.3 Hz); 6.99 (1H, singlet); 7.50 (1H, doublet of doublets, J=16.1 & 10.3 Hz).

Infrared Absorption Spectrum (CHCl$_3$) $v_{max}$ cm$^{-1}$: 1770, 1735.

EXAMPLE 48

14,1,6-Dicinnamoylradicicol

Following a procedure similar to that described in Example 1, but using 912 mg of radicicol, 500 mg of cinnamoyl chloride, 30 ml of dry methylene chloride, 1.22 ml of pyridine and a catalytic amount of dimethylaminopyridine, 442 mg of the title compound were obtained.

Nuclear Magnetic Resonance Spectrum (CDCl$_3$, 270 MHz) δ ppm: 1.51 (3H, doublet, J=6.4 Hz); 1.5–1.6 (1H, multiplet); 2.33 (1H, doublet of triplets, J=15.1 & 3.9 Hz); 2.97–3.05 (1H, multiplet); 3.62 (1H, multiplet); 3.96 (1H, doublet, J=16.1 Hz); 4.19 (1H, doublet, J=16.1 Hz); 5.25–5.35 (1H, multiplet); 5.77 (1H, doublet of doublets, J=11.2 & 4.4 Hz); 6.09 (1H, doublet, J=16.1 Hz); 6.17 (1H, doublet of doublets, J=11.7 & 10.7 Hz); 6.58 (1H, doublet, J=16.1 Hz); 6.62 (1H, doublet, J=16.1 Hz); 7.21 (1H, singlet); 7.4–7.5 (6H, multiplet); 7.49 (1H, doublet of doublets, J=16.1 & 10.3 Hz); 7.55–7.65 (4H, multiplet); 7.87 (1H, doublet, J=16.1 Hz); 7.92 (1H, doublet, J=16.1 Hz).

Infrared Absorption Spectrum (CHCl$_3$) $v_{max}$ cm$^{-1}$: 1740.

EXAMPLE 49

14-Cinnamoylradicicol

The reaction mixture obtained in the final product treatment employed in Example 48 was fractionated and then purified by chromatography through silica gel, using a 2:1 by volume mixture of hexane and ethyl acetate as the eluent, to give 527 mg of the title compound having an Rf value of 0.6 (developing solvent, a 1:1 by volume mixture of hexane and ethyl acetate).

Nuclear Magnetic Resonance Spectrum (CDCl$_3$, 270 MHz) δ ppm: 1.56 (3H, doublet, J=6.8 Hz); 1.93 (1H, multiplet); 2.39 (1H, doubled doublet of doublets, J=15.1 Hz); 2.96 (1H, doubled doublet of doublets, J=8.8 Hz); 3.20 (1H, multiplet); 4.01 & 4.70 (2H, AB-quartet, J=16.8 Hz); 5.57 (1H, multiplet); 5.85 (1H, doublet of doublets, J=10.7 & 2.9 Hz); 6.13 (1H, doublet, J=16.1 Hz); 6.20 (1H, doublet of doublets, J=10.7 & 9.3 Hz); 6.62 (1H, doublet, J=16.1 Hz); 6.97 (1H, singlet); 7.35–7.5 (4H, multiplet); 7.5–7.65 (2H, multiplet); 7.91 (1H, doublet, J=16.1 Hz).

EXAMPLE 50

14,16-Bis(6-phenylhexanoyl)radicicol

Following a procedure similar to that described in Example 12, but using 500 mg of radicicol, 659 mg of 6-phenylhexanoic acid, 15 ml of dry tetrahydrofuran, 707 mg of dicyclohexylcarbodiimide and a catalytic amount of dimethylaminopyridine, 704 mg of the title compound were obtained.

Nuclear Magnetic Resonance Spectrum (CDCl$_3$, 270 MHz) δ ppm: 1.52 (3H, doublet, J=16.4 Hz); 1.3–1.9 (13H, multiplet); 2.37 (1H, doubled doublet of doublets, J=14.6 Hz); 2.45–2.7 (8H, multiplet); 3.00 (1H, doubled doublet of doublets, J=7.8 Hz); 3.51 (1H, multiplet); 3.91 & 4.02 (2H, AB-quartet, J=16.1 Hz); 5.38 (1H, multiplet); 5.79 (1H, doublet of doublets, J=10.7 & 3.9 Hz); 6.06 (1H, doublet, J=16.1 Hz); 6.15 (1H, doublet of doublets, J=11.2 & 10.2 Hz); 6.98 (1H, singlet); 7.1–7.35 (10H, multiplet); 7.52 (1H, doublet of doublets, J=16.1 & 10.2 Hz).

Infrared Absorption Spectrum (CHCl$_3$) $v_{max}$ cm$^{-1}$: 1770, 1730.

Elemental analysis: Calculated for C$_{42}$H$_{45}$O$_8$Cl: C, 70.73%; H, 6.36%; Cl, 4.97%. Found: C, 70.38%; H, 6.46%; Cl, 4.66%.

EXAMPLE 51

14,16-Di(2-furanacryloyl)radicicol

Following a procedure similar to that described in Example 12, but using 500 mg of radicicol, 568 mg of 2-furanacrylic acid, 15 ml of dry tetrahydrofuran, 707 mg of dicyclohexylcarbodiimide and a catalytic amount of dimethylaminopyridine, 746 mg of the title compound were obtained.

Nuclear Magnetic Resonance Spectrum (CDCl$_3$, 270 MHz) δ ppm: 1.51 (3H, doublet, J=6.3 Hz); 1.45–1.6 (1H, multiplet); 2.34 (1H, doubled doublet of doublets, J=14.6 Hz); 2.99 (1H, multiplet); 3.61 (1H, multiplet); 3.94 & 4.16 (2H, AB-quartet, J=16.1 Hz); 5.30 (1H, multiplet); 5.76 (1H, doublet of doublets, J=11.2 & 4.4 Hz); 6.08 (1H, doublet, J=16.1 Hz); 6.14 (1H, doublet of doublets, J=11.7 & 3.4 Hz); 6.43 (1H, doublet, J=15.6 Hz); 6.48 (1H, doublet, J=15.6 Hz); 6.53 (2H, multiplet); 6.74 (2H, multiplet); 7.18 (1H, singlet); 7.47 (1H, doublet of doublets, J=16.1 & 10.3 Hz); 7.59 (1H, doublet, J=15.6 Hz); 7.64 (1H, doublet, J=15.6 Hz).

Infrared Absorption Spectrum (CHCl$_3$) ν$_{max}$ cm$^{-1}$: 1740.

Elemental analysis: Calculated for C$_{32}$H$_{25}$O$_{10}$Cl: C, 63.53%; H, 4.17%; Cl, 5.86%. Found: C, 63.31%; H, 4.37%; Cl, 5.49%.

EXAMPLE 52

14,16-Di[3-(2-thienyl)acryloyl]radicicol

Following a procedure similar to that described in Example 12, but using 365 mg of radicicol, 462 mg of 3-(2-thienyl)acrylic acid, 10 ml of dry tetrahydrofuran, 619 mg of dicyclohexylcarbodiimide and a catalytic amount of dimethylaminopyridine, 526 mg of the title compound were obtained.

Nuclear Magnetic Resonance Spectrum (CDCl$_3$, 270 MHz) δ ppm: 1.51 (3H, doublet, J=6.4 Hz); 1.55 (1H, multiplet); 2.34 (1H, doubled doublet of doublets, J=14.6 Hz); 3.01 (1H, doubled doublet of doublets, J=7.2 Hz); 3.62 (1H, multiplet); 3.96 & 4.17 (2H, AB-quartet, J=16.1 Hz); 5.30 (1H, multiplet); 5.77 (1H, doublet of doublets, J=10.8 & 4.4 Hz); 6.08 (1H, doublet, J=16.1 Hz); 6.29 (1H, doublet of doublets, J=11.7 & 10.8 Hz); 6.35 (1H, doublet, J=15.6 Hz); 6.40 (1H, doublet, J=15.6 Hz); 7.1 (2H, multiplet); 7.18 (1H, singlet); 7.36 (2H, triplet, J=3.4 Hz); 7.48 (3H, multiplet); 7.96 (1H, doublet, J=15.6 Hz); 8.01 (1H, doublet, J=15.6 Hz).

Infrared Absorption Spectrum (CHCl$_3$) ν$_{max}$ cm$^{-1}$: 1740.

Elemental analysis: Calculated for C$_{32}$H$_{25}$O$_8$S$_2$Cl: C, 60.33%; H, 3.96%; Cl, 5.56%; S, 10.87%. Found: C, 60.32%; H, 4.26%; Cl, 5.17%; S, 9.74%.

EXAMPLE 53

14,16-Bis(12-tritylthioaminododecanoyl)radicicol

Following a procedure similar to that described in Example 12, but using 500 mg of radicicol, 2.013 g of 12-tritylthioaminododecanoic acid, 60 ml of dry tetrahydrofuran, 848 mg of dicyclohexylcarbodiimide and a catalytic amount of dimethylaminopyridine, 965 mg of the title compound were obtained.

Nuclear Magnetic Resonance Spectrum (CDCl$_3$, 270 MHz) δ ppm: 1.0–1.8 (37H, multiplet); 1.53 (3H, doublet, J=16.3 Hz); 2.40 (1H, doubled doublet of doublets, J=14.7 Hz); 2.45–2.62 (8H, multiplet); 3.00 (1H, doubled doublet of doublets, J=7.8 Hz); 3.51 (1H, multiplet); 3.91 & 4.03 (2H, AB-quartet, J=16.4 Hz); 5.40 (1H, multiplet); 5.78 (1H, doublet of doublets, J=10.7 & 3.4 Hz); 6.06 (1H, doublet, J=16.1 Hz); 6.14 (1H, doublet of doublets, J=11.2 & 10.2 Hz); 7.01 (1H, singlet); 7.2–7.4 (30H, multiplet); 7.52 (1H, doublet of doublets, J=16.1 & 10.8 Hz).

Infrared Absorption Spectrum (CHCl$_3$) ν$_{max}$ cm$^{-1}$: 1770, 1735.

Elemental analysis: Calculated for C$_{80}$H$_{91}$O$_8$N$_2$S$_2$Cl: C, 73.45%; H, 7.01%; N, 2.14%; Cl, 2.71; S, 4.90%. Found: C, 73.40%; H, 7.17%; N, 2.12%; Cl, 3.06; S, 5.01%.

EXAMPLE 54

14,16-Dilinolenoylradicicol

Following a procedure similar to that described in Example 1, but using 280 mg of radicicol, 600 mg of linolenoyl chloride, 11 ml of dry methylene chloride, 0.37 ml of pyridine and a catalytic amount of dimethylaminopyridine, 552 mg of the title compound were obtained.

Nuclear Magnetic Resonance Spectrum (hexadeuterated dimethyl sulfoxide, 270 MHz) δ ppm: 0.84 (3H, triplet, J=5.4 Hz); 0.85 (3H, triplet, J=6.4 Hz); 1.1–1.8 (24H, multiplet); 1.47 (3H, doublet, J=6.3 Hz); 1.5–1.8 (1H, multiplet); 1.9–2.2 (8H, multiplet); 2.4–2.5 (1H, multiplet); 2.5–2.7 (5H, multiplet); 2.7–2.8 (6H, multiplet); 3.05–3.15 (1H, multiplet); 3.40 (1H, multiplet); 3.84 (1H, doublet, J=16.1 Hz); 4.00 (1H, doublet, J=16.1 Hz); 5.2–5.5 (13H, multiplet); 5.78 (1H, doublet of doublets, J=10.8 & 3.9 Hz); 6.08 (1H, doublet, J=16.1 Hz); 6.25 (1H, doublet of doublets, J=10.8 & 10.2 Hz); 7.38 (1H, singlet); 7.38 (1H, doublet of doublets, J=16.1 & 10.2 Hz).

Infrared Absorption Spectrum (CHCl$_3$) ν$_{max}$ cm$^{-1}$: 1770, 1735.

Elemental analysis: Calculated for C$_{54}$H$_{73}$O$_8$Cl: C, 73.24%; H, 8.31%; Cl, 4.00%. Found: C, 73.35%; H, 8.60%; Cl, 3.91%.

EXAMPLE 55

14,16-Bistridecanoylradicicol

Following a procedure similar to that described in Example 12, but using 400 mg of radicicol, 588 mg of tridecanoic acid, 6 ml of dry tetrahydrofuran, 566 mg of dicyclohexylcarbodiimide and a catalytic amount of dimethylaminopyridine, 688 mg of the title compound were obtained.

Nuclear Magnetic Resonance Spectrum (CDCl$_3$, 270 MHz) δ ppm: 0.88 (6H, triplet, J=6.5 Hz); 1.1–1.5 (36H, multiplet); 1.54 (3H, doublet, J=6.3 Hz); 1.6–1.8 (5H, multiplet); 2.35–2.45 (1H, multiplet); 2.50 (2H, triplet, J=7.5 Hz); 2.59 (2H, triplet, J=7.5 Hz); 3.02 (1H, multiplet); 3.51 (1H, multiplet); 3.86 & 3.97 (2H, AB-quartet, J=13.6 Hz); 5.40 (1H, multiplet); 5.79 (1H, doublet of doublets, J=10.7 & 3.9 Hz); 6.06 (1H, doublet, J=16.1 Hz); 6.15 (1H, doublet of doublets, J=11.3 & 10.3 Hz); 7.01 (1H, singlet); 7.52 (1H, doublet of doublets, J=16.1 & 10.2 Hz).

Infrared Absorption Spectrum (CHCl$_3$) ν$_{max}$ cm$^{-1}$: 1770, 1735.

Elemental analysis: Calculated for C$_{44}$H$_{65}$O$_8$Cl: C, 69.77%; H, 8.65%; Cl, 4.68%. Found: C, 69.54%; H, 8.69%; Cl, 4.66%.

EXAMPLE 56

14,16-Dilauroylradicicol

Following a procedure similar to that described in Example 1, but using 730 mg of radicicol, 656 mg of lauroyl chloride, 14 ml of dry methylene chloride, 0.97 ml of pyridine and a catalytic amount of dimethylaminopyridine, 644 mg of the title compound were obtained.

Nuclear Magnetic Resonance Spectrum (CDCl$_3$, 270 MHz) δ ppm: 0.88 (6H, triplet, J=6.6 Hz); 1.2–1.5 (32H, multiplet); 1.54 (3H, doublet, J=6.3 Hz); 1.48–1.5 (1H, multiplet); 1.5–1.8 (4H, multiplet); 2.40 (1H, doubled doublet of doublets, J=4.9 Hz); 2.49 (2H, triplet, J=6.6 Hz); 2.59 (2H, triplet, J=7.6 Hz); 3.01 (1H, multiplet); 3.51 (1H, multiplet); 3.92 & 4.03 (2H, AB-quartet, J=16.6 Hz); 5.40 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 9.7 Hz); 7.02 (1H, singlet); 7.52 (1H, doublet of doublets, J=16.1 & 10.2 Hz).

Infrared Absorption Spectrum (CHCl$_3$) $v_{max}$ cm$^{-1}$: 1770, 1735.

Elemental analysis: Calculated for C$_{42}$H$_{61}$O$_8$Cl: C, 69.16%; H, 8.43%; Cl, 4.86%. Found: C, 69.11%; H, 8.65%; Cl, 4.89%.

EXAMPLE 57

14,16-Bis(16-acetylthiohexadecanoyl)radicicol

Following a procedure similar to that described in Example 12, but using 120 mg of radicicol, 206 mg of 16-acetylthiohexadecanoic acid, 5 ml of dry tetrahydrofuran, 330 mg of dicyclohexylcarbodiimide and a catalytic amount of dimethylaminopyridine, 235 mg of the title compound were obtained.

Nuclear Magnetic Resonance Spectrum (CDCl$_3$, 270 MHz) δ ppm: 1.2–1.8 (52H, multiplet); 1.53 (3H, doublet, J=6.3 Hz); 2.31 (6H, singlet); 2.34–2.45 (1H, multiplet); 2.50 (2H, triplet, J=7.3 Hz); 2.58 (2H, triplet, J=7.3 Hz); 2.86 (2H×2, triplet, J=7.31 Hz); 2.97–3.05 (1H, multiplet); 3.53 (1H, multiplet); 3.91 & 4.03 (2H, AB-quartet, J=16.1 Hz); 5.37–5.45 (1H, multiplet); 5.78 (1H, doublet of doublets, J=10.7 & 3.9 Hz); 6.06 (1H, doublet, J=16.1 Hz); 6.15 (1H, doublet of doublets, J=10.7 & 10.7 Hz); 7.01 ,(1H, singlet); 7.52 (1H, doublet of doublets, J=16.1 & 10.7 Hz).

Infrared Absorption Spectrum (CHCl$_3$) $v_{max}$ cm$^{-1}$: 1770.

EXAMPLE 58

14,16-Di(11-cyanoundecanoyl)radicicol

Following a procedure similar to that described in Example 1, but using 365 mg of radicicol, 11-cyanoundecanoyl chloride (prepared from 1.055 g of 11-cyanoundecanoic acid), 7 ml of dry methylene chloride, 1.21 ml of pyridine and a catalytic amount of dimethylaminopyridine, 707 mg of the title compound were obtained.

Nuclear Magnetic Resonance Spectrum (CDCl$_3$, 270 MHz) δ ppm: 1.25–1.5 (24H, multiplet); 1.54 (3H, doublet, J=6.3 Hz); 1.55–1.85 (9H, multiplet); 2.34 (4H, triplet, J=7.0 Hz); 2.41 (1H, doubled doublet of doublets, J=14.7 Hz); 2.50 (2H, doublet of doublets, J=8.3 & 7.3 Hz); 2.59 (2H, triplet, J=7.8 Hz); 3.01 (1H, multiplet); 3.51 (1H, multiplet); 3.92 & 4.03 (2H, AB-quartet, J=16.1 Hz); 5.40 (1H, multiplet); 5.79 (1H, doublet of doublets, J=10.7 & 3.9 Hz); 6.06 (1H, doublet, J=16.1 Hz); 6.15 (1H, doublet of doublets, J=11.2 & 10.2 Hz); 7.02 (1H, singlet); 7.53 (1H, doublet of doublets, J=16.1 & 10.2 Hz).

Infrared Absorption Spectrum (CHCl$_3$) $v_{max}$ cm$^{-1}$: 2250, 1770, 1735.

Elemental analysis: Calculated for C$_{42}$H$_{55}$O$_8$N$_2$Cl: C, 67.14%; H, 7.38%; N, 3.73%; Cl, 4.72%. Found: C, 67.13%; H, 7.53%; N, 3.84%; Cl, 4.37%.

EXAMPLE 59

14,16-Di[11-(9-fluorenyl)methoxycarbonylaminododecanoyl]radicicol

Following a procedure similar to that described in Example 12, but using 67 mg of radicicol, 280 mg of 11-(9-fluorenyl)methoxycarbonylaminododecanoic acid, 10 ml of dry tetrahydrofuran, 132 mg of dicyclohexylcarbodiimide and a catalytic amount of dimethylaminopyridine, 194 mg of the title compound were obtained.

Nuclear Magnetic Resonance Spectrum (CDCl$_3$, 270 MHz) δ ppm: 1.2–1.45 (28H, multiplet); 1.53 (3H, doublet, J=6.3 Hz); 1.45–1.8 (9H, multiplet); 2.40 (1H, doubled doublet of doublets, J=14.6 Hz); 2.49 (2H, doublet of doublets, J=8.3 & 7.3 Hz); 2.58 (1H, triplet, J=7.5 Hz); 3.00 (1H, multiplet); 3.19 (4H, multiplet); 3.52 (1H, multiplet); 3.92 & 4.03 (2H, AB-quartet, J=16.6 Hz); 4.22 (2H, triplet, J=6.8 Hz); 4.40 (4H, doublet, J=6.8 Hz); 4.76 (2H, broad singlet); 5.40 (1H, multiplet); 5.78 (1H, doublet of doublets, J=10.7 & 3.4 Hz); 6.06 (1H, doublet, J=16.1 Hz); 6.14 (1H, triplet, J=10.7 Hz); 7.02 (1H, singlet); 7.25–7.45 (8H, multiplet); 7.52 (1H, doublet of doublets, J=16.1 & 10.2 Hz); 7.59 (4H, doublet, J=7.3 Hz); 7.76 (4H, doublet, J=7.3 Hz).

Elemental analysis: Calculated for C$_{72}$H$_{83}$O$_{12}$N$_2$Cl: C, 71.83%; H, 6.95%; N, 2.33%; Cl, 2.94%. Found: C, 71.72%; H, 7.10%; N, 2.51%; Cl, 2.79%.

EXAMPLE 60

14,16-Di(11-methoxycarbonylundecanoyl)radicicol

Following a procedure similar to that described in Example 1, but using 300 mg of radicicol, 11-methoxycarbonylundecanoyl chloride (prepared from 1 g of 11-methoxycarbonylundecanoic acid), 6 ml of dry methylene chloride, 0.4 ml of pyridine and a catalytic amount of dimethylaminopyridine, 570 mg of the title compound were obtained.

Nuclear Magnetic Resonance Spectrum (CDCl$_3$, 270 MHz) δ ppm: 1.2–1.45 (24H, multiplet); 1.54 (3H, doublet, J=6.8 Hz); 1.5–1.8 (9H, multiplet); 2.31 (4H, triplet, J=7.5 Hz); 2.40 (1H, doubled doublet of doublets, J=15.1 Hz); 2.50 (2H, triplet, J=7.0 Hz); 3.0 (1H, multiplet); 3.52 (1H, multiplet); 3.67 (6H, singlet); 3.92 & 4.03 (2H, AB-quartet, J=16.1 Hz); 5.4 (1H, multiplet); 5.79 (1H, doublet of doublets, J=11.2 & 3.9 Hz); 6.06 (1H, doublet, J=16.1 Hz); 6.15 (1H, triplet, J=10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1772, 1740, 1735.

Elemental analysis: Calculated for C$_{44}$H$_{61}$O$_{12}$Cl: C, 64.65%; H, 7.52%; Cl, 4.34%. Found: C, 64.60%; H, 7.49%; Cl, 4.25%.

EXAMPLE 61

14,16-Dicaproylradicicol

Following a procedure similar to that described in Example 1, but using 365 mg of radicicol, 460 mg of caproyl chloride, 7 ml of dry methylene chloride, 0.49 ml of pyridine and a catalytic amount of dimethylaminopyridine, 575 mg of the title compound were obtained.

Nuclear Magnetic Resonance Spectrum (CDCl$_3$, 270 MHz) δ ppm: 0.89 (6H, triplet, J=6.3 Hz); 1.2–1.5 (24H, multiplet); 1.45–1.6 (1H, multiplet); 1.54 (3H, doublet, J=6.6 Hz); 1.6–1.8 (4H, multiplet); 2.41 (1H, dm, J=14.5 Hz); 2.50 (2H, triplet, J=7.3 Hz); 2.59 (2H, triplet, J=7.3 Hz); 3.01 (1H, multiplet); 3.52 (1H, multiplet); 3.92 (1H, doublet, J=16.5 Hz); 4.03 (1H, doublet, J=16.5 Hz); 5.42 (1H, multiplet); 5.79 (1H, doublet of doublets, J=10.6 & 3.9 Hz); 6.11 (1H, doublet, J=15.9 Hz); 6.17 (1H, triplet, J=5.9

Hz); 7.02 (1H, singlet); 7.53 (1H, doublet of doublets, J=16.5 & 10.6 Hz).

Infrared Absorption Spectrum (CHCl₃) $v_{max}$ cm⁻¹: 1770, 1730.

Elemental analysis: Calculated for $C_{38}H_{53}O_8Cl$: C, 67.79%; H, 7.93%; Cl, 5.27%. Found: C, 67.76%; H, 7.80%; Cl, 5.02%.

EXAMPLE 62

14,16-Diundecanoylradicicol

Following a procedure similar to that described in Example 1, but using 365 mg of radicicol, 450 mg of undecanoyl chloride, 7 ml of dry methylene chloride, 0.49 ml of pyridine and a catalytic amount of dimethylaminopyridine, 586 mg of the title compound were obtained.

Nuclear Magnetic Resonance Spectrum (CDCl₃, 270 MHz) δ ppm: 0.89 (6H, triplet, J=6.4 Hz); 1.2–1.5 (28H, multiplet); 1.45–1.6 (1H, multiplet); 1.54 (3H, doublet, J=6.6 Hz); 1.6–1.8 (4H, multiplet); 2.40 (1H, dm, J=15.2 Hz); 2.50 (2H, triplet, J=7.9 Hz); 2.59 (2H, triplet, J=7.3 Hz); 3.0 (1H, multiplet); 3.5 (1H, multiplet); 3.92 (1H, doublet, J=16.2 Hz); 4.03 (1H, doublet, J=16.2 Hz); 5.42 (1H, multiplet); 5.79 (1H, doublet of doublets, J=10.7 & 3.9 Hz); 6.06 (1H, doublet, J=16.5 Hz); 6.15 (1H, triplet, J=10.7 Hz); 7.02 (1H, singlet); 7.53 (1H, doublet of doublets, J=16.5 & 10.5 Hz).

Infrared Absorption Spectrum (CHCl₃) $v_{max}$ cm⁻¹: 1770, 1730.

Elemental analysis: Calculated for $C_{40}H_{57}O_8Cl$: C, 68.50%; H, 8.19%; Cl, 5.06%. Found: C, 68.56%; H, 8.04%; Cl, 4.86%.

EXAMPLE 63

14,16-Dieicosanoylradicicol

Following a procedure similar to that described in Example 1, but using 300 mg of radicicol, eicosanoyl chloride (prepared from 1.2 g of eicosanoic acid), 5 ml of dry methylene chloride, 0.4 ml of pyridine and a catalytic amount of dimethylaminopyridine, 646 mg of the title compound were obtained.

Nuclear Magnetic Resonance Spectrum (CDCl₃, 270 MHz) δ ppm: 0.88 (6H, triplet, J=6.3 Hz); 1.2–1.5 (44H, multiplet); 1.45–1.6 (1H, multiplet); 1.54 (3H, doublet, J=7.3 Hz); 1.6–1.8 (4H, multiplet); 2.40 (1H, dm, J=14.5 Hz); 2.50 (2H, triplet, J=7.3 Hz); 2.59 (2H, triplet, J=7.3 Hz); 3.02 (1H, multiplet); 3.52 (1H, multiplet); 3.92 (1H, doublet, J=16.1 Hz); 4.03 (1H, doublet, J=16.1 Hz); 5.40 (1H, multiplet); 5.79 (1H, doublet of doublets, J=10.5 & 3.3 Hz); 6.07 (1H, doublet, J=16.5 Hz); 6.15 (1H, triplet, J=10.5 Hz); 7.02 (1H, singlet); 7.53 (1H, doublet of doublets, J=16.5 & 10.5 Hz).

Infrared Absorption Spectrum (CHCl₃) $v_{max}$ cm⁻¹: 1770, 1740.

Elemental analysis: Calculated for $C_{58}H_{93}O_8Cl$: C, 73.04%; H, 9.83%; Cl, 3.72%. Found: C, 72.99%; H, 9.93%; Cl, 3.77%.

EXAMPLE 64

14,16-Di(16-hydroxyhexadecanoyl)radicicol

Following a procedure similar to that described in Example 12, but using 365 mg of radicicol, 681 mg of 16-hydroxyhexadecanoic acid, 20 ml of dry tetrahydrofuran, 516 mg of dicyclohexylcarbodiimide and a catalytic amount of dimethylaminopyridine, 661 mg of the title compound were obtained as crystals melting at 85°–86° C.

Nuclear Magnetic Resonance Spectrum (CDCl₃+D₂O, 270 MHz) δ ppm: 1.2–1.5 (48H, multiplet); 1.54 (3H, doublet, J=6.3 Hz); 1.5–1.65 (1H, multiplet); 1.65–1.8 (4H, multiplet); 2.41 (1H, doubled doublet of doublets, J=14.7 Hz); 2.50 (2H, doublet of doublets, J=7.8 & 6.8 Hz); 2.59 (2H, triplet, J=6.8 Hz); 3.02 (1H, multiplet); 3.51 (1H, multiplet); 3.63 (4H, triplet, J=6.3 Hz); 3.92 (1H, doublet, J=16.1 Hz); 4.03 (1H, doublet, J=16.1 Hz); 5.40 (1H, multiplet); 5.79 (1H, doublet of doublets, J=10.7 & 3.9 Hz); 6.06 (1H, doublet, J=16.1 Hz); 6.15 (1H, triplet, J=10.3 Hz); 7.02 (1H, singlet); 7.52 (1H, doublet of doublets, J=16.1 & 10.3 Hz).

Infrared Absorption Spectrum (CHCl₃) $v_{max}$ cm⁻¹: 1770, 1738.

Elemental analysis: Calculated for $C_{50}H_{77}O_{10}Cl$: C, 68.74%; H, 8.88%; Cl, 4.06%. Found: C, 68.62%; H, 8.92%; Cl, 4.32%.

EXAMPLE 65

14,16-Di(12-hydroxydodecanoyl)radicicol

Following a procedure similar to that described in Example 12, but using 365 mg of radicicol, 1.8 g of 12-hydroxydodecanoic acid, 20 ml of dry tetrahydrofuran, 1 g of dicyclohexylcarbodiimide and a catalytic amount of dimethylaminopyridine, 485 mg of the title compound were obtained.

Nuclear Magnetic Resonance Spectrum (CDCl₃, 270 MHz) δ ppm: 1.2–1.5 (32H, multiplet); 1.54 (3H, doublet, J=6.3 Hz); 1.5–1.65 (1H, multiplet); 1.65–1.8 (4H, multiplet); 2.41 (1H, doubled doublet of doublets, J=14.7 Hz); 3.02 (1H, multiplet); 2.50 (2H, doublet of doublets, J=7.7 & 6.4 Hz); 2.59 (2H, doublet, J=7.3 Hz); 3.52 (1H, multiplet); 3.64 (6H, triplet, J=6.6 Hz); 3.91 (1H, doublet, J=16.1 Hz); 4.03 (1H, doublet, J=16.1 Hz) 5.41 (1H, multiplet); 5.79 (1H, doublet of doublets, J=10.7 & 3.9 Hz); 6.06 (1H, doublet, J=16.1 Hz); 6.15 (1H, triplet, J=10.2 Hz); 7.02 (1H, singlet); 7.52 (1H, doublet of doublets, J=16.1 & 10.2 Hz).

Infrared Absorption Spectrum (CHCl₃) $v_{max}$ cm⁻¹: 1770, 1735.

Elemental analysis: Calculated for $C_{42}H_{61}O_{10}Cl$: C, 66.26%; H, 8.08%; Cl, 4.66%. Found: C, 66.22%; H, 7.99%; Cl, 4.38%.

EXAMPLE 66

14,16-Di(10-hydroxydecanoyl)radicicol

Following a procedure similar to that described in Example 12, but using 365 mg of radicicol, 471 mg of 10-hydroxydecanoic acid, 25 ml of dry tetrahydrofuran, 516 mg of dicyclohexylcarbodiimide and a catalytic amount of dimethylaminopyridine, 332 mg of the title compound were obtained.

Nuclear Magnetic Resonance Spectrum (CDCl₃+D₂O, 270 MHz) δ ppm: 1.2–1.5 (24H, multiplet); 1.54 (3H, doublet, J=6.3 Hz); 1.5–1.8 (5H, multiplet); 2.41 (1H, dm, J=14.7 Hz); 2.50 (2H, doublet of doublets, J=8.3 & 6.8 Hz); 2.59 (2H, doublet, J=7.3 Hz); 3.01 (1H, multiplet); 3.52 (1H, multiplet); 3.63 (6H, triplet, J=6.8 Hz); 3.92 (1H, doublet, J=16.1 Hz); 4.03 (1H, doublet, J=16.1 Hz); 5.40 (1H, multiplet); 5.79 (1H, doublet of doublets, J=10.7 & 3.9 Hz); 6.07 (1H, doublet, J=16.1 Hz); 6.15 (1H, doublet of doublets, J=11.2 & 10.3 Hz); 7.02 (1H, singlet); 7.53 (1H, doublet of doublets, J=16.1 & 10.2 Hz).

Infrared Absorption Spectrum (CHCl$_3$) $v_{max}$ cm$^{-1}$: 1770, 1738.

Elemental analysis: Calculated for C$_{38}$H$_{53}$O$_{10}$Cl: C, 64.71%; H, 7.57%; Cl, 5.03%. Found: C, 64.31%; H, 7.21%; Cl, 5.40%.

EXAMPLE 67

14,16-Dimyristoleoylradicicol

Following a procedure similar to that described in Example 1, but using 365 mg of radicicol, myristoleoyl chloride prepared from 900 mg of myristoleic acid, 7 ml of dry methylene chloride, 0.97 ml of pyridine and a catalytic amount of dimethylaminopyridine, 510 mg of the title compound were obtained.

Nuclear Magnetic Resonance Spectrum (CDCl$_3$, 270 MHz) δ ppm: 0.89 (6H, triplet, J=6.2 Hz); 1.2–1.5 (24H, multiplet); 1.53 (3H, doublet, J=6.3 Hz); 1.45–1.6 (1H, multiplet); 1.6–1.8 (4H, multiplet); 2.02 (8H, doublet, J=5.9 Hz); 2.40 (1H, doubled doublet of doublets, J=14.7 Hz); 2.49 (2H, doublet of doublets, J=7.8 & 6.8 Hz); 2.59 (2H, triplet, J=7.3 Hz); 3.01 (1H, multiplet); 3.51 (1H, multiplet); 3.92 (1H, doublet, J=16.6 Hz); 4.03 (1H, doublet, J=16.6 Hz); 5.27–5.45 (5H, multiplet); 5.79 (1H, doublet of doublets, J=10.7 & 3.4 Hz); 6.06 (1H, doublet, J=16.1 Hz); 6.15 (1H, doublet of doublets, J=11.7 & 10.7 Hz); 7.02 (1H, singlet); 7.51 (1H, doublet of doublets, J=16.6 & 10.7 Hz).

Infrared Absorption Spectrum (CHCl$_3$) $v_{max}$ cm$^{-1}$: 1770, 1740.

EXAMPLE 68

14,16-Di(11-carbamoylundecanoyl)radicicol

Following a procedure similar to that described in Example 1, but using 365 mg of radicicol, 11-carbamoylundecanoyl chloride prepared from 900 mg of 11-carbamoylundecanoic acid, 8 ml of dry methylene chloride, 0.97 ml of pyridine and a catalytic amount of dimethylaminopyridine, 273 mg of the title compound were obtained.

Nuclear Magnetic Resonance Spectrum (CDCl$_3$, 270 MHz) δ ppm: 1.25–1.5 (24H, multiplet); 1.54 (3H, doublet, J=6.8 Hz); 1.5–1.8 (9H, multiplet); 2.22 (4H, triplet, J=7.6 Hz); 2.41 (1H, doubled doublet of doublets, J=15.1 Hz); 2.50 (2H, triplet, J=7.8 Hz); 2.59 (2H, triplet, J=7.3 Hz); 3.00 (1H, multiplet); 3.52 (1H, multiplet); 3.92 (1H, doublet, J=16.1 Hz); 4.02 (1H, doublet, J=16.1 Hz); 5.40 (1H, multiplet); 5.45 (4H, broad singlet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz).

Infrared Absorption Spectrum (CHCl$_3$) $v_{max}$ cm$^{-1}$: 1770, 1730.

Elemental analysis: Calculated for C$_{42}$H$_{59}$O$_{10}$N$_2$Cl.1/3CHCl$_3$: C, 61.47%; H, 7.23%; N, 3.39%; Cl, 8.57%. Found: C, 61.69%; H, 7.31%; N, 3.61%; Cl, 8.72%.

EXAMPLE 69

14,16-Di[10-(methoxyethoxymethoxy)decanoyl] radicicol

Following a procedure similar to that described in Example 12, but using 400 mg of radicicol, 758 mg of 10-(methoxyethoxymethoxy)decanoic acid, 6 ml of dry tetrahydrofuran, 567 mg of dicyclohexylcarbodiimide and a catalytic amount of dimethylaminopyridine, 829 mg of the title compound were obtained.

Infrared Absorption Spectrum (CHCl$_3$) $v_{max}$ cm$^{-1}$: 1775, 1735.

Nuclear Magnetic Resonance Spectrum (CDCl$_3$, 270 MHz) δ ppm: 1.2–1.5 (24H, multiplet); 1.54 (3H, doublet, J=6.4 Hz); 1.5–1.8 (5H, multiplet); 2.40 (1H, doubled doublet of doublets, J=15.1 Hz); 2.50 (2H, doublet of doublets, J=6.6 & 8.0 Hz); 2.59 (2H, triplet, J=7.6 Hz); 3.01 (1H, multiplet); 3.40 (6H, singlet); 3.47–3.52 (9H, multiplet); 3.55–3.65 (4H, multiplet); 3.92 (1H, doublet, J=16.1 Hz); 4.03 (1H, doublet, J=16.1 Hz); 4.72 (4H, singlet); 5.41 (1H, multiplet); 5.79 (1H, doublet of doublets, J=10.7 & 3.9 Hz); 6.06 (1H, doublet, J=16.1 Hz); 6.15 (1H, triplet, J=10.3 Hz); 7.02 (1H, singlet); 7.52 (1H, doublet of doublets, J=16.1 & 10.7 Hz).

EXAMPLE 70

14,16-Di[10-(methoxymethoxy)decanoyl]radicicol

Following a procedure similar to that described in Example 12, but using 400 mg of radicicol, 595 mg of 10-(methoxymethoxy)decanoic acid, 6 ml of dry tetrahydrofuran, 567 mg of dicyclohexylcarbodiimide and a catalytic amount of dimethylaminopyridine, 739 mg of the title compound were obtained.

Infrared Absorption Spectrum (CHCl$_3$) $v_{max}$ cm$^{-1}$: 1775, 1735.

Nuclear Magnetic Resonance Spectrum (CDCl$_3$, 270 MHz) δ ppm: 1.25–1.5 (24H, multiplet); 1.54 (3H, doublet, J=6.4 Hz); 1.5–1.8 (5H, multiplet); 2.40 (1H, doubled doublet of doublets, J=14.7 Hz); 2.50 (2H, doublet of doublets, J=7.8 & 6.8 Hz); 2.57 (2H, triplet, J=7.5 Hz); 3.00 (1H, multiplet); 3.36 (6H, singlet); 3.51 (4H, triplet, J=6.1 Hz); 3.5 (1H, multiplet); 3.92 (1H, doublet, J=16.6 Hz); 4.03 (1H, doublet, J=16.6 Hz); 4.62 (4H, singlet); 5.41 (1H, multiplet); 5.79 (1H, doublet of doublets, J=10.7 & 3.9 Hz); 6.06 (1H, doublet, J=6.1 Hz); 6.15 (1H, doublet of doublets, J=10.7 & 9.7 Hz); 7.02 (1H, singlet); 7.52 (1H, doublet of doublets, J=16.6 & 10.3 Hz).

EXAMPLE 71

14,16-Di[12-(methoxyethoxymethoxy)dodecanoyl] radicicol

Following a procedure similar to that described in Example 12, but using 400 mg of radicicol, 856 mg of 12-(methoxyethoxymethoxy)dodecanoic acid, 6 ml of dry tetrahydrofuran, 567 mg of dicyclohexylcarbodiimide and a catalytic amount of dimethylaminopyridine, 893 mg of the title compound were obtained.

Infrared Absorption Spectrum (CHCl$_3$) $v_{max}$ cm$^{-1}$: 1770, 1738.

Nuclear Magnetic Resonance Spectrum (CDCl$_3$, 270 MHz) δ ppm: 1.24–1.45 (32H, multiplet); 1.54 (3H, doublet, J=6.8 Hz); 1.45–1.6 (1H, multiplet); 1.65–1.77 (4H, multiplet); 2.36–2.44 (1H, multiplet); 2.50 (2H, doublet of doublets, J=7.8 & 6.8 Hz); 2.59 (2H, triplet, J=7.3 Hz); 2.98–3.04 (1H, multiplet); 3.40 (6H, singlet); 3.51–3.58 (9H, multiplet); 3.68–3.71 (4H, multiplet); 3.97 (2H, AB-quartet, J=16.1 Hz); 4.72 (4H, singlet); 5.38–5.43 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz)

EXAMPLE 72

14,16-Di[12-(methoxymethoxy)dodecanoyl] radicicol

Following a procedure similar to that described in Example 12, but using 400 mg of radicicol, 716 mg of 12-(methoxymethoxy)dodecanoic acid, 7 ml of dry tetrahydrofuran, 567 mg of dicyclohexylcarbodiimide and a catalytic amount of dimethylaminopyridine, 756 mg of the title compound were obtained.

Infrared Absorption Spectrum (CHCl$_3$) $v_{max}$ cm$^{-1}$: 1767, 1730.

Nuclear Magnetic Resonance Spectrum (CDCl$_3$, 270 MHz) δ ppm: 1.23–1.47 (32H, multiplet); 1.5–1.6 (1H, multiplet); 1.54 (3H, doublet, J=6.8 Hz); 1.6–1.8 (4H, multiplet); 2.36–2.44 (1H, multiplet); 2.50 (2H, triplet, J=7.8 Hz); 2.59 (2H, triplet, J=7.6 Hz); 2.98–3.04 (1H, multiplet); 3.36 (6H, singlet); 3.52 (4H, triplet, J=6.6 Hz); 3.45–3.55 (1H, multiplet); 3.97 (2H, AB-quartet, J=16.1 Hz); 4.62 (4H, singlet); 5.16–5.23 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz)

EXAMPLE 73

14,16-Di[16-(methoxyethoxymethoxy) hexadecanoyl]radicicol

Following a procedure similar to that described in Example 12, but using 400 mg of radicicol, 996 mg of 16-(methoxyethoxymethoxy)hexadecanoic acid, 6 ml of dry tetrahydrofuran, 567 mg of dicyclohexylcarbodiimide and a catalytic amount of dimethylaminopyridine, 946 mg of the title compound were obtained.

Infrared Absorption Spectrum (CHCl$_3$) $v_{max}$ cm$^{-1}$: 1765, 1734.

Nuclear Magnetic Resonance Spectrum (CDCl$_3$, 270 MHz) δ ppm: 1.2–1.46 (48H, multiplet); 1.54 (3H, doublet, J=6.4 Hz); 1.47–1.62 (1H, multiplet); 1.65–1.80 (4H, multiplet); 2.36–2.44 (1H, multiplet); 2.49 (2H, triplet, J=7.3 Hz); 2.59 (2H, triplet, J=7.3 Hz); 2.98–3.04 (1H, multiplet); 3.40 (6H, singlet); 3.5–3.6 (9H, multiplet); 3.67–3.72 (4H, multiplet); 3.97 (2H, AB-quartet, J=16.1 Hz); 4.71 (4H, singlet); 5.38–5.43 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.52 (1H, doublet of doublets, J=16.1 & 10.3 Hz)

EXAMPLE 74

14,16-Di[16-(methoxymethoxy)hexadecanoyl] radicicol

Following a procedure similar to that described in Example 12, but using 400 mg of radicicol, 865 mg of 10-(methoxymethoxy)decanoic acid, 7 ml of dry tetrahydrofuran, 567 mg of dicyclohexylcarbodiimide and a catalytic amount of dimethylaminopyridine, 543 mg of the title compound were obtained.

Infrared Absorption Spectrum (CHCl$_3$) $v_{max}$ cm$^{-1}$: 1737, 1768.

Nuclear Magnetic Resonance Spectrum (CDCl$_3$, 270 MHz) δ ppm: 1.2–1.46 (48H, multiplet); 1.54 (3H, doublet, J=6.4 Hz); 1.5–1.6 (1H, multiplet); 1.6–1.77 (4H, multiplet); 2.36–2.44 (1H, multiplet); 2.50 (2H, triplet, J=7.3 Hz); 2.59 (2H, triplet, J=7.3 Hz); 2.98–3.04 (1H, multiplet); 3.36 (6H, singlet); 3.52 (4H, triplet, J=6.6 Hz); 3.48–3.58 (1H, multiplet); 3.97.(2H, AB-quartet, J=16.1 Hz); 4.62 (4H, singlet); 5.38–5.43 (1H, multiplet); 5.79 (1H, doublet of doublets, J=10.7 & 3.9 Hz); 6.06 (1H, doublet, J=16.1 Hz); 6.15 (1H, doublet of doublets, J=10.7 & 10.3 Hz); 7.02 (1H, singlet); 7.51 (1H, doublet of doublets, J=16.6 & 10.3 Hz).

We claim:

1. A compound of formula (I):

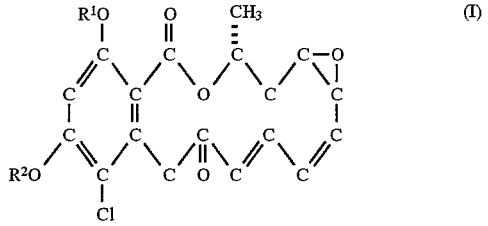

wherein R$^1$ and R$^2$ are independently a group R$^3$—CO—, in which R$^3$ is an unsubstituted alkyl group having 9 to 20 carbon atoms or an unsubstituted alkenyl group having 9 to 20 carbon atoms.

2. A pharmaceutical composition for the treatment of tumors, which comprises an effective amount of an active compound in admixture with a pharmaceutically acceptable carrier or diluent, wherein said active compound is selected from the group consisting of compounds of formula (I) and salts thereof, as defined in claim 1.

3. A method for the treatment of tumors, which comprises administering to an animal an effective amount of an active compound, wherein said active compound is selected from the group consisting of compounds of formula (I) and salts thereof, as defined in claim 1.

* * * * *